（12）United States Patent
Stehlik

(10) Patent No.: US 11,065,299 B2
(45) Date of Patent: Jul. 20, 2021

(54) COMPOSITIONS AND METHODS FOR MODULATION OF IMMUNE RESPONSE

(71) Applicant: Northwestern University, Evanston, IL (US)

(72) Inventor: Christian Stehlik, Evanston, IL (US)

(73) Assignee: Northwestern University, Evanston, IL (US)

( * ) Notice: Subject to any disclaimer, the term of this patent is extended or adjusted under 35 U.S.C. 154(b) by 7 days.

(21) Appl. No.: 16/444,909

(22) Filed: Jun. 18, 2019

(65) Prior Publication Data

US 2020/0397858 A1 Dec. 24, 2020

Related U.S. Application Data

(63) Continuation of application No. 15/117,629, filed as application No. PCT/US2015/015761 on Feb. 13, 2015, now abandoned.

(60) Provisional application No. 61/939,499, filed on Feb. 13, 2014.

(51) Int. Cl.
*A61K 38/00* (2006.01)
*A61K 38/17* (2006.01)

(52) U.S. Cl.
CPC .............................. *A61K 38/1709* (2013.01)

(58) Field of Classification Search
CPC .................................................. A61K 38/1709
See application file for complete search history.

(56) References Cited

U.S. PATENT DOCUMENTS

| | | |
|---|---|---|
| 2002/0187922 A1 | 12/2002 | Bertin et al. |
| 2007/0031410 A1 | 2/2007 | Harton et al. |
| 2008/0233638 A1 | 9/2008 | Reed et al. |
| 2013/0296256 A1 | 11/2013 | Yang et al. |
| 2016/0192627 A1* | 7/2016 | Harton .............. C12N 15/8509 800/9 |

FOREIGN PATENT DOCUMENTS

WO   WO 2015/123493   8/2015

OTHER PUBLICATIONS

Chen et al. Inflammatory responses and inflammation-associated diseases in organs. Oncotarget, 2018, vol. 9, (No. 6), pp. 7204-7218 (Year: 2018).*
Almeida et al. The PYRIN Domain-only Protein POP1 Inhibits Inflammasome Assembly and Ameliorates Inflammatory Disease. Immunity. Aug. 18, 2015;43(2):264-76 (Year: 2015).*
Dinarello et al. Grand Challenge in Inflammation. Front Immunol. 2012; 3: 12 (Year: 2012).*
Pahwa et al. Chronic Inflammation. NIH (Year: 2020).*
Healthline—Understanding and managing chronic inflammation. By Han Seunggu. Accessed on Dec. 29, 2020 on https://www.healthline.com/health/chronic-inflammation (Year: 2018).*
Baroja-Mazo et al. The NLRP3 inflammasome is released as a particulate danger signal that amplifies the inflammatory response. Nat Immunol. Aug. 2014;15(8):738-48.
Bauernfeind et al. Cutting edge: NF-kappaB activating pattern recognition and cytokine receptors license NLRP3 inflammasome activation by regulating NLRP3 expression. J Immunol. Jul. 15, 2009;183(2):787-91.
Bedoya et al., Pyrin-only protein 2 modulates NF-kappaB and disrupts ASC:CLR interactions. J Immunol. Mar. 15, 2007;178(6):3837-45.
Boisson et al. Immunodeficiency, autoinflammation and amylopectinosis in humans with inherited HOIL-1 and LUBAC deficiency. Nat Immunol. Dec. 2012;13(12):1178-86.
Boyden & Dietrich. Nalp1b controls mouse macrophage susceptibility to anthrax lethal toxin. Nat Genet. Feb. 2006;38(2):240-4.
Brown et al. Lipopolysaccharide stimulates platelets through an IL-1β autocrine loop. J Immunol. Nov. 15, 2013;191(10):5196-203.
Bryan et al. Activation of inflammasomes requires intracellular redistribution of the apoptotic speck-like protein containing a caspase recruitment domain. J Immunol. Mar. 1, 2009;182(5):3173-8.
Brydges et al. Divergence of IL-1, IL-18, and cell death in NLRP3 inflammasomopathies. J Clin Invest. Nov. 2013;123(11):4695-705.
Brydges et al. Inflammasome-mediated disease animal models reveal roles for innate but not adaptive immunity. Immunity. Jun. 19, 2009;30(6):875-87.
Cai et al. Prion-like polymerization underlies signal transduction in antiviral immune defense and inflammasome activation. Cell. Mar. 13, 2014;156(6):1207-22.
Calvano et al. A network-based analysis of systemic inflammation in humans. Nature. Oct. 13, 2005;437(7061):1032-7.
Cassel et al. The Nalp3 inflammasome is essential for the development of silicosis. Proc Natl Acad Sci U S A. Jul. 1, 2008;105(26):9035-40.
Cridland et al. The mammalian PYHIN gene family: phylogeny, evolution and expression. BMC Evol Biol. Aug. 7, 2012;12:140.
De Nardo et al. New insights into mechanisms controlling the NLRP3 inflammasome and its role in lung disease. Am J Pathol. Jan. 2014;184(1):42-54.
Dinarello et al. Interleukin-1 in the pathogenesis and treatment of inflammatory diseases. Blood. Apr. 7, 2011;117(14):3720-32.
Dorfleutner et al. Cellular pyrin domain-only protein 2 is a candidate regulator of inflammasome activation. Infect Immun. Mar. 2007;75(3):1484-92.
Dostert et al. Innate immune activation through Nalp3 inflammasome sensing of asbestos and silica. Science. May 2, 2008;320(5876):674-7.

(Continued)

*Primary Examiner* — James H Alstrum-Acevedo
*Assistant Examiner* — Mercy H Sabila
(74) *Attorney, Agent, or Firm* — Casimir Jones SC; Davie W. Staple

(57) ABSTRACT

Provided herein are compositions and methods for modulation of immune response via PYRIN domain-only proteins POP1 and/or POP3. In particular, POP1 and/or POP3 are inhibited to enhance an immune response (e.g., to treat or prevent infection), or POP1 and/or POP3 are administered or activated to reduce an immune response (e.g., to treat or prevent autoimmune or inflammatory disease).

3 Claims, 55 Drawing Sheets
(27 of 55 Drawing Sheet(s) Filed in Color)

Specification includes a Sequence Listing.

(56) References Cited

OTHER PUBLICATIONS

Exline et al. Microvesicular caspase-1 mediates lymphocyte apoptosis in sepsis. PLoS One. Mar. 18, 2014;9(3):e90968.
Fernandes-Alnemri et al. The pyroptosome: a supramolecular assembly of ASC dimers mediating inflammatory cell death via caspase-1 activation. Cell Death Differ. Sep. 2007;14(9):1590-604.
Fernandes-Alnemri et al. The AIM2 inflammasome is critical for innate immunity to Francisella tularensis. Nat Immunol. May 2010;11(5):385-93.
Franchi et al. Cytosolic flagellin requires Ipaf for activation of caspase-1 and interleukin 1beta in salmonella-infected macrophages. Nat Immunol. Jun. 2006;7(6):576-82.
Franklin et al. The adaptor ASC has extracellular and 'prionoid' activities that propagate inflammation. Nat Immunol. Aug. 2014;15(8):727-37.
Gough et al. The use of human CD68 transcriptional regulatory sequences to direct high-level expression of class A scavenger receptor in macrophages in vitro and in vivo. Immunology. Jul. 2001;103(3):351-61.
Gram et al., Inflammasomes and viruses: cellular defence versus viral offence. J Gen Virol. Oct. 2012;93(Pt 10):2063-2075.
Greaves et al. Functional comparison of the murine macrosialin and human CD68 promoters in macrophage and nonmacrophage cell lines. Genomics. Nov. 15, 1998;54(1):165-8.
Gross et al. Bioluminescence imaging of myeloperoxidase activity in vivo. Nat Med. Apr. 2009;15(4):455-61.
Guarda et al. Type I interferon inhibits interleukin-1 production and inflammasome activation. Immunity. Feb. 25, 2011;34(2):213-23.
Henao-Mejia et al. Inflammasomes: far beyond inflammation. Nat Immunol. Mar. 19, 2012;13(4):321-4.
Hoffman et al. Genetic and molecular basis of inflammasome-mediated disease. J Biol Chem. Apr. 1, 2011;286(13):10889-96.
Hoffman et al. Mutation of a new gene encoding a putative pyrin-like protein causes familial cold autoinflammatory syndrome and Muckle-Wells syndrome. Nat Genet. Nov. 2001;29(3):301-5.
Hornung et al. Silica crystals and aluminum salts activate the NALP3 inflammasome through phagosomal destabilization. Nat Immunol. Aug. 2008;9(8):847-56.
Iqbal et al. Human CD68 promoter GFP transgenic mice allow analysis of monocyte to macrophage differentiation in vivo. Blood. Oct. 9, 2014;124(15):e33-44.
Jin et al. LRRFIP2 negatively regulates NLRP3 inflammasome activation in macrophages by promoting Flightless-I-mediated caspase-1 inhibition. Nat Commun. 2013;4:2075.
Jin et al. Structure of the absent in melanoma 2 (AIM2) pyrin domain provides insights into the mechanisms of AIM2 autoinhibition and inflammasome assembly. J Biol Chem. May 10, 2013;288(19):13225-35.
Juliana et al. Non-transcriptional priming and deubiquitination regulate NLRP3 inflammasome activation. J Biol Chem. Oct. 19, 2012;287(43):36617-22.
Kaser et al. Interferon-alpha induces interleukin-18 binding protein in chronic hepatitis C patients. Clin Exp Immunol. Aug. 2002;129(2):332-8.
Kayagaki et al. Non-canonical inflammasome activation targets caspase-11. Nature. Oct. 16, 2011;479(7371):117-21.
Kelpe et al., Sodium nitrite protects against kidney injury induced by brain death and improves post-transplant function. Kidney Int. Aug. 2012;82(3):304-13.
Kerur et al. IFI16 acts as a nuclear pathogen sensor to induce the inflammasome in response to Kaposi Sarcoma-associated herpesvirus infection. Cell Host Microbe. May 19, 2011;9(5):363-75.
Khare et al. An NLRP7-containing inflammasome mediates recognition of microbial lipopeptides in human macrophages. Immunity. Mar. 23, 2012;36(3):464-76.
Khare et al. The PYRIN domain-only protein POP3 inhibits ALR inflammasomes and regulates responses to infection with DNA viruses. Nat Immunol. Apr. 2014;15(4):343-53.
Le et al. Pyrin- and CARD-only Proteins as Regulators of NLR Functions. Front Immunol. Sep. 17, 2013;4:275.
Lu et al. Unified polymerization mechanism for the assembly of ASC-dependent inflammasomes. Cell. Mar. 13, 2014;156(6):1193-206.
Ludlow et al. The HIN-200 family: more than interferon-inducible genes? The HIN-200 family: more than interferon-inducible genes?
Mariathasan et al. Cryopyrin activates the inflammasome in response to toxins and ATP. Nature. Mar. 9, 2006;440(7081):228-32.
Mariathasan et al. Differential activation of the inflammasome by caspase-1 adaptors ASC and Ipaf. Nature. Jul. 8, 2004;430(6996):213-8.
Martinon et al. Gout-associated uric acid crystals activate the NALP3 inflammasome. Nature. Mar. 9, 2006;440(7081):237-41.
McDonald et al. Intravascular danger signals guide neutrophils to sites of sterile inflammation. Science. Oct. 15, 2010;330(6002):362-6.
Meng et al. A mutation in the Nlrp3 gene causing inflammasome hyperactivation potentiates Th17 cell-dominant immune responses. Immunity. Jun. 19, 2009;30(6):860-74.
Miao EA, et al. Cytoplasmic flagellin activates caspase-1 and secretion of interleukin 1beta via Ipaf. Nat Immunol. Jun. 2006;7(6):569-75.
Rathinam et al. The AIM2 inflammasome is essential for host defense against cytosolic bacteria and DNA viruses. Nat Immunol. 2010;11:395-402.
Roberts et al. HIN-200 proteins regulate caspase activation in response to foreign cytoplasmic DNA. Science. Feb. 20, 2009;323(5917):1057-60.
Schattgen & Fitzgerald. The PYHIN protein family as mediators of host defenses. Immunol Rev. Sep. 2011;243(1):109-18.
Scheibel et al.IkappaBbeta is an essential co-activator for LPS-induced IL-1beta transcription in vivo. J Exp Med. Nov. 22, 2010;207(12):2621-30.
Schroder et al. Acute lipopolysaccharide priming boosts inflammasome activation independently of inflammasome sensor induction. Immunobiology. Dec. 2012;217(12):1325-9.
Sciacca et al. Induction of IL-1 receptor antagonist by interferon beta: implication for the treatment of multiple sclerosis. J Neurovirol. May 2000;6 Suppl 2:S33-7.
Stehlik & Dorfleutner. COPs and POPs: modulators of inflammasome activity. J Immunol. Dec. 15, 2007;179(12):7993-8.
Stehlik et al. Apoptosis-associated speck-like protein containing a caspase recruitment domain is a regulator of procaspase-1 activation. J Immunol. Dec. 1, 2003;171(11):6154-63.
Stehlik et al. The PAAD/PYRIN-only protein POP1/ASC2 is a modulator of ASC-mediated nuclear-factor-kappa B and pro-caspase-1 regulation. Biochem J. Jul. 1, 2003;373(Pt 1):101-13.
Strowig et al. Inflammasomes in health and disease. Nature. Jan. 18, 2012;481(7381):278-86.
Tang et al. Gene-expression profiling of gram-positive and gram-negative sepsis in critically ill patients. Crit Care Med. Apr. 2008;36(4):1125-8.
Tivol et al. Emergent autoimmunity in graft-versus-host disease. Blood. Jun. 15, 2005;105(12):4885-91.
Unterholzner et al. IFI16 is an innate immune sensor for intracellular DNA. Nat Immunol. Nov. 2010;11(11):997-1004.
Vajjhala et al. Multiple binding sites on the pyrin domain of ASC protein allow self-association and interaction with NLRP3 protein. J Biol Chem. Dec. 7, 2012;287(50):41732-43.
Wang et al. HMG-1 as a late mediator of endotoxin lethality in mice. Science. Jul. 9, 1999;285(5425):248-51.
Wong et al. Genomic expression profiling across the pediatric systemic inflammatory response syndrome, sepsis, and septic shock spectrum. Crit Care Med. May 2009;37(5):1558-66.
Yampolsky et al., The exchangeability of amino acids in proteins. Genetics. Aug. 2005;170(4):1459-72.
Yang et al. The cytosolic nucleic acid sensor LRRFIP1 mediates the production of type I interferon via a beta-catenin-dependent pathway. Nat Immunol. Jun. 2010;11(6):487-94.

(56) References Cited

OTHER PUBLICATIONS

International Search Report and Written Opinion for PCT/US2015/015761 dated Jun. 21, 2015, 16 pages.

\* cited by examiner

Fig. 1b

```
        10         20         30         40         50         60         70         80         90
ATGGAGAGTA AATATAAGGA GATACTCTTG CTAACCAGCC TGGATAACAT CACCGATGAG GAACTGGATA GGTTTAAGTG CTTTCTTCCA
       100        110        120        130        140        150        160        170        180
GATGAGTTTA ATATTGCCAC AGGCAAACTG CATACTCTAA ACAGCACGAG TAGCCAACTT GATTTAAAAC GCTGGCATGG TGTCTGCAGT
       190        200        210        220        230        240        250        260        270
GAGGAAGACC GTATTTTTCA GAAGCTGAAT TATATGCTTG TGGCAAAATG TCTTCGGGAA GAGCAGGAAA CAGGTATATG TGGGAGTCCC
       280        290        300        310        320        330        340
TCATCTGCCC GGTCCGTTTC TCAGTCAAGA CTTGGTCTTT CCTTTCATGG CATTTCTGGG AATGCATGTT GA
```

Fig. 2a

MESKYKEILLLTSLDNITTDEELDRFKCFLPDEFNIATGKLHTLNSTSSQLDLKRWHGVCSEEDRIFQKLNYMLVAKCLREEQETGICGSPSSARSVSQSRGLSFHGISGNAC

Fig.3a

| | | | | |
|---|---|---|---|---|
| POP3-PYD | 1 | MESKYKEILLLTSLDNITDEELDRFKCFLPDEFNIATGKLHTLNSTSSQL | 50 | SEQ ID NO: 27 |
| AIM2-PYD | 1 | MESKYKEILLLTGLDNITDEELDRFKFFLSDEFNIATGKLHTANRIQVAT | 50 | SEQ ID NO: 28 |
| IFI-16-PYD | 1 | MGKKYKNIVLLKGLEVINDYHERMVKSLLSNDLKNLKMREEYDKIQIAD | 50 | SEQ ID NO: 29 |
| MNDA-PYD | 1 | MVNEYKKILLLKGFELMDDYHFTSIKSLLAYDGLTTKMQEEYNRIKITD | 50 | SEQ ID NO: 30 |
| IFIX-PYD | 1 | MANNYKKIVLLKGLEVINDYHERIVKSLLSNDLKLNPKMKEEYDKIQIAD | 50 | SEQ ID NO: 31 |

| | | | | |
|---|---|---|---|---|
| POP3-PYD | 51 | DLKRWHGVCSEED--RIFQKLN-YMLVAKCLREEQETGI-CGSPSSARSV | 96 | SEQ ID NO: 27 |
| AIM2-PYD | 51 | LMIQNAGAVSAVMKTIRIEQKLN-YMLLAKRLQEEKEK---VDKQYKSV | 95 | SEQ ID NO: 28 |
| IFI-16-PYD | 51 | LNEEKFRGDAGLGKLIKIFEDIPTLEDLAETLKKEKLKVKGP------ | 92 | SEQ ID NO: 29 |
| MNDA-PYD | 51 | LNEEKFQGVACLDKLIELAKDMPSLKNLVNNLRKEKSKVAKKIKTQEKA- | 99 | SEQ ID NO: 30 |
| IFIX-PYD | 51 | LNEEKFPGDAGLGKLIEFFKEIPTLGDLAETLKREKLKVKGIIPSKKTK- | 99 | SEQ ID NO: 31 |

FIG. 4a  FIG. 4b
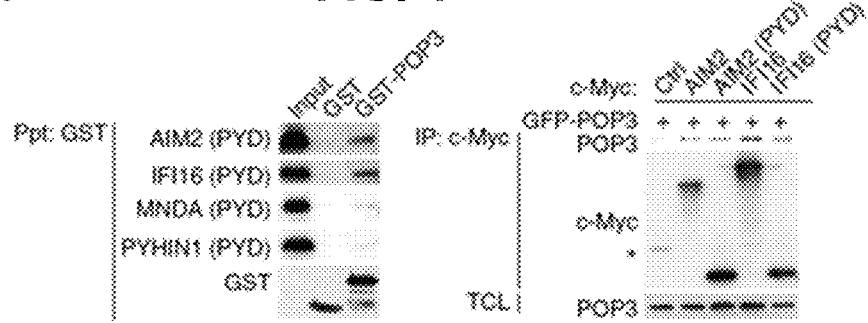
FIG. 4g  FIG. 4h
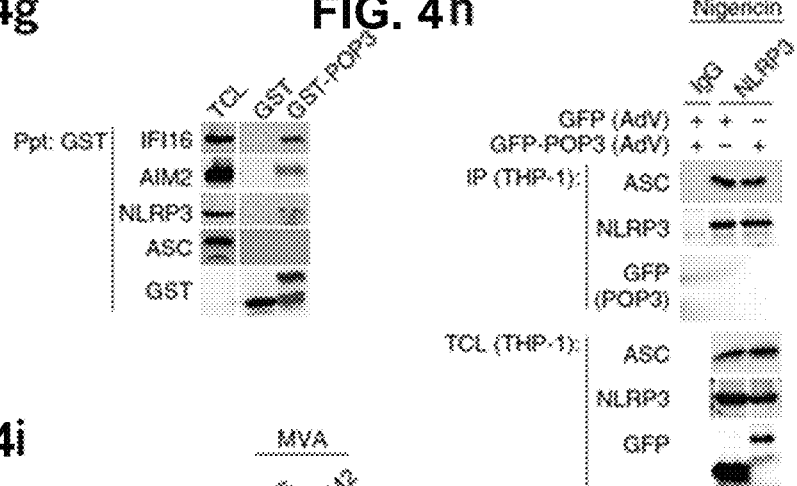
FIG. 4i
FIG. 4j
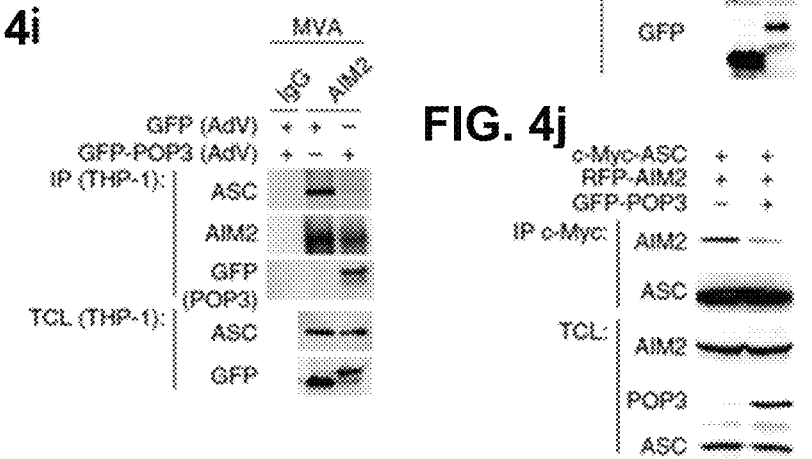
FIG. 4k
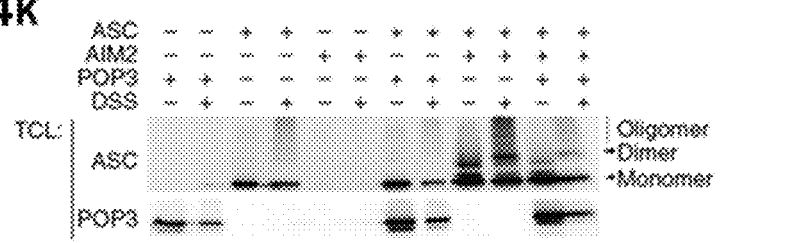

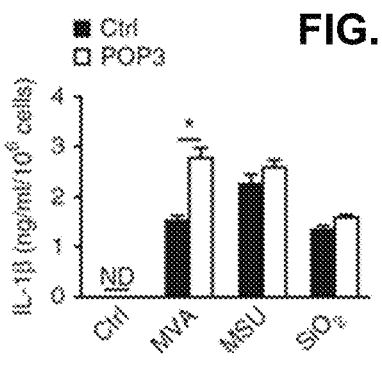
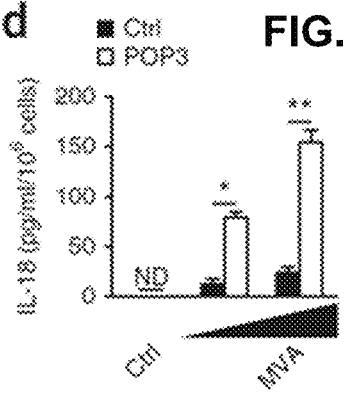
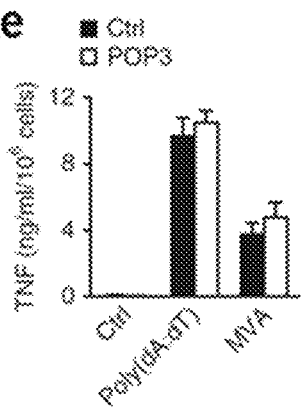
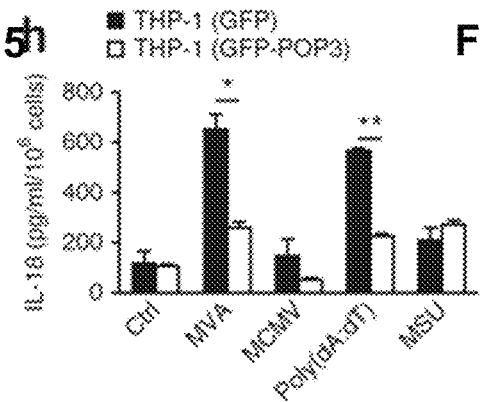
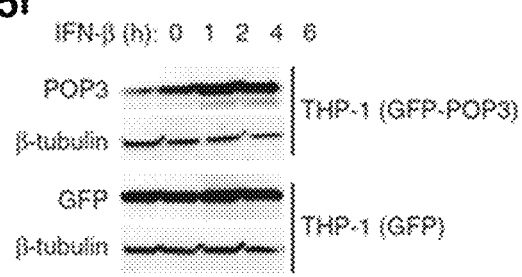
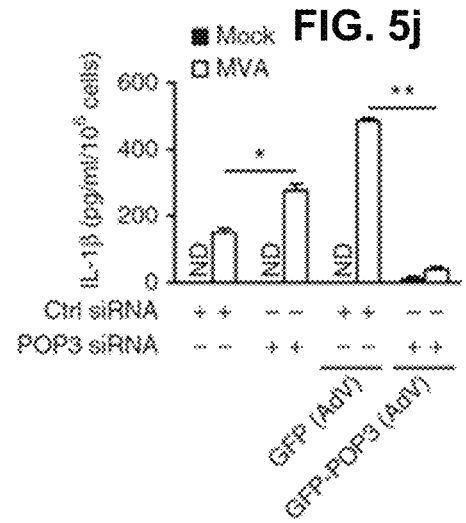
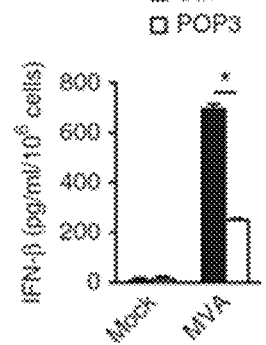

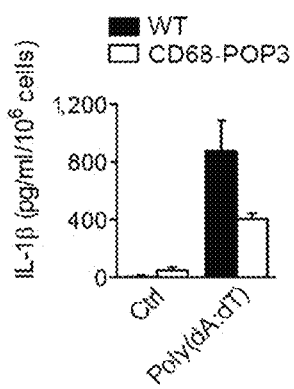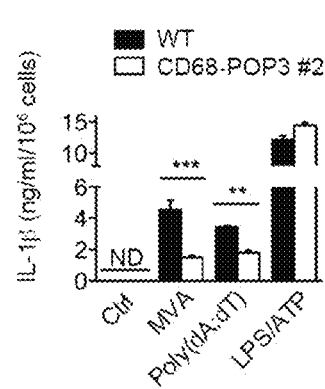
FIG. 10a  FIG. 10b  FIG. 10c
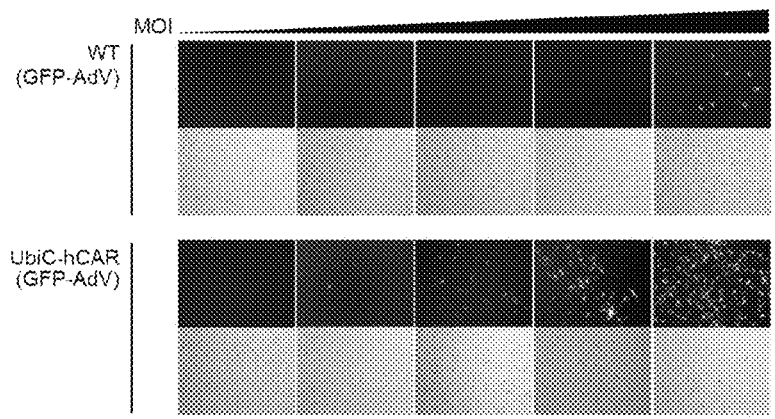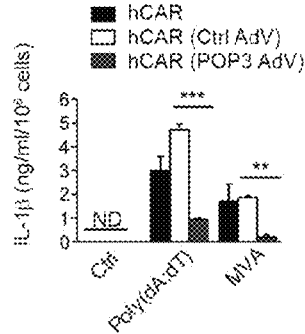
FIG. 10d  FIG. 10e
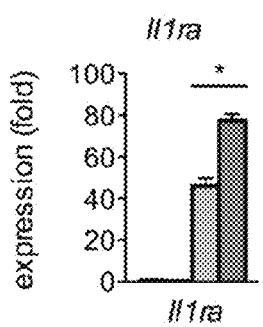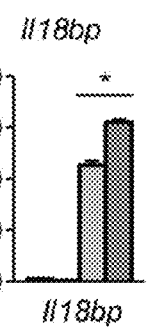
FIG. 10f

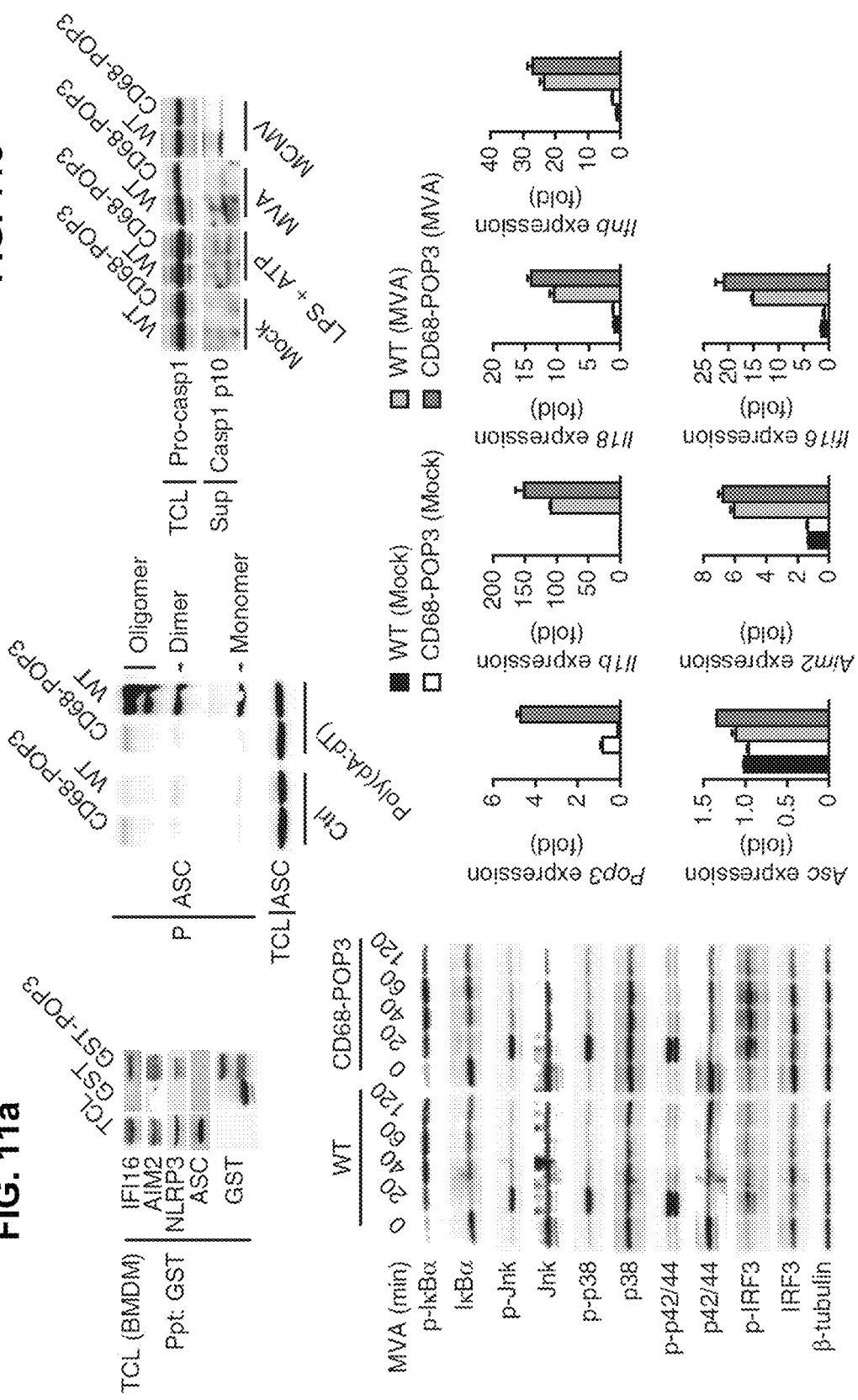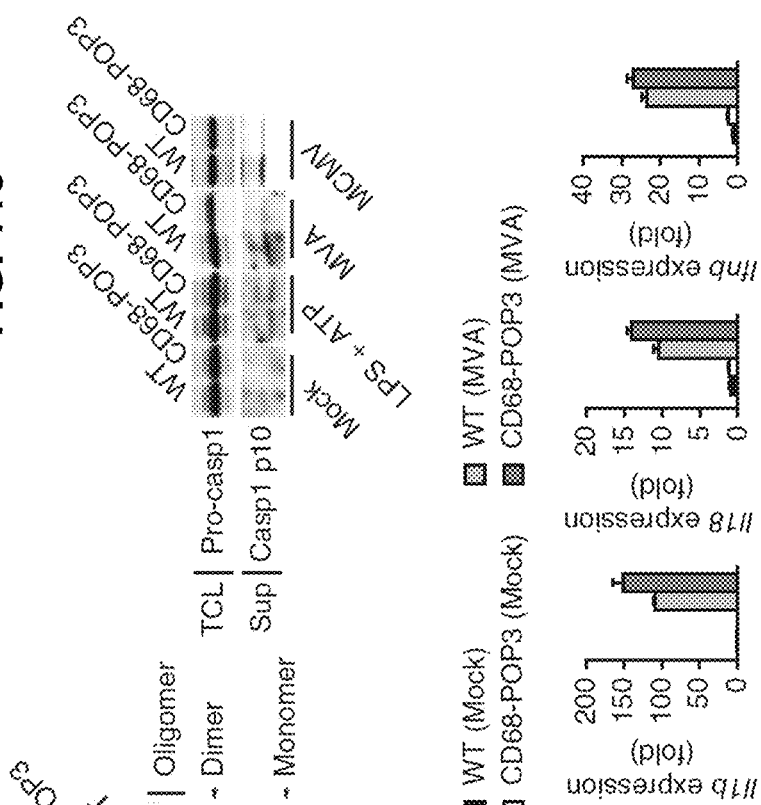

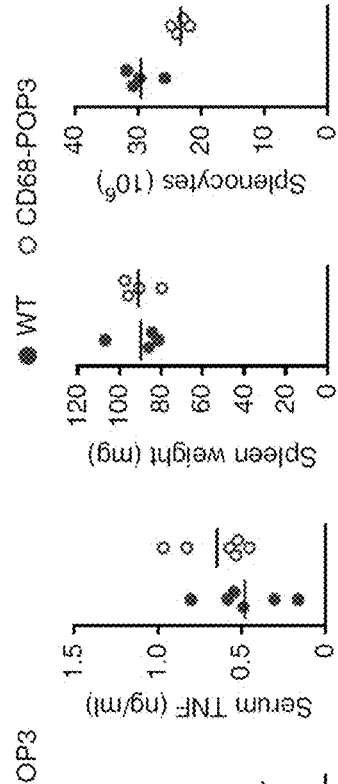
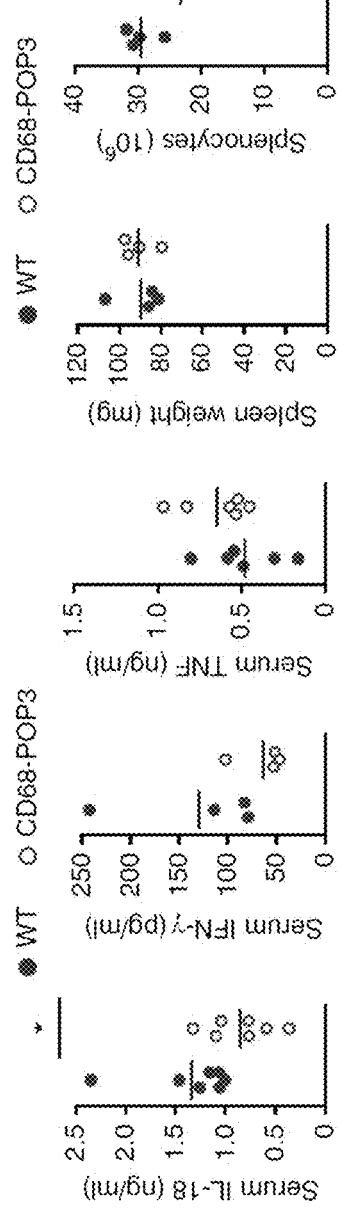
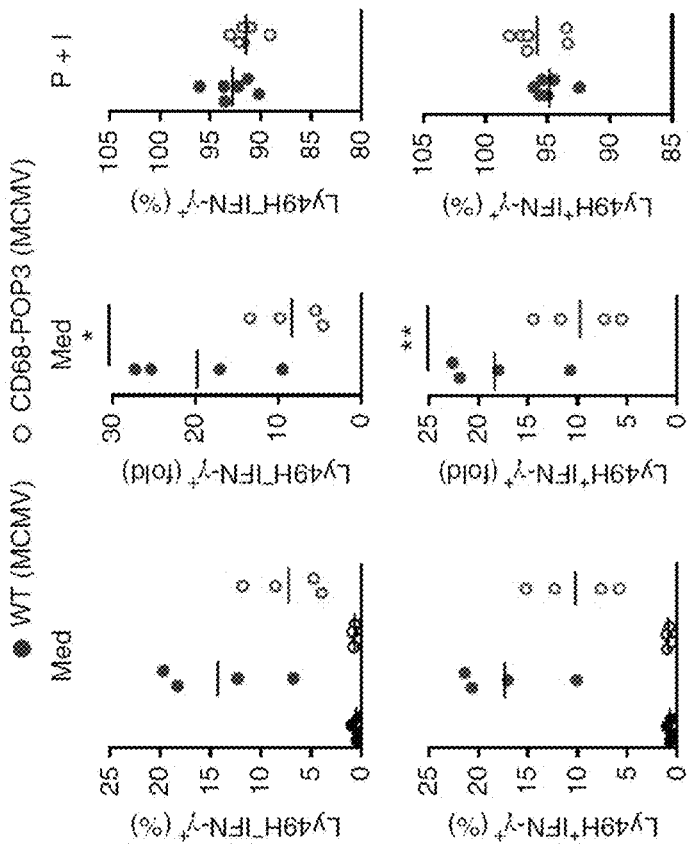
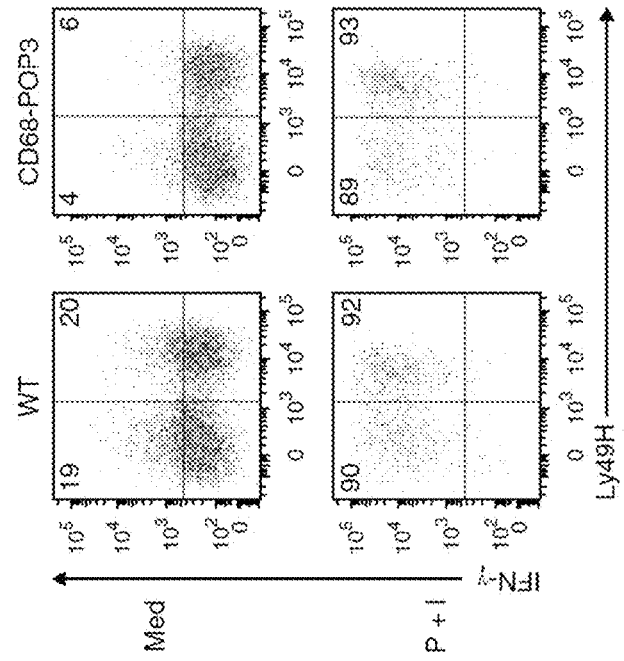

FIG. 12c
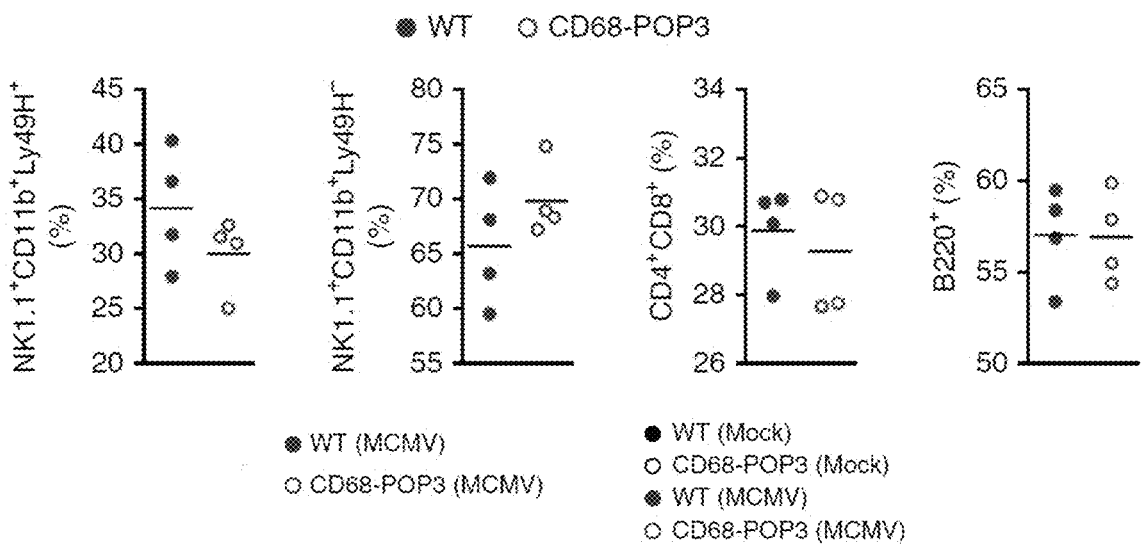
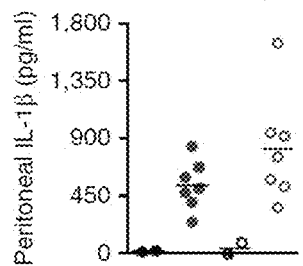
FIG. 12h
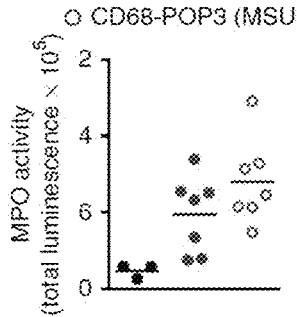
FIG. 12i

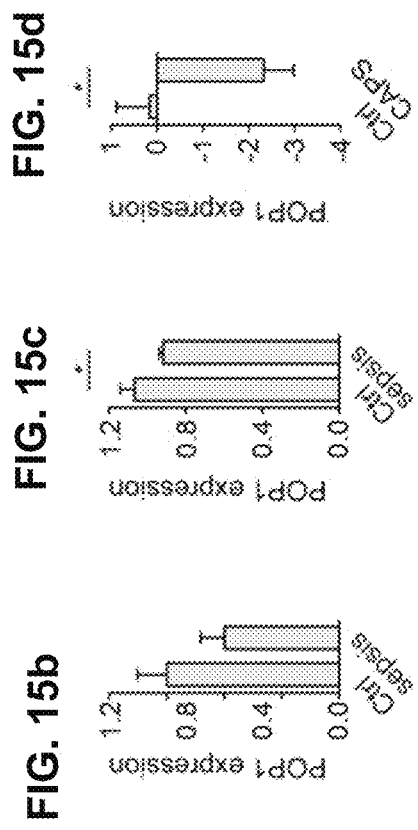
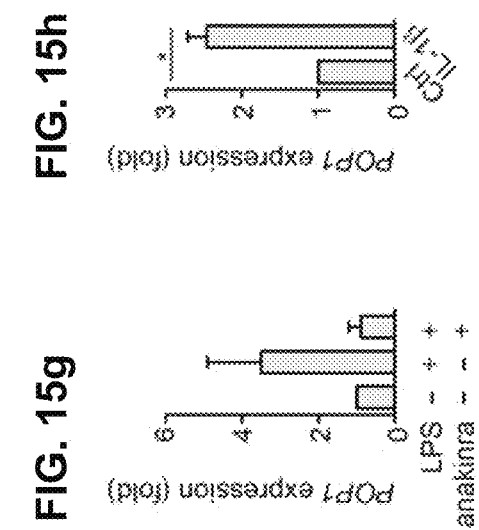
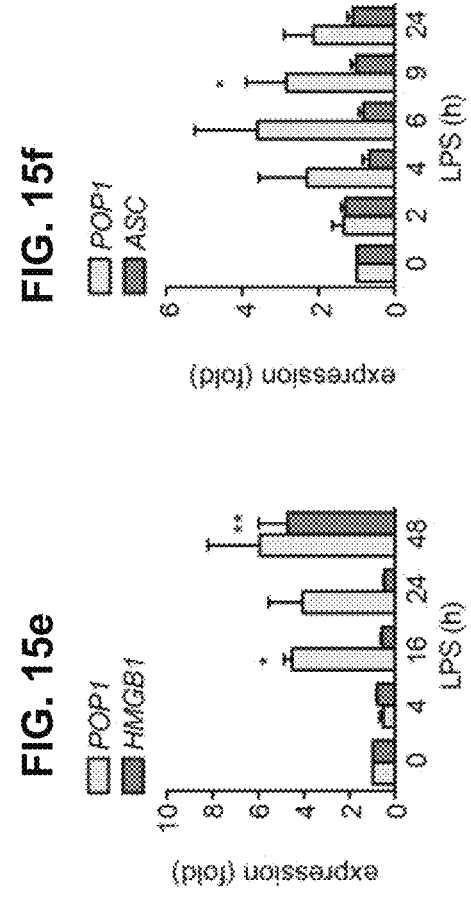

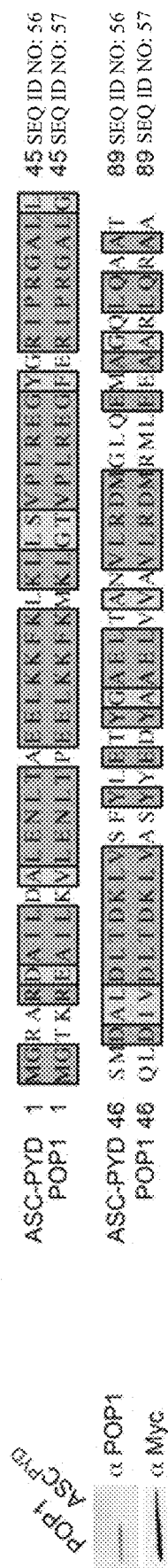
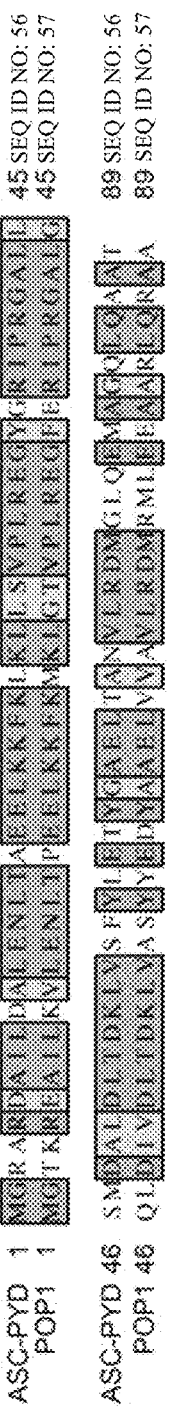
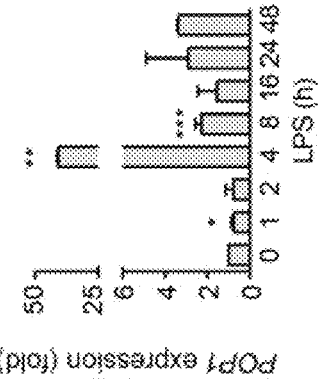
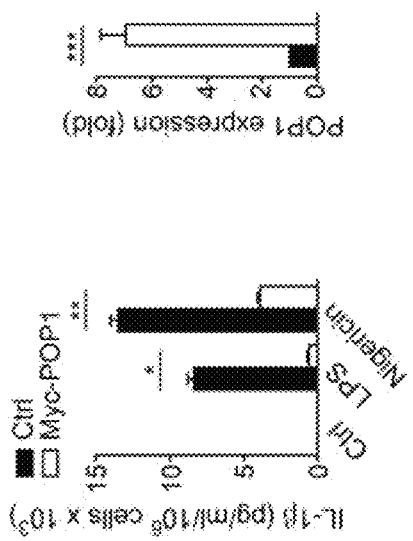
FIG. 16a
FIG. 16b
FIG. 16c
FIG. 16d

FIG. 17b 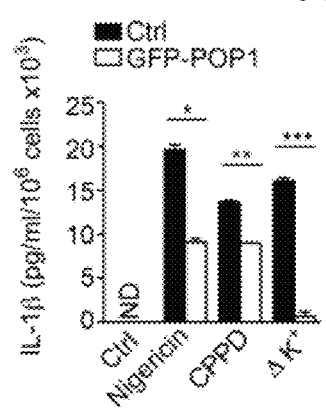 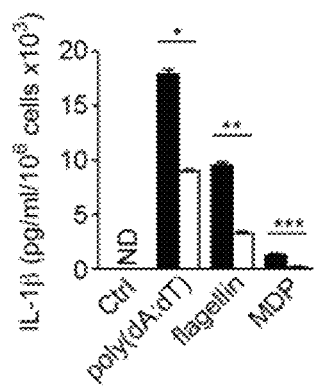

FIG. 17f 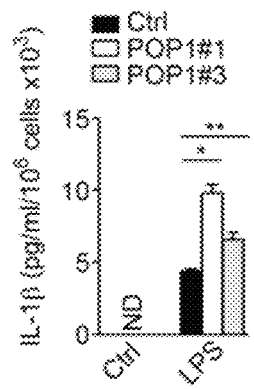 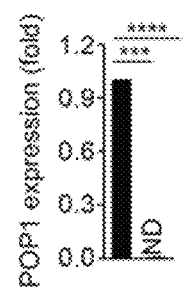

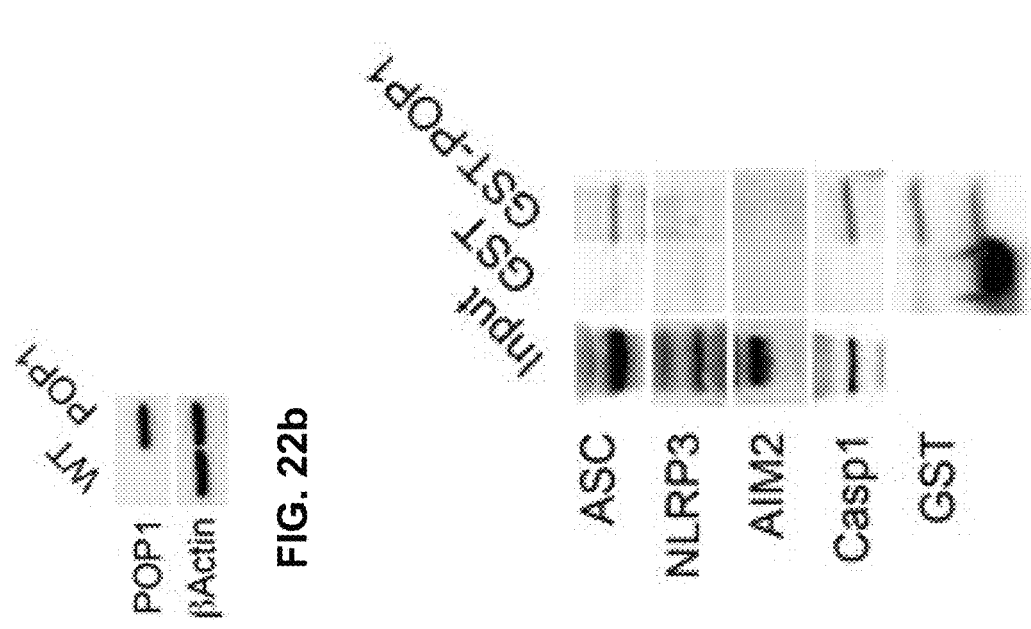
FIG. 22b
FIG. 22c
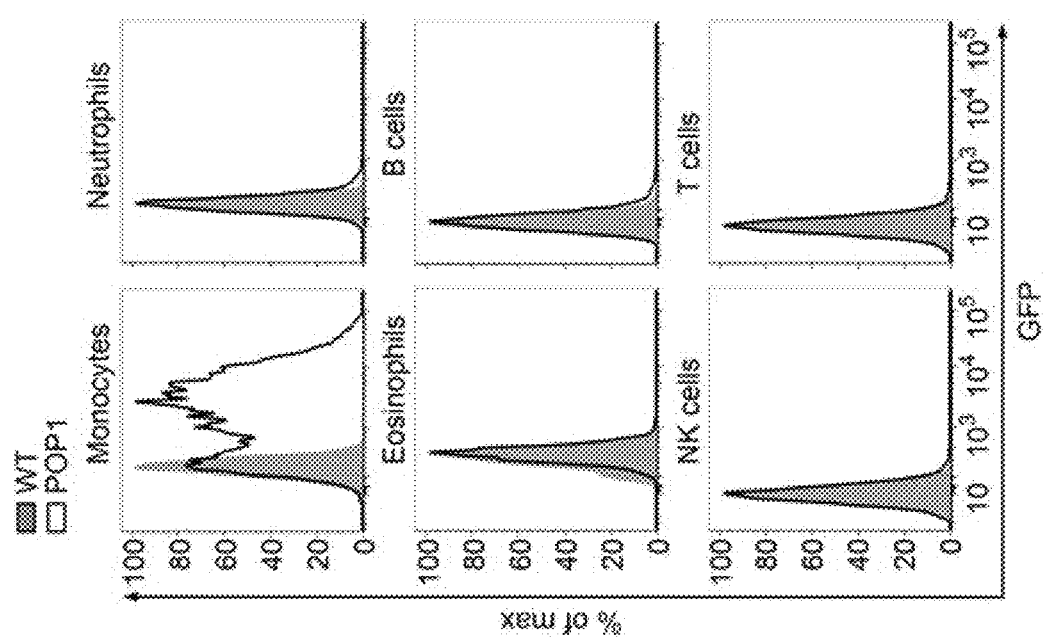
FIG. 22a

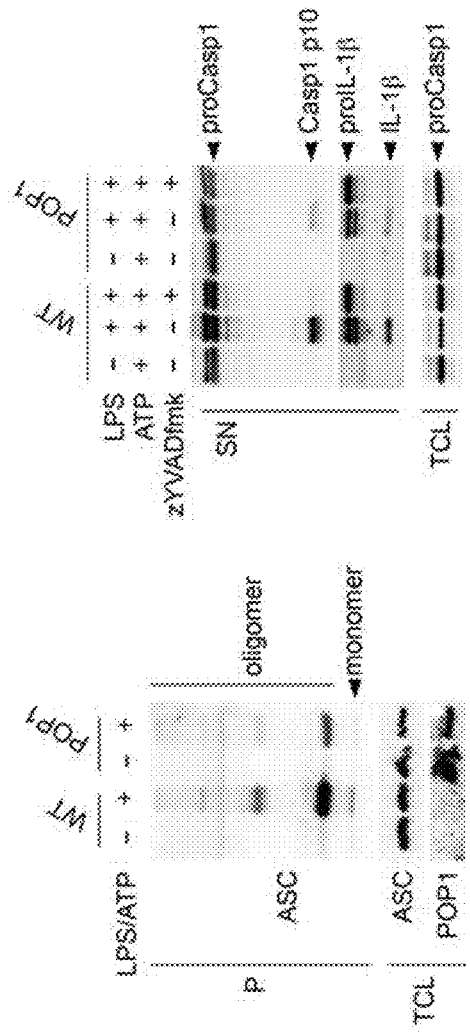

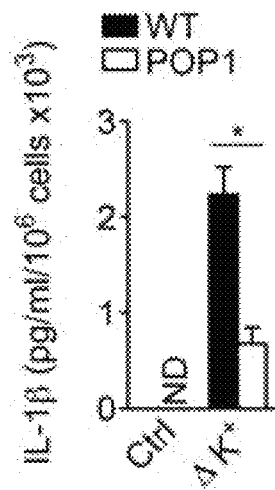
FIG. 24c
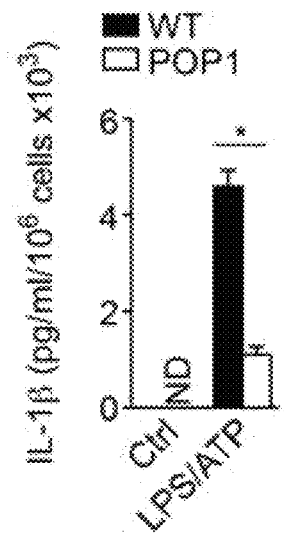
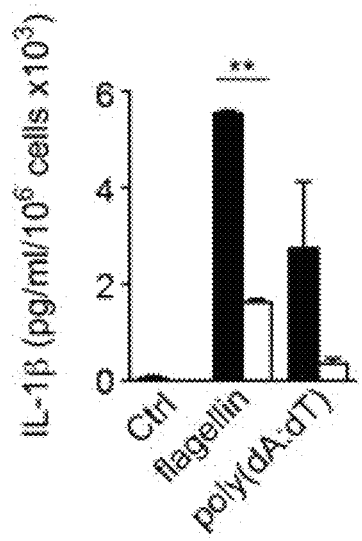
FIG. 24d
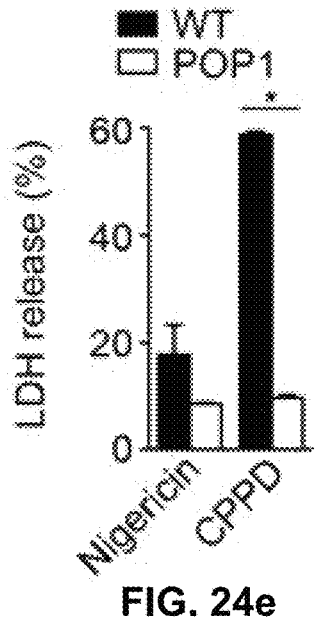
FIG. 24e

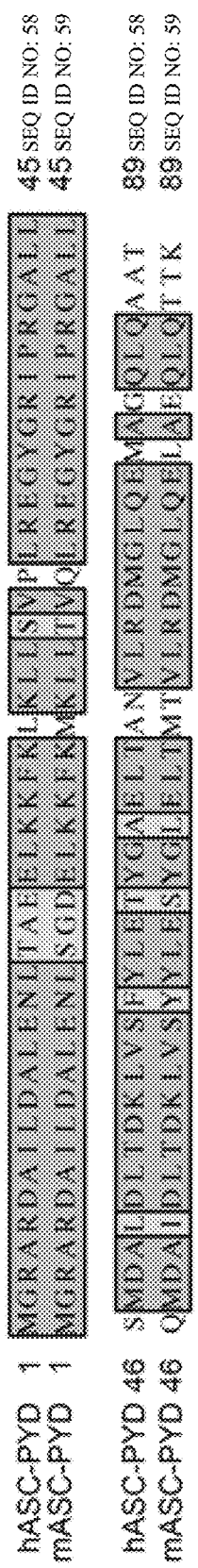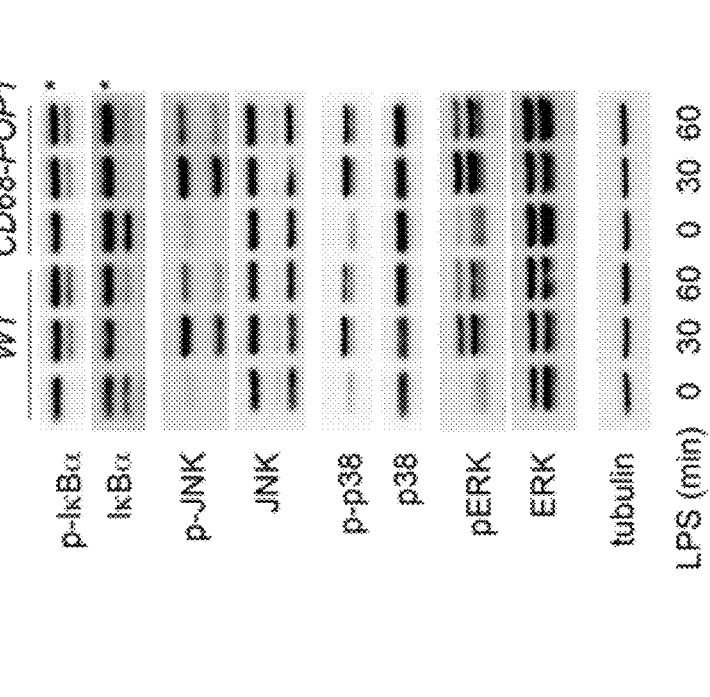
FIG. 25a
FIG. 25b
FIG. 25c

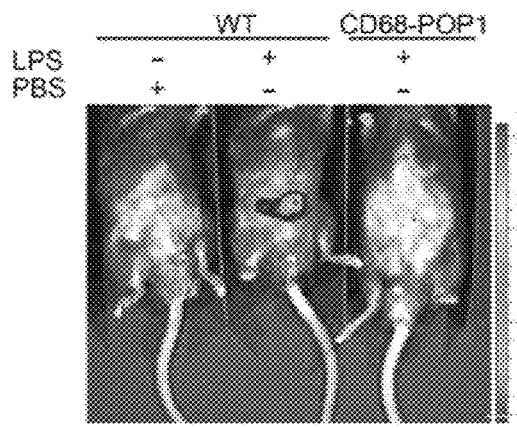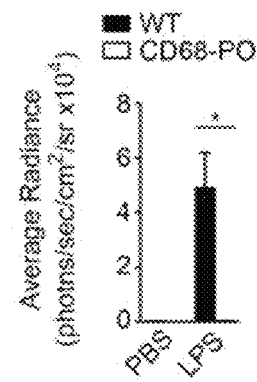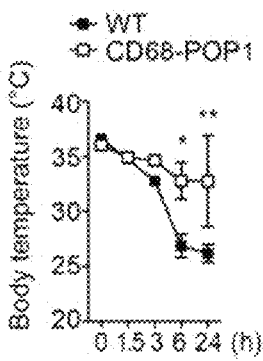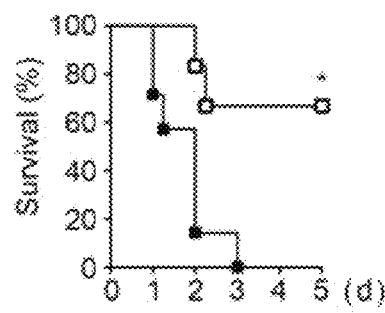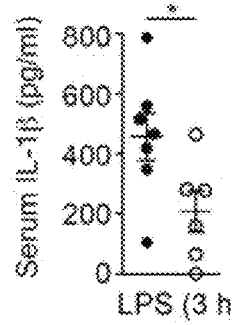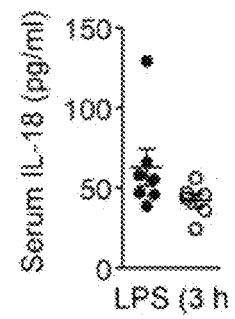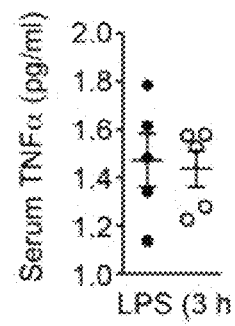
FIG. 26a
FIG. 26b
FIG. 26c
FIG. 26d

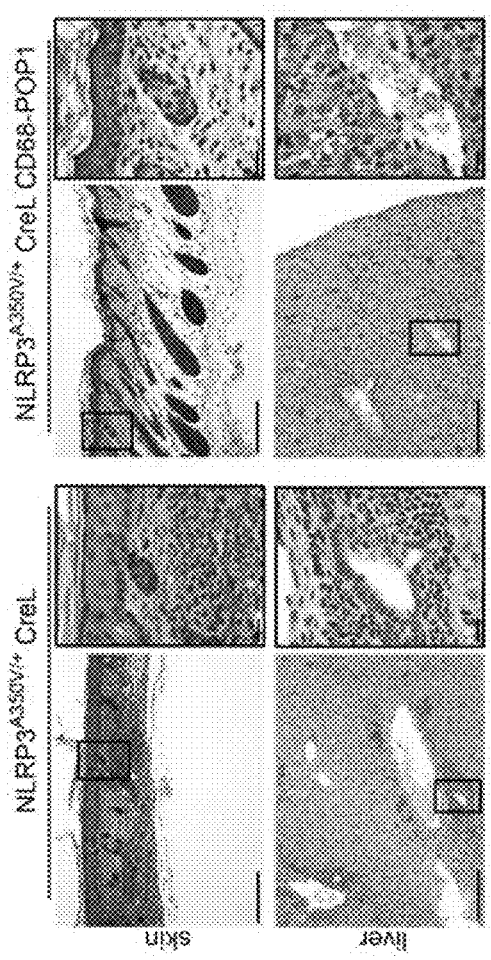
FIG. 26e
FIG. 26f
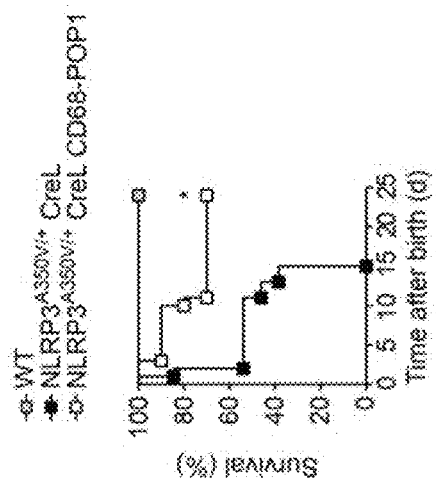
FIG. 26g
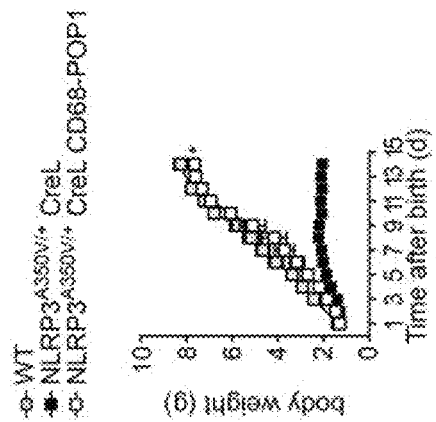
FIG. 26h
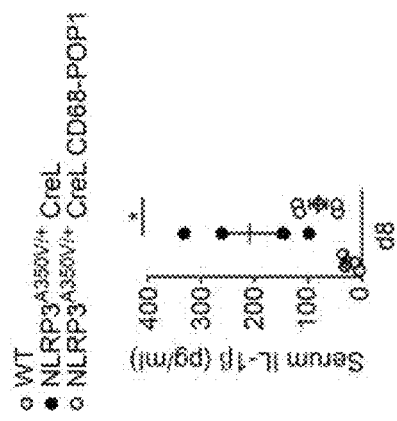
FIG. 26i FIG. 34a  FIG. 34b
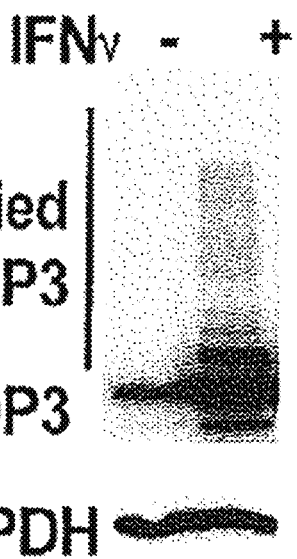
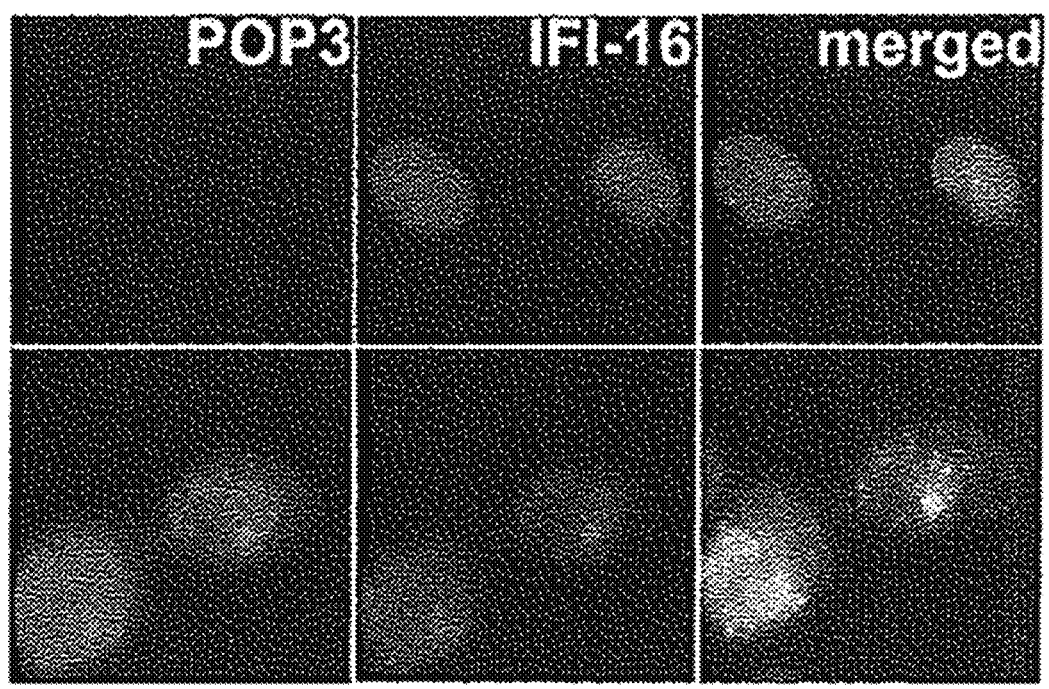
FIG. 35

SEQUENCE LISTING

<160> NUMBER OF SEQ ID NOS: 63

<210> SEQ ID NO 1
<211> LENGTH: 25
<212> TYPE: RNA
<213> ORGANISM: Artificial sequence
<220> FEATURE:
<223> OTHER INFORMATION: Synthetic

<400> SEQUENCE: 1
cauggcauuu cugggaaugc auguu                                          25

<210> SEQ ID NO 2
<211> LENGTH: 24
<212> TYPE: RNA
<213> ORGANISM: Artificial sequence
<220> FEATURE:
<223> OTHER INFORMATION: Synthetic

<400> SEQUENCE: 2
gagcaggaaa cgguauaugu ggga                                           24

<210> SEQ ID NO 3
<211> LENGTH: 22
<212> TYPE: DNA
<213> ORGANISM: Artificial sequence
<220> FEATURE:
<223> OTHER INFORMATION: Synthetic

<400> SEQUENCE: 3
agcacgagta gccaacttga tt                                             22

<210> SEQ ID NO 4
<211> LENGTH: 20
<212> TYPE: DNA
<213> ORGANISM: Artificial sequence
<220> FEATURE:
<223> OTHER INFORMATION: Synthetic

<400> SEQUENCE: 4
ggtcttcctc actgcagaca                                                20

<210> SEQ ID NO 5
<211> LENGTH: 16
<212> TYPE: DNA
<213> ORGANISM: Artificial sequence
<220> FEATURE:
<223> OTHER INFORMATION: Synthetic

<400> SEQUENCE: 5
ccatgccagc gtttta                                                    16

<210> SEQ ID NO 6
<211> LENGTH: 21
<212> TYPE: DNA
<213> ORGANISM: Artificial sequence
<220> FEATURE:
<223> OTHER INFORMATION: Synthetic

<400> SEQUENCE: 6
atggagagta aatataagga g                                              21

<210> SEQ ID NO 7
<211> LENGTH: 21
<212> TYPE: DNA
<213> ORGANISM: Artificial sequence
<220> FEATURE:
<223> OTHER INFORMATION: Synthetic

<400> SEQUENCE: 7
tcaacatgca ttcccagaaa t                                              21

<210> SEQ ID NO 8
<211> LENGTH: 59
<212> TYPE: DNA
<213> ORGANISM: Artificial sequence

```
<220> FEATURE:
<223> OTHER INFORMATION: Synthetic

<400> SEQUENCE: 8
ccggtcctac tacgaggact acgcactcga gtgcgtagtc ctcgtagtag gattttttg      59

<210> SEQ ID NO 9
<211> LENGTH: 59
<212> TYPE: DNA
<213> ORGANISM: Artificial sequence
<220> FEATURE:
<223> OTHER INFORMATION: Synthetic

<400> SEQUENCE: 9
ccggacaagc tggtcgcctc ctactctcga gagtaggagg cgaccagctt gttttttg       59

<210> SEQ ID NO 10
<211> LENGTH: 11
<212> TYPE: PRT
<213> ORGANISM: Artificial sequence
<220> FEATURE:
<223> OTHER INFORMATION: Synthetic

<400> SEQUENCE: 10
```

Tyr Gly Arg Lys Lys Arg Arg Gln Arg Arg Arg
1               5                  10

```
<210> SEQ ID NO 11
<211> LENGTH: 89
<212> TYPE: PRT
<213> ORGANISM: Homo sapiens

<400> SEQUENCE: 11
```

Met Gly Thr Lys Arg Glu Ala Ile Leu Lys Val Leu Glu Asn Leu Thr
1               5                  10                  15

Pro Glu Glu Leu Lys Lys Phe Lys Met Lys Leu Gly Thr Val Pro Leu
                20                  25                  30

Arg Glu Gly Phe Glu Arg Ile Pro Arg Gly Ala Leu Gly Gln Leu Asp
            35                  40                  45

Ile Val Asp Leu Thr Asp Lys Leu Val Ala Ser Tyr Tyr Glu Asp Tyr
        50                  55                  60

Ala Ala Glu Leu Val Val Ala Val Leu Arg Asp Met Arg Met Leu Glu
65                  70                  75                  80

Glu Ala Ala Arg Leu Gln Arg Ala Ala
                85

```
<210> SEQ ID NO 12
<211> LENGTH: 90
<212> TYPE: PRT
<213> ORGANISM: Homo sapiens

<400> SEQUENCE: 12
```

Met Ala Ser Ser Ala Glu Leu Asp Phe Asn Leu Gln Ala Leu Leu Glu
1               5                  10                  15

Gln Leu Ser Gln Asp Glu Leu Ser Lys Phe Lys Ser Leu Ile Arg Thr
                20                  25                  30

Ile Ser Leu Gly Lys Glu Leu Gln Thr Val Pro Gln Thr Glu Val Asp
            35                  40                  45

Lys Ala Asn Gly Lys Gln Leu Val Glu Ile Phe Thr Ser His Ser Cys
        50                  55                  60

Ser Tyr Trp Ala Gly Met Ala Ala Ile Gln Val Phe Glu Lys Met Asn

```
                65                  70                  75                  80
Gln Thr His Leu Ser Gly Arg Ala Asp Glu
                85                  90

<210> SEQ ID NO 13
<211> LENGTH: 89
<212> TYPE: PRT
<213> ORGANISM: Homo sapiens

<400> SEQUENCE: 13

Met Glu Ser Lys Tyr Lys Glu Ile Leu Leu Leu Thr Ser Leu Asp Asn
1               5                   10                  15

Ile Thr Asp Glu Glu Leu Asp Arg Phe Lys Cys Phe Leu Pro Asp Glu
                20                  25                  30

Phe Asn Ile Ala Thr Gly Lys Leu His Thr Leu Asn Ser Thr Ser Ser
            35                  40                  45

Gln Leu Asp Leu Lys Arg Trp His Gly Val Cys Ser Glu Glu Asp Arg
        50                  55                  60

Ile Phe Gln Lys Leu Asn Tyr Met Leu Val Ala Lys Cys Leu Arg Glu
65                  70                  75                  80

Glu Gln Glu Thr Gly Ile Cys Gly Ser
                85

<210> SEQ ID NO 14
<211> LENGTH: 90
<212> TYPE: PRT
<213> ORGANISM: Homo sapiens

<400> SEQUENCE: 14

Met Glu Ser Lys Tyr Lys Glu Ile Leu Leu Leu Thr Gly Leu Asp Asn
1               5                   10                  15

Ile Thr Asp Glu Glu Leu Asp Arg Phe Lys Phe Phe Leu Ser Asp Glu
                20                  25                  30

Phe Asn Ile Ala Thr Gly Lys Leu His Thr Ala Asn Arg Ile Gln Val
            35                  40                  45

Ala Thr Leu Met Ile Gln Asn Ala Gly Ala Val Ser Ala Val Met Lys
        50                  55                  60

Thr Ile Arg Ile Phe Gln Lys Leu Asn Tyr Met Leu Leu Ala Lys Arg
65                  70                  75                  80

Leu Gln Glu Glu Lys Glu Lys Val Asp Lys
                85                  90

<210> SEQ ID NO 15
<211> LENGTH: 90
<212> TYPE: PRT
<213> ORGANISM: Homo sapiens

<400> SEQUENCE: 15

Met Glu Ser Glu Tyr Arg Glu Met Leu Leu Leu Thr Gly Leu Asp His
1               5                   10                  15

Ile Thr Glu Glu Glu Leu Lys Arg Phe Lys Tyr Phe Ala Leu Thr Glu
                20                  25                  30

Phe Gln Ile Ala Arg Ser Thr Leu Asp Val Ala Asp Arg Thr Glu Leu
            35                  40                  45

Ala Asp His Leu Ile Gln Ser Ala Gly Ala Ser Ala Val Thr Lys
        50                  55                  60

Ala Ile Asn Ile Phe Gln Lys Leu Asn Tyr Met His Ile Ala Asn Ala
65                  70                  75                  80
```

-continued

Leu Glu Glu Lys Lys Lys Glu Ala Ser Glu
                85              90

<210> SEQ ID NO 16
<211> LENGTH: 89
<212> TYPE: PRT
<213> ORGANISM: Homo sapiens

<400> SEQUENCE: 16

Met Glu Ser Lys Tyr Lys Glu Ile Leu Leu Thr Ser Leu Asp Asn
1               5                   10                  15

Ile Thr Asp Glu Glu Leu Asp Arg Phe Lys Cys Phe Leu Pro Asp Glu
                20                  25                  30

Phe Asn Ile Ala Thr Gly Lys Leu His Thr Leu Asn Ser Thr Ser Ser
            35                  40                  45

Gln Leu Asp Leu Lys Arg Trp His Gly Val Cys Ser Glu Glu Asp Arg
        50                  55                  60

Ile Phe Gln Lys Leu Asn Tyr Met Leu Val Ala Lys Cys Leu Arg Glu
65                  70                  75                  80

Glu Gln Glu Thr Gly Ile Cys Gly Ser
                85

<210> SEQ ID NO 17
<211> LENGTH: 92
<212> TYPE: PRT
<213> ORGANISM: Homo sapiens

<400> SEQUENCE: 17

Met Gly Lys Lys Tyr Lys Asn Ile Val Leu Leu Lys Gly Leu Glu Val
1               5                   10                  15

Ile Asn Asp Tyr His Phe Arg Met Val Lys Ser Leu Leu Ser Asn Asp
                20                  25                  30

Leu Lys Leu Asn Leu Lys Met Arg Glu Glu Tyr Asp Lys Ile Gln Ile
            35                  40                  45

Ala Asp Leu Met Glu Glu Lys Phe Arg Gly Asp Ala Gly Leu Gly Lys
        50                  55                  60

Leu Ile Lys Ile Phe Glu Asp Ile Pro Thr Leu Glu Asp Leu Ala Glu
65                  70                  75                  80

Thr Leu Lys Lys Glu Lys Leu Lys Val Lys Gly Pro
                85                  90

<210> SEQ ID NO 18
<211> LENGTH: 92
<212> TYPE: PRT
<213> ORGANISM: Homo sapiens

<400> SEQUENCE: 18

Met Val Asn Glu Tyr Lys Arg Ile Val Leu Leu Arg Gly Leu Glu Cys
1               5                   10                  15

Ile Asn Lys His Tyr Phe Ser Leu Phe Lys Ser Leu Leu Ala Arg Asp
                20                  25                  30

Leu Asn Leu Glu Arg Asp Asn Gln Glu Gln Tyr Thr Thr Ile Gln Ile
            35                  40                  45

Ala Asn Met Met Glu Glu Lys Phe Pro Ala Asp Ser Gly Leu Gly Lys
        50                  55                  60

Leu Ile Glu Phe Cys Glu Glu Val Pro Ala Leu Arg Lys Arg Ala Glu
65                  70                  75                  80

```
Ile Leu Lys Lys Glu Arg Ser Glu Val Thr Gly Glu
                85                  90
```

<210> SEQ ID NO 19
<211> LENGTH: 89
<212> TYPE: PRT
<213> ORGANISM: Homo sapiens

<400> SEQUENCE: 19

```
Met Glu Ser Lys Tyr Lys Glu Ile Leu Leu Thr Ser Leu Asp Asn
1               5                   10                  15

Ile Thr Asp Glu Glu Leu Asp Arg Phe Lys Cys Phe Leu Pro Asp Glu
                20                  25                  30

Phe Asn Ile Ala Thr Gly Lys Leu His Thr Leu Asn Ser Thr Ser Ser
            35                  40                  45

Gln Leu Asp Leu Lys Arg Trp His Gly Val Cys Ser Glu Glu Asp Arg
50                  55                  60

Ile Phe Gln Lys Leu Asn Tyr Met Leu Val Ala Lys Cys Leu Arg Glu
65                  70                  75                  80

Glu Gln Glu Thr Gly Ile Cys Gly Ser
                85
```

<210> SEQ ID NO 20
<211> LENGTH: 93
<212> TYPE: PRT
<213> ORGANISM: Homo sapiens

<400> SEQUENCE: 20

```
Met Gly Arg Ala Arg Asp Ala Ile Leu Asp Ala Leu Glu Asn Leu Ser
1               5                   10                  15

Gly Asp Glu Leu Lys Lys Phe Lys Met Lys Leu Leu Thr Val Gln Leu
                20                  25                  30

Arg Glu Gly Tyr Gly Arg Ile Pro Arg Gly Ala Leu Leu Gln Met Asp
            35                  40                  45

Ala Ile Asp Leu Thr Asp Lys Leu Val Ser Tyr Tyr Leu Glu Ser Tyr
50                  55                  60

Gly Leu Glu Leu Thr Met Thr Val Leu Arg Asp Met Gly Leu Gln Glu
65                  70                  75                  80

Leu Ala Glu Gln Leu Gln Thr Thr Lys Glu Glu Ser Gly
                85                  90
```

<210> SEQ ID NO 21
<211> LENGTH: 92
<212> TYPE: PRT
<213> ORGANISM: Homo sapiens

<400> SEQUENCE: 21

```
Met Gly Arg Ala Arg Asp Ala Ile Leu Asp Ala Leu Glu Asn Leu Thr
1               5                   10                  15

Ala Glu Glu Leu Lys Lys Phe Lys Leu Lys Leu Leu Ser Val Pro Leu
                20                  25                  30

Arg Glu Gly Tyr Gly Arg Ile Pro Arg Gly Ala Leu Leu Ser Met Asp
            35                  40                  45

Ala Leu Asp Leu Thr Asp Lys Leu Val Ser Phe Tyr Leu Glu Thr Tyr
50                  55                  60

Gly Ala Glu Leu Thr Ala Asn Val Leu Arg Asp Met Gly Leu Gln Glu
65                  70                  75                  80

Met Ala Gly Gln Leu Gln Ala Ala Thr His Gln Gly
```

<210> SEQ ID NO 22
<211> LENGTH: 89
<212> TYPE: PRT
<213> ORGANISM: Homo sapiens

<400> SEQUENCE: 22

Met Glu Ser Lys Tyr Lys Glu Ile Leu Leu Thr Ser Leu Asp Asn
1               5                   10                  15

Ile Thr Asp Glu Glu Leu Asp Arg Phe Lys Cys Phe Leu Pro Asp Glu
                20                  25                  30

Phe Asn Ile Ala Thr Gly Lys Leu His Thr Leu Asn Ser Thr Ser Ser
            35                  40                  45

Gln Leu Asp Leu Lys Arg Trp His Gly Val Cys Ser Glu Glu Asp Arg
    50                  55                  60

Ile Phe Gln Lys Leu Asn Tyr Met Leu Val Ala Lys Cys Leu Arg Glu
65                  70                  75                  80

Glu Gln Glu Thr Gly Ile Cys Gly Ser
                85

<210> SEQ ID NO 23
<211> LENGTH: 94
<212> TYPE: PRT
<213> ORGANISM: Homo sapiens

<400> SEQUENCE: 23

Met Thr Ser Val Arg Cys Lys Leu Ala Gln Tyr Leu Glu Asp Leu Glu
1               5                   10                  15

Asp Val Asp Leu Lys Lys Phe Lys Met His Leu Glu Asp Tyr Pro Pro
                20                  25                  30

Glu Lys Gly Cys Ile Pro Val Pro Arg Gly Gln Met Glu Lys Ala Asp
            35                  40                  45

His Leu Asp Leu Ala Thr Leu Met Ile Asp Phe Asn Gly Glu Glu Lys
    50                  55                  60

Ala Trp Ala Met Ala Val Trp Ile Phe Ala Ala Ile Asn Arg Arg Asp
65                  70                  75                  80

Leu Trp Glu Lys Ala Lys Lys Asp Gln Pro Glu Trp Asn Asp
                85                  90

<210> SEQ ID NO 24
<211> LENGTH: 93
<212> TYPE: PRT
<213> ORGANISM: Homo sapiens

<400> SEQUENCE: 24

Met Ala Ser Thr Arg Cys Lys Leu Ala Arg Tyr Leu Glu Asp Leu Glu
1               5                   10                  15

Asp Val Asp Leu Lys Lys Phe Lys Met His Leu Glu Asp Tyr Pro Pro
                20                  25                  30

Gln Lys Gly Cys Ile Pro Leu Pro Arg Gly Gln Thr Glu Lys Ala Asp
            35                  40                  45

His Val Asp Leu Ala Thr Leu Met Ile Asp Phe Asn Gly Glu Glu Lys
    50                  55                  60

Ala Trp Ala Met Ala Val Trp Ile Phe Ala Ala Ile Asn Arg Arg Asp
65                  70                  75                  80

Leu Tyr Glu Lys Ala Lys Arg Asp Glu Pro Lys Trp Gly
                85                  90

<210> SEQ ID NO 25
<211> LENGTH: 89
<212> TYPE: PRT
<213> ORGANISM: Homo sapiens

<400> SEQUENCE: 25

Met Glu Ser Lys Tyr Lys Glu Ile Leu Leu Leu Thr Ser Leu Asp Asn
1               5                   10                  15

Ile Thr Asp Glu Glu Leu Asp Arg Phe Lys Cys Phe Leu Pro Asp Glu
            20                  25                  30

Phe Asn Ile Ala Thr Gly Lys Leu His Thr Leu Asn Ser Thr Ser Ser
        35                  40                  45

Gln Leu Asp Leu Lys Arg Trp His Gly Val Cys Ser Glu Glu Asp Arg
    50                  55                  60

Ile Phe Gln Lys Leu Asn Tyr Met Leu Val Ala Lys Cys Leu Arg Glu
65                  70                  75                  80

Glu Gln Glu Thr Gly Ile Cys Gly Ser
                85

<210> SEQ ID NO 26
<211> LENGTH: 342
<212> TYPE: DNA
<213> ORGANISM: Homo sapiens

<400> SEQUENCE: 26
atggagagta atataagga gatactcttg ctaaccagcc tggataacat caccgatgag      60
gaactggata ggtttaagtg ctttcttcca gatgagttta atattgccac aggcaaactg     120
catactctaa acagcacgag tagccaactt gatttaaaac gctggcatgg tgtctgcagt     180
gaggaagacc gtattttca gaagctgaat tatatgcttg tggcaaaatg tcttcgggaa      240
gagcaggaaa caggtatatg tgggagtccc tcatctgccc ggtccgtttc tcagtcaaga     300
cttggtcttt cctttcatgg catttctggg aatgcatgtt ga                       342

<210> SEQ ID NO 27
<211> LENGTH: 96
<212> TYPE: PRT
<213> ORGANISM: Homo sapiens

<400> SEQUENCE: 27

Met Glu Ser Lys Tyr Lys Glu Ile Leu Leu Leu Thr Ser Leu Asp Asn
1               5                   10                  15

Ile Thr Asp Glu Glu Leu Asp Arg Phe Lys Cys Phe Leu Pro Asp Glu
            20                  25                  30

Phe Asn Ile Ala Thr Gly Lys Leu His Thr Leu Asn Ser Thr Ser Ser
        35                  40                  45

Gln Leu Asp Leu Lys Arg Trp His Gly Val Cys Ser Glu Glu Asp Arg
    50                  55                  60

Ile Phe Gln Lys Leu Asn Tyr Met Leu Val Ala Lys Cys Leu Arg Glu
65                  70                  75                  80

Glu Gln Glu Thr Gly Ile Cys Gly Ser Pro Ser Ser Ala Arg Ser Val
                85                  90                  95

<210> SEQ ID NO 28
<211> LENGTH: 95
<212> TYPE: PRT
<213> ORGANISM: Homo sapiens -continued

```
<400> SEQUENCE: 28

Met Glu Ser Lys Tyr Lys Glu Ile Leu Leu Thr Gly Leu Asp Asn
1               5                   10                  15

Ile Thr Asp Glu Glu Leu Asp Arg Phe Lys Phe Leu Ser Asp Glu
                20                  25                  30

Phe Asn Ile Ala Thr Gly Lys Leu His Thr Ala Asn Arg Ile Gln Val
                35                  40                  45

Ala Thr Leu Met Ile Gln Asn Ala Gly Ala Val Ser Ala Val Met Lys
                50                  55                  60

Thr Ile Arg Ile Phe Gln Lys Leu Asn Tyr Met Leu Leu Ala Lys Arg
65                  70                  75                  80

Leu Gln Glu Glu Lys Glu Lys Val Asp Lys Gln Tyr Lys Ser Val
                85                  90                  95

<210> SEQ ID NO 29
<211> LENGTH: 92
<212> TYPE: PRT
<213> ORGANISM: Homo sapiens

<400> SEQUENCE: 29

Met Gly Lys Lys Tyr Lys Asn Ile Val Leu Leu Lys Gly Leu Glu Val
1               5                   10                  15

Ile Asn Asp Tyr His Phe Arg Met Val Lys Ser Leu Leu Ser Asn Asp
                20                  25                  30

Leu Lys Leu Asn Leu Lys Met Arg Glu Glu Tyr Asp Lys Ile Gln Ile
                35                  40                  45

Ala Asp Leu Met Glu Glu Lys Phe Arg Gly Asp Ala Gly Leu Gly Lys
                50                  55                  60

Leu Ile Lys Ile Phe Glu Asp Ile Pro Thr Leu Glu Asp Leu Ala Glu
65                  70                  75                  80

Thr Leu Lys Lys Glu Lys Leu Lys Val Lys Gly Pro
                85                  90

<210> SEQ ID NO 30
<211> LENGTH: 99
<212> TYPE: PRT
<213> ORGANISM: Homo sapiens

<400> SEQUENCE: 30

Met Val Asn Glu Tyr Lys Lys Ile Leu Leu Leu Lys Gly Phe Glu Leu
1               5                   10                  15

Met Asp Asp Tyr His Phe Thr Ser Ile Lys Ser Leu Leu Ala Tyr Asp
                20                  25                  30

Leu Gly Leu Thr Thr Lys Met Gln Glu Glu Tyr Asn Arg Ile Lys Ile
                35                  40                  45

Thr Asp Leu Met Glu Lys Lys Phe Gln Gly Val Ala Cys Leu Asp Lys
                50                  55                  60

Leu Ile Glu Leu Ala Lys Asp Met Pro Ser Leu Lys Asn Leu Val Asn
65                  70                  75                  80

Asn Leu Arg Lys Glu Lys Ser Lys Val Ala Lys Lys Ile Lys Thr Gln
                85                  90                  95

Glu Lys Ala

<210> SEQ ID NO 31
<211> LENGTH: 99
<212> TYPE: PRT
<213> ORGANISM: Homo sapiens
```

<400> SEQUENCE: 31

Met Ala Asn Asn Tyr Lys Lys Ile Val Leu Leu Lys Gly Leu Glu Val
1               5                   10                  15

Ile Asn Asp Tyr His Phe Arg Ile Val Lys Ser Leu Leu Ser Asn Asp
            20                  25                  30

Leu Lys Leu Asn Pro Lys Met Lys Glu Glu Tyr Asp Lys Ile Gln Ile
        35                  40                  45

Ala Asp Leu Met Glu Glu Lys Phe Pro Gly Asp Ala Gly Leu Gly Lys
    50                  55                  60

Leu Ile Glu Phe Phe Lys Glu Ile Pro Thr Leu Gly Asp Leu Ala Glu
65                  70                  75                  80

Thr Leu Lys Arg Glu Lys Leu Lys Val Lys Gly Ile Ile Pro Ser Lys
                85                  90                  95

Lys Thr Lys

<210> SEQ ID NO 32
<211> LENGTH: 113
<212> TYPE: PRT
<213> ORGANISM: Homo sapiens

<400> SEQUENCE: 32

Met Glu Ser Lys Tyr Lys Glu Ile Leu Leu Leu Thr Ser Leu Asp Asn
1               5                   10                  15

Ile Thr Asp Glu Glu Leu Asp Arg Phe Lys Cys Phe Leu Pro Asp Glu
            20                  25                  30

Phe Asn Ile Ala Thr Gly Lys Leu His Thr Leu Asn Ser Thr Ser Ser
        35                  40                  45

Gln Leu Asp Leu Lys Arg Trp His Gly Val Cys Ser Glu Glu Asp Arg
    50                  55                  60

Ile Phe Gln Lys Leu Asn Tyr Met Leu Val Ala Lys Cys Leu Arg Glu
65                  70                  75                  80

Glu Gln Glu Thr Gly Ile Cys Gly Ser Pro Ser Ser Ala Arg Ser Val
                85                  90                  95

Ser Gln Ser Arg Leu Gly Leu Ser Phe His Gly Ile Ser Gly Asn Ala
                100                 105                 110

Cys

<210> SEQ ID NO 33
<211> LENGTH: 96
<212> TYPE: PRT
<213> ORGANISM: Homo sapiens

<400> SEQUENCE: 33

Met Glu Ser Lys Tyr Lys Glu Ile Leu Leu Leu Thr Ser Leu Asp Asn
1               5                   10                  15

Ile Thr Asp Glu Glu Leu Asp Arg Phe Lys Cys Phe Leu Pro Asp Glu
            20                  25                  30

Phe Asn Ile Ala Thr Gly Lys Leu His Thr Leu Asn Ser Thr Ser Ser
        35                  40                  45

Gln Leu Asp Leu Lys Arg Trp His Gly Val Cys Ser Glu Glu Asp Arg
    50                  55                  60

Ile Phe Gln Lys Leu Asn Tyr Met Leu Val Ala Lys Cys Leu Arg Glu
65                  70                  75                  80

Glu Gln Glu Thr Gly Ile Cys Gly Ser Pro Ser Ser Ala Arg Ser Val
                85                  90                  95

<210> SEQ ID NO 34
<211> LENGTH: 95
<212> TYPE: PRT
<213> ORGANISM: Homo sapiens

<400> SEQUENCE: 34

Met Glu Ser Lys Tyr Lys Glu Ile Leu Leu Thr Gly Leu Asp Asn
1               5                   10                  15

Ile Thr Asp Glu Glu Leu Asp Arg Phe Lys Phe Phe Leu Ser Asp Glu
                20                  25                  30

Phe Asn Ile Ala Thr Gly Lys Leu His Thr Ala Asn Arg Ile Gln Val
            35                  40                  45

Ala Thr Leu Met Ile Gln Asn Ala Gly Ala Val Ser Ala Val Met Lys
        50                  55                  60

Thr Ile Arg Ile Phe Gln Lys Leu Asn Tyr Met Leu Leu Ala Lys Arg
65                  70                  75                  80

Leu Gln Glu Glu Lys Gly Lys Val Asp Lys Gln Tyr Lys Ser Val
                85                  90                  95

<210> SEQ ID NO 35
<211> LENGTH: 92
<212> TYPE: PRT
<213> ORGANISM: Homo sapiens

<400> SEQUENCE: 35

Met Gly Lys Lys Tyr Lys Asn Ile Val Leu Leu Lys Gly Leu Glu Val
1               5                   10                  15

Ile Asn Asp Tyr His Phe Arg Met Val Lys Ser Leu Leu Ser Asn Asp
                20                  25                  30

Leu Lys Leu Asn Leu Lys Met Arg Glu Glu Tyr Asp Lys Ile Gln Ile
            35                  40                  45

Ala Asp Leu Met Glu Glu Lys Phe Arg Gly Asp Ala Gly Leu Gly Lys
        50                  55                  60

Leu Ile Lys Ile Phe Glu Asp Ile Pro Thr Leu Glu Asp Leu Ala Glu
65                  70                  75                  80

Thr Leu Lys Lys Glu Lys Leu Lys Val Lys Gly Pro
                85                  90

<210> SEQ ID NO 36
<211> LENGTH: 99
<212> TYPE: PRT
<213> ORGANISM: Homo sapiens

<400> SEQUENCE: 36

Met Val Asn Glu Tyr Lys Lys Ile Leu Leu Lys Gly Phe Glu Leu
1               5                   10                  15

Met Asp Asp Tyr His Phe Thr Ser Ile Lys Ser Leu Leu Ala Tyr Asp
                20                  25                  30

Leu Gly Leu Thr Thr Lys Met Gln Glu Glu Tyr Asn Arg Ile Lys Ile
            35                  40                  45

Thr Asp Leu Met Glu Lys Lys Phe Gln Gly Val Ala Cys Leu Asp Lys
        50                  55                  60

Leu Ile Glu Leu Ala Lys Asp Met Pro Ser Leu Lys Asn Leu Val Asn
65                  70                  75                  80

Asn Leu Arg Lys Glu Lys Ser Lys Val Ala Lys Ile Lys Thr Gln
                85                  90                  95

Glu Lys Ala

<210> SEQ ID NO 37
<211> LENGTH: 99
<212> TYPE: PRT
<213> ORGANISM: Homo sapiens

<400> SEQUENCE: 37

Met Ala Asn Asn Tyr Lys Lys Ile Val Leu Leu Lys Gly Leu Glu Val
1               5                   10                  15

Ile Asn Asp Tyr His Phe Arg Ile Val Lys Ser Leu Leu Ser Asn Asp
                20                  25                  30

Leu Lys Leu Asn Pro Lys Met Lys Glu Glu Tyr Asp Lys Ile Gln Ile
            35                  40                  45

Ala Asp Leu Met Glu Glu Lys Phe Pro Gly Asp Ala Gly Leu Gly Lys
        50                  55                  60

Leu Ile Glu Phe Phe Lys Glu Ile Pro Thr Leu Gly Asp Leu Ala Glu
65                  70                  75                  80

Thr Leu Lys Arg Glu Lys Leu Lys Val Lys Gly Ile Ile Pro Ser Lys
                85                  90                  95

Lys Thr Lys

<210> SEQ ID NO 38
<211> LENGTH: 97
<212> TYPE: PRT
<213> ORGANISM: Homo sapiens

<400> SEQUENCE: 38

Met Val Ser Ser Ala Gln Met Gly Phe Asn Leu Gln Ala Leu Leu Glu
1               5                   10                  15

Gln Leu Ser Gln Asp Glu Leu Ser Lys Phe Lys Tyr Leu Ile Thr Thr
                20                  25                  30

Phe Ser Leu Ala His Glu Leu Gln Lys Ile Pro His Lys Glu Val Asp
            35                  40                  45

Lys Ala Asp Gly Lys Gln Leu Val Glu Ile Leu Thr Thr His Cys Asp
        50                  55                  60

Ser Tyr Trp Val Glu Met Ala Ser Leu Gln Val Phe Glu Lys Met His
65                  70                  75                  80

Arg Met Asp Leu Ser Glu Arg Ala Lys Asp Glu Val Arg Glu Ala Ala
                85                  90                  95

Leu

<210> SEQ ID NO 39
<211> LENGTH: 95
<212> TYPE: PRT
<213> ORGANISM: Homo sapiens

<400> SEQUENCE: 39

Met Ala Gly Gly Ala Trp Gly Arg Leu Ala Cys Tyr Leu Glu Phe Leu
1               5                   10                  15

Lys Lys Glu Glu Leu Lys Glu Phe Gln Leu Leu Leu Ala Asn Lys Ala
                20                  25                  30

His Ser Arg Ser Ser Gly Glu Thr Pro Ala Gln Pro Glu Lys Thr
            35                  40                  45

Ser Gly Met Glu Val Ala Ser Tyr Leu Val Ala Gln Tyr Gly Glu Gln
        50                  55                  60

Arg Ala Trp Asp Leu Ala Leu His Thr Trp Glu Gln Met Gly Leu Arg

```
                65                  70                  75                  80
Ser Leu Cys Ala Gln Ala Gln Glu Gly Ala Gly His Ser Pro Ser
                85                  90                  95

<210> SEQ ID NO 40
<211> LENGTH: 94
<212> TYPE: PRT
<213> ORGANISM: Homo sapiens

<400> SEQUENCE: 40

Met Ala Ser Thr Arg Cys Lys Leu Ala Arg Tyr Leu Glu Asp Leu
1               5                   10                  15

Asp Val Asp Leu Lys Lys Phe Lys Met His Leu Glu Asp Tyr Pro Pro
                20                  25                  30

Gln Lys Gly Cys Ile Pro Leu Pro Arg Gly Gln Thr Glu Lys Ala Asp
            35                  40                  45

His Val Asp Leu Ala Thr Leu Met Ile Asp Phe Asn Gly Glu Glu Lys
        50                  55                  60

Ala Trp Ala Met Ala Val Trp Ile Phe Ala Ala Ile Asn Arg Arg Asp
65                  70                  75                  80

Leu Tyr Glu Lys Ala Lys Arg Asp Glu Pro Lys Trp Gly Ser
                85                  90

<210> SEQ ID NO 41
<211> LENGTH: 94
<212> TYPE: PRT
<213> ORGANISM: Homo sapiens

<400> SEQUENCE: 41

Met Ala Ala Ser Phe Phe Ser Asp Phe Gly Leu Met Trp Tyr Leu Glu
1               5                   10                  15

Glu Leu Lys Lys Glu Glu Phe Arg Lys Phe Lys Glu His Leu Lys Gln
                20                  25                  30

Met Thr Leu Gln Leu Glu Leu Lys Gln Ile Pro Trp Thr Glu Val Lys
            35                  40                  45

Lys Ala Ser Arg Glu Glu Leu Ala Asn Leu Leu Ile Lys His Tyr Glu
        50                  55                  60

Glu Gln Gln Ala Trp Asn Ile Thr Leu Arg Ile Phe Gln Lys Met Asp
65                  70                  75                  80

Arg Lys Asp Leu Cys Met Lys Val Met Arg Glu Arg Thr Gly
                85                  90

<210> SEQ ID NO 42
<211> LENGTH: 108
<212> TYPE: PRT
<213> ORGANISM: Homo sapiens

<400> SEQUENCE: 42

Met Gly Asp Lys Ser Leu Thr Phe Ser Ser Tyr Gly Leu Gln Trp Cys
1               5                   10                  15

Leu Tyr Glu Leu Asp Lys Glu Glu Phe Gln Thr Phe Lys Glu Leu Leu
                20                  25                  30

Lys Lys Lys Ser Ser Glu Ser Thr Cys Ser Ile Pro Gln Phe Glu
            35                  40                  45

Ile Glu Asn Ala Asn Val Glu Cys Leu Ala Leu Leu His Glu Tyr
        50                  55                  60

Tyr Gly Ala Ser Leu Ala Trp Ala Thr Ser Ile Ser Ile Phe Glu Asn
65                  70                  75                  80
```

Met Asn Leu Arg Thr Leu Ser Glu Lys Ala Arg Asp Met Lys Arg
                85                  90                  95

His Ser Pro Glu Asp Pro Glu Ala Thr Met Thr Asp
            100                 105

<210> SEQ ID NO 43
<211> LENGTH: 89
<212> TYPE: PRT
<213> ORGANISM: Homo sapiens

<400> SEQUENCE: 43

Leu Ala Val Ala Arg Glu Leu Leu Ala Ala Leu Glu Glu Leu Ser
1               5                   10                  15

Gln Glu Gln Leu Lys Arg Phe Arg His Lys Leu Arg Asp Val Gly Pro
                20                  25                  30

Asp Gly Arg Ser Ile Pro Trp Gly Arg Leu Glu Arg Ala Asp Ala Val
            35                  40                  45

Asp Leu Ala Glu Gln Leu Ala Gln Phe Tyr Gly Pro Glu Pro Ala Leu
50                  55                  60

Glu Val Ala Arg Lys Thr Leu Lys Arg Ala Asp Ala Arg Asp Val Ala
65                  70                  75                  80

Ala Gln Leu Gln Glu Arg Arg Leu Gln
                85

<210> SEQ ID NO 44
<211> LENGTH: 94
<212> TYPE: PRT
<213> ORGANISM: Homo sapiens

<400> SEQUENCE: 44

Met Thr Ser Pro Gln Leu Glu Trp Thr Leu Thr Leu Leu Glu Gln
1               5                   10                  15

Leu Asn Glu Asp Glu Leu Lys Ser Phe Lys Ser Leu Leu Trp Ala Phe
                20                  25                  30

Pro Leu Glu Asp Val Leu Gln Lys Thr Pro Trp Ser Glu Val Glu Glu
            35                  40                  45

Ala Asp Gly Lys Lys Leu Ala Glu Ile Leu Val Asn Thr Ser Ser Glu
50                  55                  60

Asn Trp Ile Arg Asn Ala Thr Val Asn Ile Leu Glu Glu Met Asn Leu
65                  70                  75                  80

Thr Glu Leu Cys Lys Met Ala Lys Ala Glu Met Met Glu Ile
                85                  90

<210> SEQ ID NO 45
<211> LENGTH: 107
<212> TYPE: PRT
<213> ORGANISM: Homo sapiens

<400> SEQUENCE: 45

Phe Ser Cys Tyr Pro Gly Ser Pro Cys Glu Asn Gly Val Met Leu Tyr
1               5                   10                  15

Met Arg Asn Val Ser His Glu Glu Leu Gln Arg Phe Lys Gln Leu Leu
                20                  25                  30

Leu Thr Glu Leu Ser Thr Gly Thr Met Pro Ile Thr Trp Asp Gln Val
            35                  40                  45

Glu Thr Ala Ser Trp Ala Glu Val Val His Leu Leu Ile Glu Arg Phe
50                  55                  60

```
Pro Gly Arg Arg Ala Trp Asp Val Thr Ser Asn Ile Phe Ala Ile Met
 65                  70                  75                  80

Asn Cys Asp Lys Met Cys Val Val Val Arg Arg Glu Ile Asn Ala Ile
                 85                  90                  95

Leu Pro Thr Leu Glu Pro Glu Asp Leu Asn Val
                100                 105
```

<210> SEQ ID NO 46
<211> LENGTH: 94
<212> TYPE: PRT
<213> ORGANISM: Homo sapiens

<400> SEQUENCE: 46

```
Met Ala Glu Ser Phe Ser Asp Phe Gly Leu Leu Trp Tyr Leu Lys
  1               5                  10                  15

Glu Leu Arg Lys Glu Glu Phe Trp Lys Phe Lys Glu Leu Leu Lys Gln
                 20                  25                  30

Pro Leu Glu Lys Phe Glu Leu Lys Pro Ile Pro Trp Ala Glu Leu Lys
             35                  40                  45

Lys Ala Ser Lys Glu Asp Val Ala Lys Leu Leu Asp Lys His Tyr Pro
 50                  55                  60

Gly Lys Gln Ala Trp Glu Val Thr Leu Asn Leu Phe Leu Gln Ile Asn
 65                  70                  75                  80

Arg Lys Asp Leu Trp Thr Lys Ala Gln Glu Glu Met Arg Asn
                 85                  90
```

<210> SEQ ID NO 47
<211> LENGTH: 91
<212> TYPE: PRT
<213> ORGANISM: Homo sapiens

<400> SEQUENCE: 47

```
Met Ala Glu Ser Asp Ser Thr Asp Phe Asp Leu Leu Trp Tyr Leu Glu
  1               5                  10                  15

Asn Leu Ser Asp Lys Glu Phe Gln Ser Phe Lys Lys Tyr Leu Ala Arg
                 20                  25                  30

Lys Ile Leu Asp Phe Lys Leu Pro Gln Phe Pro Leu Ile Gln Met Thr
             35                  40                  45

Lys Glu Glu Leu Ala Asn Val Leu Pro Ile Ser Tyr Glu Gly Gln Tyr
 50                  55                  60

Ile Trp Asn Met Leu Phe Ser Ile Phe Ser Met Met Arg Lys Glu Asp
 65                  70                  75                  80

Leu Cys Arg Lys Ile Ile Gly Arg Arg Asn Arg
                 85                  90
```

<210> SEQ ID NO 48
<211> LENGTH: 96
<212> TYPE: PRT
<213> ORGANISM: Homo sapiens

<400> SEQUENCE: 48

```
Met Ala Met Ala Lys Ala Arg Lys Pro Arg Glu Ala Leu Leu Trp Ala
  1               5                  10                  15

Leu Ser Asp Leu Glu Glu Asn Asp Phe Lys Lys Leu Lys Phe Tyr Leu
                 20                  25                  30

Arg Asp Met Thr Leu Ser Glu Gly Gln Pro Pro Leu Ala Arg Gly Glu
             35                  40                  45

Leu Glu Gly Leu Ile Pro Val Asp Leu Ala Glu Leu Leu Ile Ser Lys
```

```
                    50                  55                  60
Tyr Gly Glu Lys Glu Ala Val Lys Val Val Leu Lys Gly Leu Lys Val
 65                  70                  75                  80

Met Asn Leu Leu Glu Leu Val Asp Gln Leu Ser His Ile Cys Leu His
                     85                  90                  95
```

<210> SEQ ID NO 49
<211> LENGTH: 107
<212> TYPE: PRT
<213> ORGANISM: Homo sapiens

<400> SEQUENCE: 49

```
Met Asn Phe Ser Val Ile Thr Cys Pro Asn Gly Gly Thr Asn Gln Gly
  1               5                  10                  15

Leu Leu Pro Tyr Leu Met Ala Leu Asp Gln Tyr Gln Leu Glu Glu Phe
                 20                  25                  30

Lys Leu Cys Leu Glu Pro Gln Gln Leu Met Asp Phe Trp Ser Ala Pro
             35                  40                  45

Gln Gly His Phe Pro Arg Ile Pro Trp Ala Asn Leu Arg Ala Ala Asp
         50                  55                  60

Pro Leu Asn Leu Ser Phe Leu Leu Asp Glu His Phe Pro Lys Gly Gln
 65                  70                  75                  80

Ala Trp Lys Val Val Leu Gly Ile Phe Gln Thr Met Asn Leu Thr Ser
                 85                  90                  95

Leu Cys Glu Lys Val Arg Ala Glu Met Lys Glu
                100                 105
```

<210> SEQ ID NO 50
<211> LENGTH: 95
<212> TYPE: PRT
<213> ORGANISM: Homo sapiens

<400> SEQUENCE: 50

```
Met Leu Arg Thr Ala Gly Arg Asp Gly Leu Cys Arg Leu Ser Thr Tyr
  1               5                  10                  15

Leu Glu Glu Leu Glu Ala Val Glu Leu Lys Lys Phe Lys Leu Tyr Leu
                 20                  25                  30

Gly Thr Ala Thr Glu Leu Gly Glu Gly Lys Ile Pro Trp Gly Ser Met
             35                  40                  45

Glu Lys Ala Gly Pro Leu Glu Met Ala Gln Leu Leu Ile Thr His Phe
         50                  55                  60

Gly Pro Glu Glu Ala Trp Arg Leu Ala Leu Ser Thr Phe Glu Arg Ile
 65                  70                  75                  80

Asn Arg Lys Asp Leu Trp Glu Arg Gly Gln Arg Glu Asp Leu Val
                 85                  90                  95
```

<210> SEQ ID NO 51
<211> LENGTH: 97
<212> TYPE: PRT
<213> ORGANISM: Homo sapiens

<400> SEQUENCE: 51

```
Met Ala Asp Ser Ser Ser Ser Phe Phe Pro Asp Phe Gly Leu Leu
  1               5                  10                  15

Leu Tyr Leu Glu Glu Leu Asn Lys Glu Glu Leu Asn Thr Phe Lys Leu
                 20                  25                  30

Phe Leu Lys Glu Thr Met Glu Pro Glu His Gly Leu Thr Pro Trp Asn
             35                  40                  45
```

Glu Val Lys Lys Ala Arg Arg Glu Asp Leu Ala Asn Leu Met Lys Lys
            50                  55                  60

Tyr Tyr Pro Gly Glu Lys Ala Trp Ser Val Ser Leu Lys Ile Phe Gly
65                  70                  75                  80

Lys Met Asn Leu Lys Asp Leu Cys Glu Arg Ala Lys Glu Glu Ile Asn
                85                  90                  95

Trp

<210> SEQ ID NO 52
<211> LENGTH: 92
<212> TYPE: PRT
<213> ORGANISM: Homo sapiens

<400> SEQUENCE: 52

Met Gly Arg Ala Arg Asp Ala Ile Leu Asp Ala Leu Glu Asn Leu Thr
1               5                   10                  15

Ala Glu Glu Leu Lys Lys Phe Lys Leu Lys Leu Leu Ser Val Pro Leu
                20                  25                  30

Arg Glu Gly Tyr Gly Arg Ile Pro Arg Gly Ala Leu Leu Ser Met Asp
            35                  40                  45

Ala Leu Asp Leu Thr Asp Lys Leu Val Ser Phe Tyr Leu Glu Thr Tyr
        50                  55                  60

Gly Ala Glu Leu Thr Ala Asn Val Leu Arg Asp Met Gly Leu Gln Glu
65                  70                  75                  80

Met Ala Gly Gln Leu Gln Ala Ala Thr His Gln Gly
                85                  90

<210> SEQ ID NO 53
<211> LENGTH: 89
<212> TYPE: PRT
<213> ORGANISM: Homo sapiens

<400> SEQUENCE: 53

Met Gly Thr Lys Arg Glu Ala Ile Leu Lys Val Leu Glu Asn Leu Thr
1               5                   10                  15

Pro Glu Glu Leu Lys Lys Phe Lys Met Lys Leu Gly Thr Val Pro Leu
                20                  25                  30

Arg Glu Gly Phe Glu Arg Ile Pro Arg Gly Ala Leu Gly Gln Leu Asp
            35                  40                  45

Ile Val Asp Leu Thr Asp Lys Leu Val Ala Ser Tyr Tyr Glu Asp Tyr
        50                  55                  60

Ala Ala Glu Leu Val Val Ala Val Leu Arg Asp Met Arg Met Leu Glu
65                  70                  75                  80

Glu Ala Ala Arg Leu Gln Arg Ala Ala
                85

<210> SEQ ID NO 54
<211> LENGTH: 90
<212> TYPE: PRT
<213> ORGANISM: Homo sapiens

<400> SEQUENCE: 54

Met Ala Ser Ser Ala Glu Leu Asp Phe Asn Leu Gln Ala Leu Leu Glu
1               5                   10                  15

Gln Leu Ser Gln Asp Glu Leu Ser Lys Phe Lys Ser Leu Ile Arg Thr
                20                  25                  30

Ile Ser Leu Gly Lys Glu Leu Gln Thr Val Pro Gln Thr Glu Val Asp

```
                35                  40                  45
Lys Ala Asn Gly Lys Gln Leu Val Glu Ile Phe Thr Ser His Ser Cys
        50                  55                  60
Ser Tyr Trp Ala Gly Met Ala Ala Ile Gln Val Phe Glu Lys Met Asn
65                  70                  75                  80
Gln Thr His Leu Ser Gly Arg Ala Asp Glu
                85                  90
```

<210> SEQ ID NO 55
<211> LENGTH: 92
<212> TYPE: PRT
<213> ORGANISM: Homo sapiens

<400> SEQUENCE: 55

```
Met Ala Lys Thr Pro Ser Asp His Leu Leu Ser Thr Leu Glu Glu Leu
1               5                   10                  15
Val Pro Tyr Asp Phe Glu Lys Phe Lys Phe Lys Leu Gln Asn Thr Ser
                20                  25                  30
Val Gln Lys Glu His Ser Arg Ile Pro Arg Ser Gln Ile Gln Arg Ala
            35                  40                  45
Arg Pro Val Lys Met Ala Thr Leu Leu Val Thr Tyr Tyr Gly Glu Glu
        50                  55                  60
Tyr Ala Val Gln Leu Thr Leu Gln Val Leu Arg Ala Ile Asn Gln Arg
65                  70                  75                  80
Leu Leu Ala Glu Glu Leu His Arg Ala Ala Ile Gln
                85                  90
```

<210> SEQ ID NO 56
<211> LENGTH: 89
<212> TYPE: PRT
<213> ORGANISM: Homo sapiens

<400> SEQUENCE: 56

```
Met Gly Arg Ala Arg Asp Ala Ile Leu Asp Ala Leu Glu Asn Leu Thr
1               5                   10                  15
Ala Glu Glu Leu Lys Lys Phe Lys Leu Lys Leu Leu Ser Val Pro Leu
                20                  25                  30
Arg Glu Gly Tyr Gly Arg Ile Pro Arg Gly Ala Leu Leu Ser Met Asp
            35                  40                  45
Ala Leu Asp Leu Thr Asp Lys Leu Val Ser Phe Tyr Leu Glu Thr Tyr
        50                  55                  60
Gly Ala Glu Leu Thr Ala Asn Val Leu Arg Asp Met Gly Leu Gln Glu
65                  70                  75                  80
Met Ala Gly Gln Leu Gln Ala Ala Thr
                85
```

<210> SEQ ID NO 57
<211> LENGTH: 89
<212> TYPE: PRT
<213> ORGANISM: Homo sapiens

<400> SEQUENCE: 57

```
Met Gly Thr Lys Arg Glu Ala Ile Leu Lys Val Leu Glu Asn Leu Thr
1               5                   10                  15
Pro Glu Glu Leu Lys Lys Phe Lys Met Lys Leu Gly Thr Val Pro Leu
                20                  25                  30
Arg Glu Gly Phe Glu Arg Ile Pro Arg Gly Ala Leu Gly Gln Leu Asp
            35                  40                  45
```

```
Ile Val Asp Leu Thr Asp Lys Leu Val Ala Ser Tyr Tyr Glu Asp Tyr
         50                  55                  60

Ala Ala Glu Leu Val Val Ala Val Leu Arg Asp Met Arg Met Leu Glu
 65                  70                  75                  80

Glu Ala Ala Arg Leu Gln Arg Ala Ala
                 85

<210> SEQ ID NO 58
<211> LENGTH: 89
<212> TYPE: PRT
<213> ORGANISM: Homo sapiens

<400> SEQUENCE: 58

Met Gly Arg Ala Arg Asp Ala Ile Leu Asp Ala Leu Glu Asn Leu Thr
 1               5                  10                  15

Ala Glu Glu Leu Lys Lys Phe Lys Leu Lys Leu Ser Val Pro Leu
                 20                  25                  30

Arg Glu Gly Tyr Gly Arg Ile Pro Arg Gly Ala Leu Leu Ser Met Asp
                 35                  40                  45

Ala Leu Asp Leu Thr Asp Lys Leu Val Ser Phe Tyr Leu Glu Thr Tyr
         50                  55                  60

Gly Ala Glu Leu Thr Ala Asn Val Leu Arg Asp Met Gly Leu Gln Glu
 65                  70                  75                  80

Met Ala Gly Gln Leu Gln Ala Ala Thr
                 85

<210> SEQ ID NO 59
<211> LENGTH: 89
<212> TYPE: PRT
<213> ORGANISM: Mus musculus

<400> SEQUENCE: 59

Met Gly Arg Ala Arg Asp Ala Ile Leu Asp Ala Leu Glu Asn Leu Ser
 1               5                  10                  15

Gly Asp Glu Leu Lys Lys Phe Lys Met Lys Leu Leu Thr Val Gln Leu
                 20                  25                  30

Arg Glu Gly Tyr Gly Arg Ile Pro Arg Gly Ala Leu Leu Gln Met Asp
                 35                  40                  45

Ala Ile Asp Leu Thr Asp Lys Leu Val Ser Tyr Tyr Leu Glu Ser Tyr
         50                  55                  60

Gly Leu Glu Leu Thr Met Thr Val Leu Arg Asp Met Gly Leu Gln Glu
 65                  70                  75                  80

Leu Ala Glu Gln Leu Gln Thr Thr Lys
                 85

<210> SEQ ID NO 60
<211> LENGTH: 89
<212> TYPE: PRT
<213> ORGANISM: Homo sapiens

<400> SEQUENCE: 60

Met Gly Thr Lys Arg Glu Ala Ile Leu Lys Val Leu Glu Asn Leu Thr
 1               5                  10                  15

Pro Glu Glu Leu Lys Lys Phe Lys Met Lys Leu Gly Thr Val Pro Leu
                 20                  25                  30

Arg Glu Gly Phe Glu Arg Ile Pro Arg Gly Ala Leu Gly Gln Leu Asp
                 35                  40                  45
```

```
Ile Val Asp Leu Thr Asp Lys Leu Val Ala Ser Tyr Tyr Glu Asp Tyr
 50                  55                  60

Ala Ala Glu Leu Val Val Ala Val Leu Arg Asp Met Arg Met Leu Glu
 65                  70                  75                  80

Glu Ala Ala Arg Leu Gln Arg Ala Ala
                 85
```

<210> SEQ ID NO 61
<211> LENGTH: 97
<212> TYPE: PRT
<213> ORGANISM: Homo sapiens

<400> SEQUENCE: 61

```
Met Ala Ser Ser Ala Glu Leu Asp Phe Asn Leu Gln Ala Leu Leu Glu
 1                5                  10                  15

Gln Leu Ser Gln Asp Glu Leu Ser Lys Phe Lys Ser Leu Ile Arg Thr
                 20                  25                  30

Ile Ser Leu Gly Lys Glu Leu Gln Thr Val Pro Gln Thr Glu Val Asp
             35                  40                  45

Lys Ala Asn Gly Lys Gln Leu Val Glu Ile Phe Thr Ser His Ser Cys
 50                  55                  60

Ser Tyr Trp Ala Gly Met Ala Ala Ile Gln Val Phe Glu Lys Met Asn
 65                  70                  75                  80

Gln Thr His Leu Ser Gly Arg Ala Asp Glu His Cys Val Met Pro Pro
                 85                  90                  95

Pro
```

<210> SEQ ID NO 62
<211> LENGTH: 113
<212> TYPE: PRT
<213> ORGANISM: Homo sapiens

<400> SEQUENCE: 62

```
Met Glu Ser Lys Tyr Lys Glu Ile Leu Leu Leu Thr Ser Leu Asp Asn
 1                5                  10                  15

Ile Thr Asp Glu Glu Leu Asp Arg Phe Lys Cys Phe Leu Pro Asp Glu
                 20                  25                  30

Phe Asn Ile Ala Thr Gly Lys Leu His Thr Leu Asn Ser Thr Ser Ser
             35                  40                  45

Gln Leu Asp Leu Lys Arg Trp His Gly Val Cys Ser Glu Glu Asp Arg
 50                  55                  60

Ile Phe Gln Lys Leu Asn Tyr Met Leu Val Ala Lys Cys Leu Arg Glu
 65                  70                  75                  80

Glu Gln Glu Thr Gly Ile Cys Gly Ser Pro Ser Ser Ala Arg Ser Val
                 85                  90                  95

Ser Gln Ser Arg Leu Gly Leu Ser Phe His Gly Ile Ser Gly Asn Ala
                100                 105                 110

Cys
```

<210> SEQ ID NO 63
<211> LENGTH: 15
<212> TYPE: PRT
<213> ORGANISM: Artificial sequence
<220> FEATURE:
<223> OTHER INFORMATION: Synthetic peptide

```
<400> SEQUENCE: 63

Cys Gly Ser Pro Ser Ser Ala Arg Ser Val Ser Gln Ser Arg Leu
1               5                   10                  15
```

COMPOSITIONS AND METHODS FOR MODULATION OF IMMUNE RESPONSE

CROSS REFERENCE TO RELATED APPLICATIONS

The present application is a continuation of U.S. patent application Ser. No. 15/117,629, filed Aug. 9, 2016, which is a § 371 National Entry Application of PCT/US2015/015761, filed Feb. 13, 2015, which claims the benefit of U.S. Provisional Patent Application Ser. No. 61/939,499, filed Feb. 13, 2014, each of which is incorporated by reference in its entirety.

FIELD

Provided herein are compositions and methods for modulation of immune response via PYRIN domain-only proteins POP1, POP2, and/or POP3. In particular, POP1, POP2, and/or POP3 are inhibited to enhance an immune response (e.g., to treat or prevent infection), or POP1, POP2, and/or POP3 are administered or activated to reduce an immune response (e.g., to treat or prevent autoimmune or inflammatory disease).

BACKGROUND

The innate immune system is essential as a first line of defense to rapidly detect invading pathogens and to elicit a proper immune response for clearing infections and initiating wound healing. Infections are sensed by germline encoded pattern recognition receptors (PRRs) present in different compartments of immune and non-immune cells, and include Toll-like receptors (TLRs), RIG-Mike receptors (RLRs), AIM2-like receptors (ALRs) and Nod-like receptors (NLRs). Activation of PRRs promotes an inflammatory host response through up-regulation of inflammatory mediators, including cytokines and chemokines to directly eliminate pathogens and to mount a long-lasting adaptive immune response. PRRs are not limited to specifically recognize conserved molecules on pathogens referred to as pathogen associated molecular patterns (PAMPs), but also sense host-derived damage-associated molecular patterns (DAMPs). The NLR family consists of 22 intracellular cytosolic PRRs with a tripartite domain architecture, composed of a C-terminalleucine rich region (LRR), a central nucleotide binding NACHT domain, and an N-terminal effector domain crucial for downstream signaling. The NLR effector domain is either a transactivation domain (NLRAs), a baculovirus inhibitor of apoptosis repeat (BIR) (NLRBs), an unknown domain (NLRX), a caspase recruitment domain (CARD) (NLRCs), or a PYRIN domain (PYD) in the largest NLR subfatnily (NLRPs). While pathogen activation of some NLRCs is linked to signalosome activation, others can activate caspase-1. Similarly, some of the characterized NLRPs also detect PAMPs and DAMPs in the cytosol and respond with the formation and activation of caspase-I-activating inflammasomes in macrophages. The apoptotic speck-like protein containing a CARD (ASC, PYCARD, TMSI) is the essential adaptor for bridging NLRPs with caspase-1, and macrophages deficient in ASC are impaired in caspase-1 activation and maturation of IL-1β and IL-18. Inflammasomes are protein scaffolds linking PAMP and DAMP recognition by NLRP members to the activation of caspase-I-dependent processing and release of the inflammatory cytokines interleukin (IL)-Iβ and IL-18. ALRs, including AIM2 and IFI16 activate inflammasomes or type I interferon, respectively. They sense cytosolic DNA in autoimmune disease to perpetuate disease, as well as DNA from bacteria and viruses during infection.

SUMMARY

Provided herein are compositions and methods for modulation of immune response via PYRIN domain-only proteins POP1, POP2, and/or POP3. In particular, POP1, POP2, and/or POP3 are inhibited to enhance an immune response (e.g., to treat or prevent infection), or POP1, POP2, and/or POP3 are administered or activated to reduce an immune response (e.g., to treat or prevent autoimmune or inflammatory disease). In some embodiments, POP1-, POP2-, and/or POP3-based inflammasome (e.g., NLRP3 inflammasomes) inhibitors (e.g., POP1-, POP2-, or POP3-based peptide or peptidomimetics), are administered to: (a) inhibit inflammasome activity, (b) prevent IL-1β IL-18, and/or type I interferon release, (c) interfere with caspase-1 activation, (d) to prevent self-perpetuation of inflammasome responses, and/or (e) to block excessive production of cytokines (e.g., in inflammatory disease). In some embodiments, POP1, POP2, and/or POP3 are neutralized and/or inhibited (e.g., by administration of an inhibitor) to: (a) enhance immune response, (b) to boost adjuvant activity, and/or (c) for more efficiently clearing infections.

Provided herein are compositions comprising, inflammasome-inhibitory peptides, polypeptides, and protein, and methods of treating autoimmune and/or chronic inflammatory diseases and conditions therewith. In particular, polypeptides, peptides, and peptidomimetecs are provided that exhibit the inflammasome-inhibitory activity of POP1, POP2, or POP3 or an enhancement thereof, as well as methods of use thereof.

Provided herein are compositions comprising a peptide or polypeptide having less than 100% sequence identity with SEQ ID NO: 60 (full length POP1), encompassing a portion with at least 50% sequence identity (e.g., >50%, >60%, >70%, >75%, >80%, >85%, >90%, >95%) with SEQ ID NO: 60 (full length POP1), and exhibiting inflammasome-inhibitory activity. In some embodiments, a polypeptide or peptide has 100% sequence identity with all or a portion of POP1. In some embodiments, the peptide or polypeptide comprises a portion with at least 80% sequence similarity (e.g., >80%, >90%, >95%) with POP1. In some embodiments, the peptide or polypeptide has less than 100% sequence identity, but more than 50% sequence identity (e.g., >50%, >60%, >70%, >75%, >80%, >85%, >90%, >95%) with POP1. In some embodiments, the peptide or polypeptide has at least 80% sequence similarity with POP1.

Provided herein are compositions comprising a peptide or polypeptide having less than 100% sequence identity with SEQ ID NO: 61 (full length POP2), encompassing a portion with at least 50% sequence identity (e.g., >50%, >60%, >70%, >75%, >80%, >85%, >90%, >95%) with SEQ ID NO: 61 (full length POP2), and exhibiting inflammasome-inhibitory activity. In some embodiments, a polypeptide or peptide has 100% sequence identity with all or a portion of POP1. In some embodiments, the peptide or polypeptide comprises a portion with at least 80% sequence similarity (e.g., >80%, >90%, >95%) with POP2. In some embodiments, the peptide or polypeptide has less than 100% sequence identity, but more than 50% sequence identity (e.g., >50%, >60%, >70%, >75%, >80%, >85%, >90%, >95%) with POP2. In some embodiments, the peptide or polypeptide has at least 80% sequence similarity with POP2.

In some embodiments, the composition comprises a peptide or polypeptide with less than 100% but more than 50% sequence identity (e.g., <100%, but >50%, >60%, >70%, >75%, >80%, >85%, >90%, >95%) with SEQ ID NO: 62 (full length POP3). In some embodiments, the peptide or polypeptide has at least 80% sequence similarity (e.g., >80%, >85%, >90%, >95%) with POP3. In some embodiments, the peptide or polypeptide has less than 100% but more than 50% sequence identity (e.g., <100%, but >50%, >60%, >70%, >75%, >80%, >85%, >90%, >95%) with POP3. In some embodiments, the peptide or polypeptide has at least 80% sequence similarity (e.g., >80%, >85%, >90%, >95%, 100%) with POP3. In some embodiments, a peptide or polypeptide has a portion with 100% sequence identity with POP3. In some embodiments, the peptide or polypeptide has less than 100% sequence identity, but more than 50% sequence identity (e.g., <100%, but >50%, >60%, >70%, >75%, >80%, >85%, >90%, >95%) with POP3. In some embodiments, the peptide has at least 80% sequence similarity (e.g., >80%, >85%, >90%, >95%, 100%) with POP3.

In some embodiments, a peptide is provided that is 10-50 amino acids in length (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, and any ranges therein). In some embodiments, a synthetic peptide or polypeptide comprises at least 1 mutation (e.g., 1, 2, 3, 4, 5, 6, 7, 8, 9, 10, 11, 12, 13, 14, 15, and any ranges therein) from the wild-type or a natural POP1, POP2, or POP3 sequence over the length of the peptide. In some embodiments, a synthetic peptide comprises at least 1 non-conservative mutation (e.g., 1, 2, 3, 4, 5, 6, 7, 8, 9, 10, 11, 12, 13, 14, 15, and any ranges therein) from the wild-type or a natural POP1, POP2, or POP3 sequence over the length of the peptide. In some embodiments, a peptide comprises at least 1 conservative mutation (e.g., 1, 2, 3, 4, 5, 6, 7, 8, 9, 10, 11, 12, 13, 14, 15, and any ranges therein) from the wild-type or a natural POP1, POP2, or POP3 sequence over the length of the peptide.

In some embodiments, peptides have less than 100% but greater than 50% (e.g., 55%, 60%, 70%, 80%, 90%, 95%, and any ranges therein) sequence identity to a portion of POP1, POP2, or POP3 that is at least 5 amino acids in length (5, 10, 15, 20, 25, 30, 35, 40, 45, 50, and any ranges therein).

In some embodiments, compositions are provided comprising peptides and/or polypeptides that exhibit enhanced inflammasome-inhibitory activity relative to POP1, POP2, or POP3. In some embodiments, peptides and/or polypeptides exhibit >10% increased, >20% increased, >30% increased, >40% increased, >50% increased, >60% increased, >70% increased, >80% increased, >90% increased, >2-fold, >3-fold, >4-fold, >5-fold, >6-fold, >8 fold, >10-fold, or >20-fold inflammasome-inhibitory activity relative to POP1, POP2, or POP3. In some embodiments, enhanced inflammasome-inhibitory activity is exhibited in one or more assays descried herein (e.g., see Examples).

In some embodiments, compositions (e.g., small molecules, peptide, polypeptide, antibodies, nucleic acids, etc.) are provided (e.g., administered to a subject or cell) that enhance the inflammasome inhibitory activity of POP1, POP2, and/or POP3. Such compositions may increase cellular levels of POP1, POP2, and/or POP3, interact with POP1, POP2, and/or POP3 to increase activity, colocalize POP1, POP2, and/or POP3 with inflammasomes, etc.

In some embodiments, provided herein are pharmaceutical preparations comprising: (a) an POP1, POP2, or POP3 peptide or polypeptide described herein (e.g., in the preceding paragraphs); and (b) a physiologically acceptable buffer or carrier. In some embodiments, pharmaceutical preparations further comprise an additional therapeutic agent (e.g., for the treatment of: inflammation, pain, autoimmunity, etc.).

In some embodiments, provided herein are fusion peptides or polypeptides comprising: (a) a POP1-, POP2-, or POP3-peptide or polypeptide described herein (e.g., in the preceding paragraphs), and (b) a functional peptide or polypeptide segment. In some embodiments, the functional peptide or polypeptide segment comprises a signaling moiety, therapeutic moiety, localization moiety (e.g., cellular import signal, nuclear localization signal, etc.), detectable moiety (e.g., fluorescent moiety, contrast agent), or isolation/purification moiety (e.g., streptavidin, $His_6$, etc.).

In some embodiments, provided herein are polynucleotides encoding a POP1-, POP2-, or POP3-peptide or polypeptide described herein (e.g., in the preceding paragraphs). In some embodiments, provided herein are nucleic acid vectors (e.g., plasmid, bacmid, viral vector (e.g., AAV) comprising polynucleotides encoding a POP1-, POP2-, or POP3-peptide or polypeptide described herein (e.g., in the preceding paragraphs). In some embodiments, vectors further comprise a promoter and/or one or more expression elements (e.g., transcription enhancer, translational start site, internal ribosome entry site, etc.). In some embodiments, methods are provided comprising administering a polynucleotide or vector described herein to a subject or sample (e.g., for the treatment of autoimmunity or inflammation).

In some embodiments, provided herein are methods of treating autoimmunity or inflammation or a related condition or disease comprising administering a POP1-, POP2-, or POP3-peptide or polypeptide described herein (e.g., in the preceding paragraphs) to a subject suffering from autoimmunity or inflammation or said related condition or disease.

In some embodiments, provided herein are methods of preventing autoimmunity or inflammation or a related condition or disease comprising administering a POP1-, POP2-, or POP3-peptide or polypeptide described herein (e.g., in the preceding paragraphs) to a subject at risk (e.g., family history, genetic predisposition, lifestyle, age, gender, etc.) of autoimmunity or inflammation or said related condition or disease.

In some embodiments, compositions are provided comprising one or more agents (e.g., nucleic acid, small molecule, peptide, polypeptide, antibody, aptamer, etc.) that inhibit the inflammasome-inhibitory activity of POP1, POP2, or POP3. In some embodiments, inhibited inflammasome-inhibitory activity is exhibited in one or more assays descried herein (e.g., see Examples).

In some embodiments, provided herein are pharmaceutical preparations comprising: (a) a POP1, POP2, or POP3 inhibitor; and (b) a physiologically acceptable buffer or carrier. In some embodiments, pharmaceutical preparations further comprise an additional therapeutic agent (e.g., for the treatment of: inflammation, pain, autoimmunity, etc.).

In some embodiments, provided herein are fusion peptides or polypeptides comprising: (a) a POP1-, POP2-, or POP3-inhibitor, and (b) a functional peptide or polypeptide segment. In some embodiments, the functional peptide or polypeptide segment comprises a signaling moiety, therapeutic moiety, localization moiety (e.g., cellular import signal, nuclear localization signal, etc.), detectable moiety (e.g., fluorescent moiety, contrast agent), or isolation/purification moiety (e.g., streptavidin, $His_6$, etc.).

In some embodiments, provided herein are polynucleotides encoding a POP1-, POP2-, or POP3-inhibitory peptiode or polypeptide described herein (e.g., in the preceding paragraphs). In some embodiments, provided herein are nucleic acid vectors (e.g., plasmid, bacmid, viral vector (e.g., AAV) comprising polynucleotides encoding a POP1-, POP2-, or POP3-inhibitor. In some embodiments, vectors further comprise a promoter and/or one or more expression elements (e.g., transcription enhancer, translational start site, internal ribosome entry site, etc.). In some embodiments, methods are provided comprising administering a polynucleotide or vector described herein to a subject or sample (e.g., for the treatment of infection).

In some embodiments, provided herein are methods of treating infection of a wound or a condition or disease that is treated by an enhanced immune response comprising administering a POP1-, POP2-, or POP3-inhibitor to a subject. In some embodiments, provided herein are methods of preventing infection or a related condition or disease comprising administering a POP1- or POP3-inhibitor to a subject at risk (e.g., geographic location, lifestyle, age, etc.) of infection.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 1a-f. POP3 is a novel type-I interferon-inducible member of the POP family.

FIGS. 2a-b. POP3 is a gene located between IFI16 and IFIX. (a) cDNA showing the open reading frame of POP3 (Genbank accession number: KF562078 (SEQ ID NO: 26)) (b) A nucleotide BLAST (blastn) analysis against the assembled human RefSeq genomes detailing the genomic location of POP3 within the HIN-200 cluster flanked by IFI16 and PYHIN1 on human chromosome 1q23.

FIGS. 3a-d. POP3 shows characteristic features of PYDs present in HIN-200 proteins. (a) Amino acid sequence of POP3 (SEQ ID NO: 32). The PYD is shaded grey. The predicted α-helices are marked with blue lines (bottom), while the corresponding α-helices of AIM2, as determined by crystal structure 1, are marked with a line (top). (b) ClustalW alignment of the amino acid sequences corresponding to the PYDs of POP3 and human HIN-200 members. (c) ClustalW alignment of all human PYDs. The characteristic amino acid motifs found in HIN-200 members, which are also present in POP3, are highlighted in yellow. (d) Phylogenetic tree cluster analysis of sequences used in b. The HIN-200 cluster, which includes POP3 is highlighted.

FIGS. 4a-k. POP3 interacts with ALRs. (a, c, d) hMΦ were transfected with either control or a, POP3 #2 or c, d, POP3 siRNAs and infected with MVA or transfected with poly(dA:dT) as indicated for 16 h and analyzed for a, mature IL-1β and c, IL-6 by ELISA (n=3±s.e.m.) and d, TCL from FIG. 5f, were analyzed in parallel for expression of AIM2 and IFI16 by immunoblot. (b, f) THP-1 cells were transfected with siRNAs as above, and infected with MVA, transfected with poly(dA:dT) or treated with MSU or SiO2, as indicated for 16 h and analyzed for b, IL-1β secretion and f, IFN-β by ELISA (n=3±s.e.m.). (e, g) THP-1 (GFP) and THP-1 (GFP-POP3) cells were analyzed for secretion of e, TNFα and g, IFN-β in response to MVA and MCMV infection, transfection of poly(dA:dT) and treatment with MSU as indicated by ELISA (n=3±s.e.m.). (h) WT and POP3 transgenic BMDM were infected with MVA and analysed for mRNA expression of IL1ra and Il18 bp (n=3±s.e.m.). (i) The POP3 antibody does not cross-react with other POP family members. HEK293 cells were transfected with Myc-tagged POP1, POP2 and POP3 and immunoprobed with POP1, POP2 and POP3-specific antibodies. (j) The POP3 antibody does not cross-react with the related PYDs of AIM2 and IFI16. HEK293 cells were transfected with GFP or RFP-tagged POP3, AIM2-PYD and IFI16-PYD and immunoprobed with our POP3 antibody and with GFP and RFP antibodies as control. *denotes a cross-reactive protein.

FIGS. 5a-k. Silencing of POP3 in hMΦ enhances ALR-mediated IL-1β and IL-18 release.

FIGS. 10a-f. POP3 function in mouse macrophages. (a) Thioglycollate-elicited PM were isolated by peritoneal lavage, transfected with poly(dA:dT) for 16 h and analyzed for mature IL-1β by ELISA (n=3±s.e.m.). (b) BMDM isolated from a 2nd line of CD68-POP3 TG mice were infected with MVA, treated with LPS/ATP or transfected with poly (dA:dT) for 16 h and analyzed for mature IL-1β by ELISA (n=3±s.e.m.). (c) BMDM of UbiC-hCAR TG mice were immunoprobed for expression of hCARΔcyt using HEK293 cells transiently transfected with hCARΔcyt as a control. (d) WT (top panel) and UbiC-hCAR TG (bottom panel) BMDM were infected with increasing MOI of a GFP-expressing AdV and analyzed by fluorescence and phase contrast microscopy. (e) UbiChCAR TG BMDM were infected with low MOI of AdV expressing GFP or GFPPOP3 and transfected 48 h later with poly(dA:dT) or infected with MVA for 16 h and analyzed for secreted IL-1β by ELISA.

FIGS. 11a-e. POP3 interacts with AIM2 and IFI16 in BMDM.

FIGS. 12a-i. CD68-POP3 TG mice are impaired in AIM2-dependent and viral DNA-induced host defense in vivo.

FIGS. 15a-h. Inducible expression of POP1 is reduced in inflammatory disease. a, Immunohistochemical staining of CD68 (red) and POP1 (brown) in human lung tissue. Original magnification left: ×10 and right: ×40. b-d, POP1 mRNA expression (relative to control) in (b) leukocytes of adult critically ill (n=17), Gram negative septic, Gram positive septic or mixed septic (n=55) patients (Gene Expression Omnibus accession number GDS3085), (c) in whole blood drawn from pediatric healthy controls (n=18) and patients diagnosed with systemic inflammatory response syndrome (SIRS), sepsis or septic shock (n=209) (Gene Expression Omnibus accession number GSE13904), and (d) in whole blood drawn from healthy controls (n=23), CINCA (n=2) and MWS (n=5) patients (Gene Expression Omnibus accession number GSE40561). e-h, POP1, HMGB1 and ASC transcripts were measured by Real-time PCR in (e) LPS-treated hMΦ; (f) leukocytes from LPS infused human subjects; (g) ah anakinra pre-treated hMΦ, as indicated, before treatment with LPS for 24 h; (h) hMΦ treated with IL-1β for 4 h.

FIGS. 16a-d. POP1 inhibits the NLRP3 inflammasome in human macrophages. a, HEK293 cells were transfected to express POP1 and ASCPYD as indicated, followed by immunoblot analysis with antibody to POP1 or c-Myc as indicated. b, CLUSTAL-W sequence alignment for POP1 and ASCPYD with dark shaded residues representing identical and light shaded residues representing conserved amino acids. c, POP1 transcripts were measured by Real-time PCR in LPS-treated THP-1 cells; d, THP-1 cells stably expressing Myc-POP1 were analysed by qPCR for POP1 expression. Culture SN were analysed by ELISA for IL-1β release in untreated cells (Ctrl) or in response to crude LPS or nigericin treatment in LPS-primed cells.

FIGS. 17a-i. POP1 inhibits the NLRP3 inflammasome in human macrophages. a, THP-1 cells stably expressing GFP or GFP-POP1 were analysed by Real-time PCR for POP1 transcripts. b-c, Culture supernatants (SN) from THP-1 cells stably expressing GFP or GFP-POP1 were analysed for IL-1β release by ELISA (b) in untreated cells (Ctrl) or in response to nigericin or CPPD treatment or K+ depletion in LPS-primed cells; transfection of poly(dA:dT), flagellin, or MDP; or (c) LPS treatment, LPS transfection or incubation with LPS complexed with CTB. d, LPS primed THP-1 cells expressing GFP or GFP-POP1 were treated with nigericin and active caspase-1 determined by flow cytometry. e, LPS primed THP-1 cells expressing GFP or GFP-POP1 were treated with nigericin or CPPD crystals and released LDH in culture supernatants was quantified. f, THP-1 cells stably expressing shRNAs targeting POP1 or a scrambled Ctrl were analysed by Real-time PCR for POP1 transcripts and for IL-1β release in culture SN in untreated cells (Ctrl) or in response to LPS. g, Primary macrophages transfected with a scrambled Ctrl or POP1-specific siRNA were analysed for POP1 transcripts by Real-time PCR and culture SN for IL-1β and IL-18 in response to LPS. h, Immunoblot analysis of phosphorylated (p-) IκBα and β-tubulin in total cell lysates of THP-1 cells expressing GFP or GFP-POP1 treated for 30 and 60 min with LPS. i, Real-time PCR analysis of IL1B transcripts in above cells treated for 4 h with LPS. (b, left panel)

FIG. 22a-f. POP1 inhibits the NLRP3 inflammasome in mouse macrophages. a, Analysis of POP1 expression by flow cytometry in peripheral blood cell populations isolated from wild-type (WT) and CD68-POP1 transgenic (POP1) mice. b, Western Blot of POP1 expression in BMDM. c, Interaction of GST-POP1 with endogenous ASC in BMDM total cell lysates (TCL) using GST as negative control and showing 10% TCL as input. d, Immunoblot analysis of ASC polymerization in WT and POP1 BMDM left untreated or treated with LPS/ATP after cross linkage of pellets (P) and in TCL. e, Immunoblot analysis of caspase-1 and IL-1β in culture supernatants (SN) of LPS-primed WT and POP1 BMDM treated with ATP, showing pro-caspase-1 expression in TCL for normalization. f, Flow Cytometric quantification of active caspase-1 in WT and POP1 BMDM in response to LPS/ATP; data are representative of three (a), two (c, d-f) and four (b) replicates.

FIGS. 24a-e. POP1 inhibits IL-1β release in mouse macrophages. a-d, Analysis of culture supernatants (SN) for IL-1β, IL-18, IL-1α and TNF-α by ELISA in (a, b) LPS primed and ATP treated (a) WT and CD68-POP1 transgenic (POP1) BMDM; (b) WT, POP1, ASC-/- and NLRP3-/- BMDM; (c) LPS primed WT and POP1 BMDM cultured in K+ depleted medium; and (d) WT and POP1 PM treated with LPS/ATP or transfected with flagellin or poly(dA:dT). e, LPS primed WT and POP1 BMDM were treated with nigericin or CPPD crystals and released LDH in culture supernatants was quantified.

FIGS. 25a-c. POP1 does not affect LPS mediated cell signalling and transcription of IL1b and IL18. a, CLUSTAL-W sequence alignment for human and mouse ASCPYD with dark shaded residues representing identical and light shaded residues representing conserved amino acids. b, Immunoblot analysis of total and phosphorylated (p-) IκBα, Jnk, p38 and p42/44 and β-tubulin in total cell lysates of wild-type (WT) and CD68-POP1 (POP1) BMDMs treated for the indicated times with LPS, analyzed with 'pan-specific' and phosphorylation-specific antibodies. c, Real-time PCR analysis of Il1b and Il18 transcripts in WT and POP1 BMDMs treated for 4 h with LPS.

FIGS. 26a-i. Monocyte/macrophage-specific expression of POP1 ameliorates LPS-induced peritonitis and CAPS. a, Representative in vivo image of MPO activity in mice 3 h after i.p. injection of PBS or E. coli LPS (2.5 mg/kg body weight). The range of the luminescence radiance is 1195 to 20677 photons/sec/cm2/sr. Image quantification of the MPO luminescent signal in wild-type (WT) (n=6) and CD68-POP1 transgenic (TG) (n=5) mice. b, c, Endotoxic shock was induced by i.p. injection of *E. coli* LPS (20 mg/kg body weight) and (b) body temperature and (c) survival was determined in WT (n=5) and CD68-POP1 TG (n=5) mice. d, ELISA of IL-1β, IL-18 and TNF-α in the serum of WT (n=5) and CD68-POP1 TG (n=5) mice 3 h after i.p. *E. coli* LPS challenge (20 mg/kg body weight). e, Representative image of (left) 3 d and (right) 8 d old (top) NLRP3A350V/+ CreL CD68-POP1 and (bottom) NLRP3A350V/+ CreL mice. Arrows point to inflammatory skin abscesses. f, H&E staining of skin sections from above mice at day 8. Scale bar 100 μm (original) and 10 μm (magnification). g, Serum IL-1β levels in 8 d old NLRP3A350V/+ CreL (n=4) and NLRP3A350V/+ CreL CD68-POP1 (n=5) mice. h, Body weight of WT (n=15), NLRP3A350V/+ CreL CD68-POP1 (n=11) and NLRP3A350V/+ CreL (n=11) mice. i, survival of WT (n=11), NLRP3A350V/+ CreL CD68-POP1 (n=10) and NLRP3A350V/+CreL (n=8) mice.

FIGS. 34a-b. POP3 is stabilized by MG132 IFN. (A,B) Cells were infected with a POP3 expressing adenovirus and treated with MG132 or IFN and analyzed by immunoblot.

FIG. 35. hMΦ were infected with a GFP-POP3 AdV or ctrl, stained for endogenous IFI16 and DNA and analyzed by microscopy.

DEFINITIONS

Figure 1A:
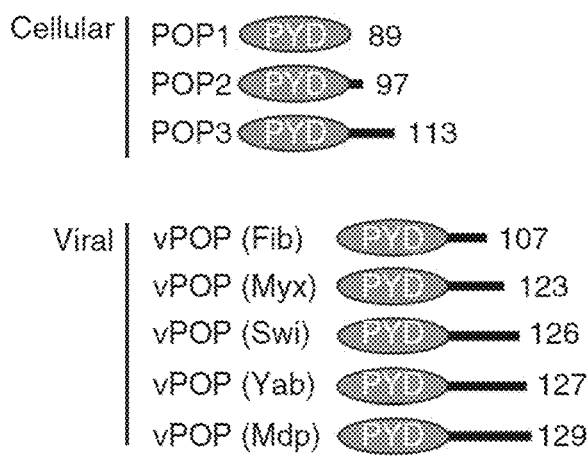

As used herein, the term "inflammasome" refers to a multiprotein complex comprising caspase 1, PYCARD, NALP and sometimes caspase 5 (a.k.a. caspase 11 or ICH-3). Inflammasomes are expressed in myeloid cells and are a component of the innate immune system. The exact composition of an inflammasome varies and depends on the activator which initiates inflammasome assembly. Inflammasomes promote the maturation of the inflammatory cytokines Interleukin 1β (IL-1β) and Interleukin 18 (IL-18). Inflammasomes are responsible for activation of inflammatory processes, and have been shown to induce cell pyroptosis, a process of programmed cell death distinct from apoptosis.

As used herein, the term "autoimmune disease" refers generally to diseases which are characterized as having a component of self-recognition. Examples of autoimmune diseases include, but are not limited to, Autoimmune hepatitis, Multiple Sclerosis, Systemic Lupus Erythematosus, Myasthenia Gravis, Type I diabetes, Rheumatoid Arthritis, Psoriasis, Hashimoto's Thyroiditis, Grave's disease, Ankylosing Spondylitis Sjogrens Disease, CREST syndrome, Scleroderma, etc. Most autoimmune diseases are also chronic inflammatory diseases. This is defined as a disease process associated with long-term (>6 months) activation of inflammatory cells (e.g., leukocytes). The chronic inflammation leads to damage of patient organs or tissues. Many other diseases are inflammatory disorders, but are not know to have an autoimmune basis. For example, Atherosclerosis, Congestive Heart Failure, Crohn's disease, Colitis (e.g., Ulcerative Colitis), Polyarteritis nodosa, Whipple's Disease, Primary Sclerosing Cholangitis, etc. The clinical manifestations of autoimmune and inflammatory diseases range from mild to severe. Mild disease encompasses symptoms that may be function-altering and/or comfort-altering, but are neither immediately organ-threatening nor life-threatening. Severe disease entails organ-threatening and/or life-threatening symptoms. For example, severe autoimmune disease is often associated with clinical manifestations such as nephritis, vasculitis, central nervous system disease, premature atherosclerosis or lung disease, or combinations thereof, which require aggressive treatment and may be associated with premature death.

As used herein, the term "peptide" refers a short polymer of amino acids linked together by peptide bonds. In contrast to other amino acid polymers (e.g., proteins, polypeptides, etc.), peptides are of about 50 amino acids or less in length. A peptide may comprise natural amino acids, non-natural amino acids, and/or modified amino acids. A peptide may be a subsequence of naturally occurring protein or a non-natural sequence.

As used herein, the term "mutant peptide" refers to a variant of a peptide having a distinct amino acid sequence from the most common variant occurring in nature, referred to as the "wild-type" sequence. A mutant peptide may be a subsequence of a mutant protein or polypeptide (e.g., a subsequence of a naturally-occurring protein that isn't the most common sequence in nature), or may be a peptide that is not a subsequence of a naturally occurring protein or polypeptide. For example, a "mutant POP3 peptide" may be a subsequence of a mutant version of POP3 or may be distinct sequence not found in naturally-occurring POP3 proteins.

As used herein, the term "synthetic peptide" refers to a peptide having a distinct amino acid sequence from those found in natural peptides and/or proteins. A synthetic protein is not a subsequence of a naturally occurring protein, either the wild-type (i.e., most abundant) or mutant versions thereof. For example, a "synthetic POP1" ("sPOP1 peptide") is not a subsequence of naturally occurring POP1. A "synthetic peptide," as used herein, may be produced or synthesized by any suitable method (e.g., recombinant, chemical synthesis, enzymatic synthesis, etc.).

The term "peptide mimetic" or "peptidomimetic" refers to a peptide-like molecule that emulates a sequence derived from a protein or peptide. A peptide mimetic or peptidomimetic can contain amino acids and/or non-amino acid components. Examples of peptidomimitics include chemically modified peptides, peptoids (side chains are appended to the nitrogen atom of the peptide backbone, rather than to the α-carbons), β-peptides (amino group bonded to the β carbon rather than the α carbon), etc.

As used herein, the term "sequence identity" refers to the degree to which two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) have similar polymer sequences. For example, similar amino acids are those that share the same biophysical characteristics and can be grouped into the families, e.g., acidic (e.g., aspartate, glutamate), basic (e.g., lysine, arginine, histidine), non-polar (e.g., alanine, valine, leucine, isoleucine, proline, phenylalanine, methionine, tryptophan) and uncharged polar (e.g., glycine, asparagine, glutamine, cysteine, serine, threonine, tyrosine). The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

As used herein, the term "subject" broadly refers to any animal, including but not limited to, human and non-human animals (e.g., dogs, cats, cows, horses, sheep, poultry, fish, crustaceans, etc.). As used herein, the term "patient" typically refers to a subject that is being treated for a disease or condition.

As used herein, the term "effective amount" refers to the amount of a composition sufficient to effect beneficial or desired results. An effective amount can be administered in one or more administrations, applications or dosages and is not intended to be limited to a particular formulation or administration route.

As used herein, the terms "administration" and "administering" refer to the act of giving a drug, prodrug, or other agent, or therapeutic treatment to a subject or in vivo, in vitro, or ex vivo cells, tissues, and organs. Exemplary routes of administration to the human body can be through space under the arachnoid membrane of the brain or spinal cord (intrathecal), the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

As used herein, the terms "co-administration" and "co-administering" refer to the administration of at least two agent(s) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

As used herein, the term "treatment" means an approach to obtaining a beneficial or intended clinical result. The beneficial or intended clinical result may include alleviation of symptoms, a reduction in the severity of the disease, inhibiting a underlying cause of a disease or condition, steadying diseases in a non-advanced state, delaying the progress of a disease, and/or improvement or alleviation of disease conditions.

As used herein, the term "pharmaceutical composition" refers to the combination of an active agent with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintegrants (e.g., potato starch or sodium starch glycolate), and the like. The compositions also can include stabilizers and preservatives. For examples of carriers, stabilizers and adjuvants, see, e.g., Martin, Remington's Pharmaceutical Sciences, 15th Ed., Mack Publ. Co., Easton, Pa. (1975), incorporated herein by reference in its entirety.

DETAILED DESCRIPTION

Provided herein are compositions and methods for modulation of immune response via PYRIN domain-only proteins POP1, POP2, and/or POP3. In particular, POP1, POP2, and/or POP3 are inhibited to enhance an immune response (e.g., to treat or prevent infection), or POP1, POP2, and/or POP3 are administered or activated to reduce an immune response (e.g., to treat or prevent autoimmune or inflammatory disease).

Although inflammasome-produced cytokines are necessary for host defense and metabolic health, excessive and uncontrolled cytokine production contributes to pathological inflammation and autoinflammatory diseases. Hence, factors that promote a balanced inflammasome response are essential for maintaining homeostasis. However, the regulation of inflammasomes has been poorly understood. Experiments conducted during development of embodiments described herein indicate that the type I IFN-inducible POP3 is one of the proteins that function to maintain a balanced inflammasome response in humans by specifically inhibiting ALR inflammasome assembly in response to immunogenic DNA. While other POPs directly interact with the inflammasome adaptor ASC (Dorfleutner A, et al. Infect Immun 2007; 75:1484-1492; Stehlik et al. Biochem J. 2003; 373:101-113; herein incorporated by reference in their entireties), POP3 interacts with the PYD of ALRs and thereby prevents recruitment of ASC. Although, it was found that recombinant POP3 interacted with NLRP3 in vitro, functional impairment of NLRP3-dependent inflammasome formation and activation was not observed in vitro and in vivo. POP3 was not recruited to the endogenous ligand-induced NLRP3-ASC complex, but was recruited to MVA-induced endogenous AIM2, where it prevented ASC recruitment. Thus, POP3 evolved as a specific ALR inflammasome regulator.

Experiments further revealed that the human HIN-200 cluster is more complex than previously described and differs from mice. However, mice may employ an alternative mechanism for ALR inflammasome regulation through the DNA-binding HIN-200 family member p202, which lacks the PYD and is not encoded in humans, but may function as an antagonist for AIM2 in mice (Roberts T L, et al. Science. 2009; 323:1057-60; herein incorporated by reference in its entirety). However, p202 is barely detectable in C57BL/6 mice, but is highly expressed in BALB/c and NZB mouse strains. This is contemplated to be an important influence as to why POP3 expression in C57BL/6 mice was able to drastically alter the immune response upon MCMV infection using 'humanized' C57BL/6 mice. Two proteins encoding only a PYD are predicted in mice within the HIN-200 cluster, which both lack a human ortholog. Pydc3 (Ifi208) is predicted to encode only a PYD, but is significantly larger than POPs and might encode a HIN-200 domain, according to expressed sequence tags (Ludlow et al. Exp Cell Res. 2005; 308:1-17; Cridland J A, et al. BMC Evol Biol. 2012; 12:140; herein incorporated by reference in their entireties). Two predicted Pydc4 alternative transcripts encode only a PYD, but the longest transcript encodes a 586 aa protein, which is 95.2% identical to PYDC3. However, neither gene shows similarity with POP3 and no expression data or functional data are available. Thus, Aim2b, a predicted Aim2 splice form in mice, might most closely resemble the POP3 function in mice. Similar to the human HIN-200 locus, the rat HIN-200 chromosomal region is also predicted to encode four HIN-200 proteins (Rhin2, Rhin3, Rhin4, Aim2) and the putative POP Rhin5, which is twice the size of POP3 and shares less than 14% sequence identity and also lacks any expression data. Contrary to mice, it is speculated that humans evolved POP3 to interfere with ALR inflammasome assembly.

The type I IFN-responsiveness further distinguishes POP3 from other POP family members. Thus, POP3 represents one of the type I IFN-inducible proteins that antagonizes IFN-γ in macrophages and inflammasome activation (Guarda G, et al. Immunity. 2011; 34:213-23; herein incorporated by reference in its entirety), and contributes to the anti-inflammatory and immunosuppressive functions of type I IFNs (Gonzalez-Navajas J M, Lee J, David M, Raz E. Immunomodulatory functions of type I interferons. Nat Rev Immunol; herein incorporated by reference in its entirety). Aim2$^{-/-}$ BMDM show elevated IFN-β production (Fernandes-Alnemri T, et al. Nat Immunol. 2010; 11:385-393; Rathinam V A, et al. The AIM2 inflammasome is essential for host defense against cytosolic bacteria and DNA viruses. Nat Immunol. 2010; 11:395-402; herein incorporated by reference in their entireties). It was observed that POP3 silencing, which increases AIM2 signaling, also reduces IFN-β production, and accordingly, POP3 expression in THP-1 cells and BMDM promotes IFN-β production. Thus, besides promoting its own IFN-β-dependent production, experiments indicate that POP3 shifts the immune response from an inflammasome-dependent pro-inflammatory cytokine production to anti-inflammatory IFN-β production, thereby further blunting IL-1β and IL-18 signaling through upregulation of IL-1RA and IL-18BP (Kaser A, et al. Clin Exp Immunol. 2002; 129:332-8; Sciacca et al. J Neurovirol. 2000; 6 (Suppl 2):S33-7, herein incorporated by reference in their entireties). A similar mechanism has been proposed for LRRFIP2, which inhibits NLRP3 inflammasome activation by recruiting the pseudo caspase-1 substrate Flightless-I (Jin J, et al. Nat Commun. 2013; 4:2075: herein incorporated by reference in its entirety), but also functions as a cytosolic DNA sensor, which promotes type I IFN production (Yang P, et al. Nat Immunol. 2010; 11:487-94; herein incorporated by reference in its entirety). The IFN-β-inducible expression pattern of POP3 as an early and late response gene was similarly observed in CD68-POP3 TG mice. Although, POP3 is lacking from mice, macrophage-specific TG expression revealed that POP3 is nevertheless functional in mice.

POP3 is protein exhibiting inflammasome inhibitory function. POP3 inhibits release of IL-1β and type I interferon. POP3 interacts with the central inflammasome adaptor ASC and thereby blocks the signaling from Nod-like receptors (NLRs), and with two pattern recognition receptors of the AIM2-like receptor family, namely AIM2 and IFI16. POP3 is a small 13 kDa protein and delivery of a recombinant protein into macrophages shows inhibitory activity. In some embodiments, provided herein are POP3 peptides, polypeptides, and/or peptidomimetics.

POP3 is a novel regulator for cytosolic pattern recognition receptors of the NLR and ALR family Therefore it is significant for blocking excessive production of cytokines in inflammatory disease. IL-1β is a very potent cytokine, and excessive production of it is linked to many inflammatory and autoimmune diseases. Many autoimmune diseases also show a type I interferon signature and type I interferon is required for inflammasome activation. Experiments were conducted during development of embodiments of the present invention that indicate POP3 may be employed to specifically block IL-1β generation or to neutralize POP3 to boost immune responses for adjuvant activity or to clear infections. Since POP3 most potently interacts with ALRs, which sense cytosolic DNA, which is present during autoinnnune disease and bacterial and viral infections, both, neutralizing as well as mimicking POP3 provides useful therapies.

NLRP3 inflammasome regulatory proteins exist to maintain a proper level of activity and in particular, to limit its activity during the resolution phase of this response. Experiments were conducted during development of embodiments described herein to determine if POP1 is one of these proteins. The NLRP3 inflammasome and its mediators are tightly regulated at multiple steps, ranging from transcription to posttranslational modification of individual components, yet the essential step is the assembly of the NLRP3 inflammasome platform. Recent evidence supports a model where NLRP3PYD binding to ASCPYD induces an initial nucleation event of the ASCPYD and subsequent prion-like ASCPYD self-polymerization (Lu et al. Cell 156, 1193-206 (2014); Cai et al. Cell 156, 1207-22 (2014); Franklin et al. Nat Immunol 15, 727-37 (2014); herein incorporated by reference in their entireties). Thus, the PYD present in NLRP3 and ASC plays a crucial role in inflammasome assembly. Experiments conducted during development of embodiments described herein support such a model, where POP1 binds to the ASCPYD, which prevents ASCPYD interaction with active NLRP3PYD, and thus the crucial nucleation event for ASC oligomerization, as determined by non-reversible crosslinking. However, in spite of binding to the ASCPYD, POP1 did not prevent ASC self-polymerization. Upon overexpression of both proteins, the high expression levels of ASCPYD are sufficient to promote self-polymerization through the prion activity of the ASCPYD. Each ASCPYD interacts with two other ASCPYD molecules within filaments (Lu et al. Cell 156, 1193-206 (2014); Vajjhala et al. J Biol Chem 287, 41732-41743 (2012); herein incorporated by reference in their entireties), and since the residues necessary for ASCPYD polymerization are conserved in POP1, it is contemplated that POP1 could replace ASCPYD within filaments, without providing the CARD for caspase-1 nucleation, polymerization and activation. Accordingly, ASC particle induced IL-1β release, which was prevented by POP1 expression. However, mixed particles composed of ASC and POP1 were inactive. Thus, POP1 expression not only prevents inflammasome assembly and cytokine release, but also the propagation of secondary inflammasome responses to bystander cells. Experiments conducted during development of embodiments described here in demonstrate slightly enhanced ASCPYD self-interaction in the presence of POP1, which indicated weak nucleation activity, similar to the NLRP3PYD, which can also nucleate ASCPYD polymerization, albeit significantly less efficient than full length, active NLRP36. Since the NLRP3PYD and POP1 interact through the same motif with the ASC PYD, a weak nucleation effect of POP1 under these in vitro conditions is possible and may also explains the previously observed positive effect of overexpressed POP1 on IL-1β release in inflammasome reconstitution assays (Stehlik et al. J. Immunol 171, 6154-63 (2003); herein incorporated by reference in its entirety). However, similar to the NLRP3PYD6, also POP1 does not have intrinsic prion activity, since POP1 does not form filaments when overexpressed on its own (Stehlik et al. Biochem. J 373, 101-113 (2003); herein incorporated by reference in its entirety).

Excessive and uncontrolled release of inflammasome mediators contribute to autoinflammatory and auto-immune disease (Strowig et al. Nature 481, 278-86 (2012); herein incorporated by reference in its entirety) and blocking in particular IL-1β has been proven beneficial in various inflammatory diseases in human and mice (Dinarello et al. Blood 117, 3720-32 (2011); herein incorporated by reference in its entirety). Furthermore, oligomeric ASC particles have been identified in CAPS and pulmonary disease patients (Franklin et al. Nat Immunol 15, 727-37 (2014); Baroja-Mazo et al. Nat Immunol 15, 738-48 (2014); herein incorporated by reference in their entireties). However, in spite of the tight regulation of this response, even a single point mutation in NLRP3 can drive excessive systemic inflammation (Hoffman et al. J Biol Chem 286, 10889-96 (2011); herein incorporated by reference in its entirety), indicating that also inflammasome regulatory mechanisms may be impaired. In agreement with this concept, POP1 expression was observed in lung tissue from healthy subjects, while CAPS and sepsis patients expressed significantly lower POP1 compared to healthy controls. This indicates that in addition to uncontrolled activation of NLRP3, also the subsequent recruitment of ASC, ASC oligomerization and consequently extracellular release of oligomeric ASC danger particles proceeds continuously, without a proper POP1-mediated shutdown mechanism.

Experiments conducted during development of embodiments described herein identified POP1 and POP3 as inflammasome inhibitors, blockers of signaling from Nod-like receptors (NLRs), and capable of blocking cytokine production (e.g., excessive cytokine production), for example production of IL-1β and type I interferon. As such, POP1 and/or POP3 are useful for the treatment or prevention of diseases and conditions in which overactivity of inflammasomes or excessive cytokine production are causative or symptomatic (e.g., autoimmune diseases, inflammatory diseases, etc.).

Experiments conducted during development of embodiments described herein identified POP2 as an inflammasome inhibitor. As such, POP2 is useful for the treatment or prevention of diseases and conditions in which overactivity of inflammasomes or excessive cytokine production are causative or symptomatic (e.g., autoimmune diseases, inflammatory diseases, etc.). Further, inhibition of POP2 activity us useful in the treatment or prevention of conditions (e.g., infection) in which an enhanced immune response is desired.

In some embodiments, POP1, POP2, and/or POP3 are administered to a cell or subject. In some embodiments, POP1, POP2, and/or POP3 polypeptide, peptide, or peptidomimetic is administered. In some embodiments, a composition that enhances the activity of POP1 and/or POP3 is administered. In some embodiments, a composition that colocalizes POP1 and/or POP3 with inflammasomes is administered.

In some embodiments, a protein, polypeptide, or peptide is provided that has at least 60% sequence identity with POP1 (e.g., 60%, 65%, 70%, 75%, 80%, 85%, 90%, 95%, 98%, 99%). In some embodiments, a protein, polypeptide, or peptide is provided that has less than 100% sequence identity with POP1. In some embodiments, a protein, polypeptide, or peptide is provided that has at least 60% sequence similarity with POP1 (e.g., 60%, 65%, 70%, 75%, 80%, 85%, 90%, 95%, 98%, 99%). In some embodiments, a protein, polypeptide, or peptide is provided that has at least 60% (e.g., 60%, 65%, 70%, 75%, 80%, 85%, 90%, 95%, 98%, 99%) with a portion of POP1 at least 8 amino acids in length (e.g., 8 amino acids, 9 amino acids, 10 amino acids, 11 amino acids, 12 amino acids, 13 amino acids, 14 amino acids, 15 amino acids, 16 amino acids, 17 amino acids, 18 amino acids, 19 amino acids, 20 amino acids, 25 amino acids, 30 amino acids, 35 amino acids, 40 amino acids, 45 amino acids, 50 amino acids, or more, or any ranges therein (e.g., 15-25 amino acids)). In some embodiments, a protein, polypeptide, or peptide is provided that exhibits inflammasome inhibitory activity.

In some embodiments, a protein, polypeptide, or peptide is provided that has at least 60%سequence identity with POP2 (e.g., 60%, 65%, 70%, 75%, 80%, 85%, 90%, 95%, 98%, 99%). In some embodiments, a protein, polypeptide, or peptide is provided that has less than 100% sequence identity with POP2. In some embodiments, a protein, polypeptide, or peptide is provided that has at least 60% sequence similarity with POP2 (e.g., 60%, 65%, 70%, 75%, 80%, 85%, 90%, 95%, 98%, 99%). In some embodiments, a protein, polypeptide, or peptide is provided that has at least 60% (e.g., 60%, 65%, 70%, 75%, 80%, 85%, 90%, 95%, 98%, 99%) with a portion of POP2 at least 8 amino acids in length (e.g., 8 amino acids, 9 amino acids, 10 amino acids, 11 amino acids, 12 amino acids, 13 amino acids, 14 amino acids, 15 amino acids, 16 amino acids, 17 amino acids, 18 amino acids, 19 amino acids, 20 amino acids, 25 amino acids, 30 amino acids, 35 amino acids, 40 amino acids, 45 amino acids, 50 amino acids, or more, or any ranges therein (e.g., 15-25 amino acids)). In some embodiments, a protein, polypeptide, or peptide is provided that exhibits inflammasome inhibitory activity.

In some embodiments, a protein, polypeptide, or peptide is provided that has at least 60% sequence identity with POP3 (e.g., 60%, 65%, 70%, 75%, 80%, 85%, 90%, 95%, 98%, 99%). In some embodiments, a protein, polypeptide, or peptide is provided that has less than 100% sequence identity with POP3. In some embodiments, a protein, polypeptide, or peptide is provided that has at least 60% sequence similarity with POP3 (e.g., 60%, 65%, 70%, 75%, 80%, 85%, 90%, 95%, 98%, 99%). In some embodiments, a protein, polypeptide, or peptide is provided that has at least 60% (e.g., 60%, 65%, 70%, 75%, 80%, 85%, 90%, 95%, 98%, 99%) with a portion of POP3 at least 8 amino acids in length (e.g., 8 amino acids, 9 amino acids, 10 amino acids, 11 amino acids, 12 amino acids, 13 amino acids, 14 amino acids, 15 amino acids, 16 amino acids, 17 amino acids, 18 amino acids, 19 amino acids, 20 amino acids, 25 amino acids, 30 amino acids, 35 amino acids, 40 amino acids, 45 amino acids, 50 amino acids, or more, or any ranges therein (e.g., 15-25 amino acids)). In some embodiments, a protein, polypeptide, or peptide is provided that exhibits inflammasome inhibitory activity.

In some embodiments, exogenous POP1, POP2, POP3, fragments thereof, or peptides or polypeptides having 60-100% sequence identity thereto (e.g., and maintaining POP1, POP2, and/or POP3 activity) are administered to a cell or subject. In other embodiments, POP1, POP2 and/or POP3 activating agents (e.g., peptides, small molecules, etc.) are administered to a cell or subject. In some embodiments, administration of the foregoing results in inflammasome inhibitions, inhibition of cytokine production, inhibition of IL-1β release, inhibition of type I interferon release, blocking signaling from NLRs, etc.

In some embodiments, a composition is administered that inhibits inflammasome activity. In some embodiments, a composition is administered that inhibits inflammasome assembly.

Experiments conducted during development of embodiments described herein identified POP1 and POP3 as inflammasome inhibitors, blockers of signaling from Nod-like receptors (NLRs), and capable of blocking cytokine production (e.g., excessive cytokine production), for example production of IL-1β and type I interferon. As such, inhibition of POP1 and/or POP3 is useful for the treatment or prevention of diseases and conditions in which inflammasomes and/or cytokine production provide treatment (e.g., bacterial or viral infection). In some embodiments, one or more inhibitors (e.g., anti-POP1 antibody, anti-POP3 antibody, fragments thereof) of POP1 and/or POP3 (e.g., anti-POP1 antibody, anti-POP3 antibody, fragments thereof) are administered (e.g., to a cell, tissue, subject, etc.) for the treatment or prevention of infection (e.g., bacterial or viral).

Experiments conducted during development of embodiments described herein identified POP2 as an inflammasome inhibitor. As such, POP2 is useful for the treatment or prevention of diseases and conditions in which overactivity of inflammasomes or excessive cytokine production are causative or symptomatic (e.g., autoimmune diseases, inflammatory diseases, etc.). Further, inhibition of POP2 activity us useful in the treatment or prevention of conditions (e.g., infection) in which an enhanced immune response is desired.

In some embodiments, a POP1, POP2, and/or POP3 inhibitor is a small molecule, peptide, polypeptide, protein, antibody, nucleic acid, etc. In some embodiments, a POP1, POP2, and/or POP3 binding agent (e.g., antibody, antibody fragment, aptamer, etc.) is administered that neutralizes POP1, POP2, and/or POP3 activity. In some embodiments, such a binding agent recognizes an epitope displayed by POP1, POP2, and/or POP3. In some embodiments, binding agents (e.g., antibody, antibody fragment, aptamer, etc.) capable of binding and/or neutralizing POP1, POP2, and/or POP3 are provided. In some embodiments, an antibody is a humanized antibody, antibody fragment, multivalent antibody, monoclonal antibody, neutralizing antibody, or any suitable combination thereof.

In some embodiments, compositions comprise a POP1, POP2, and/or POP3 neutralizing antibody or antibody fragment. The term "neutralizing antibody" or "antibody that neutralizes" refers to an antibody that reduces at least one activity of a polypeptide comprising the epitope to which the antibody specifically binds. In certain embodiments, a neutralizing antibody reduces an activity in vitro and/or in vivo.

In some embodiments, a composition is administered that promotes inflammasome activity. In some embodiments, a composition is administered that promotes inflammasome assembly.

In some embodiments, methods are provided screening test agents (e.g., pharmaceuticals, drugs, peptides, antibodies, aptamers, or other test agents) for one or more activities described herein (e.g., POP1, POP2, or POP3 inhibition; POP1, POP2, or POP3 activation; POP1, POP2, or POP3 localization; inflammasome inhibition; blocking NLR signaling; inhibiting cyctokine production; etc.). In some embodiments, test agents (e.g., pharmaceuticals, drugs, peptides, antibodies, aptamers, or other test agents) identified using screening assays of the present invention find use in the treatment of autoimmune diseases, inflammatory diseases, infections, etc.

In some embodiments, screening assays for assessing cellular behavior or function are provided. For example, the response of cells, tissues, or subject to interventions (e.g., POP1/POP2/POP3 inhibition, POP1/POP2/POP3 administration, POP1/POP2/POP3 activation, etc.) may be monitored by assessing, for example, cellular functions using animal or cell culture models. Such assays find particular use for characterizing, identifying, validating, selecting, optimizing, or monitoring the effects of agents (e.g., small molecule-, peptide-, antibody-, nucleic acid-based drugs, etc.) that find use in the treatment of diseases and conditions described herein (e.g., autoimmune diseases, inflammatory diseases, infections, etc.).

EXPERIMENTAL

Example 1

The PYRIN Domain-Only Protein POP3 Inhibits AIM2-Like Receptor Inflammasomes and Regulates Responses to DNA Virus Infections Mice pCD68-POP3 was generated by replacing CAT in pCAT-Basic containing the human CD68 promoter and the macrophage-specific IVS-1 enhancer with POP3 and flanking the cassette with AatII restriction sites. The AatII fragment was excised, purified and B6.TgN(CD68-POP3) TG mice were generated by pronuclear injection into C57BL/6 embryos. Two lines were initially analyzed and subsequently a single line was used for most experiments and genotyping was outsourced to Transnetyx. B6.TgN (UbiC-hCAR) TG mice were generated by pronuclear injection of a BglII fragment from pUBI containing the ubiquitin C promoter/intron41 and the human coxsackie and adenovirus receptor (hCAR) with deleted cytoplasmic domain (hCARΔcyt)40. Mice were housed in a specific pathogen-free animal facility and all experiments were performed on age and gender-matched 8-12 weeks old mice conducted according to procedures approved by the Northwestern University Committee on Use and Care of Animals.

Macrophage Isolation, Culture and Transfection hMΦ were isolated from healthy donor blood after obtaining informed consent under a protocol approved by Northwestern University Institutional Review Board by Ficoll-Hypaque centrifugation (Sigma) and countercurrent centrifugal elutriation in the presence of 10 μg/ml polymyxin B using a JE-6B rotor (Beckman Coulter), as described51 and transfected in 24-well dishes (2.5×105 cells) with 120 nM siRNA duplexes (F2/virofect; Targeting Systems) and analyzed 72 hr posttransfection (POP3 stealth siRNA sense strand: 5'-CAUGGCAUUUCUGGGAAUG-CAUGUU-3' (SEQ ID NO: 1), POP3 siRNA #2 sense strand: 5'-GAGCAGGAAACGGUAUAUGUGGGA-3' (SEQ ID NO: 2), and Ctrl stealth siRNA, Invitrogen) (Khare S, et al. Immunity. 2012; 36:464-76; herein incorporated by reference in its entirety). BMDM were flushed from femurs and tibia and differentiated in L929-conditioned medium (25%) in DMEM medium supplemented with 10% heat inactivated FCS (Invitrogen) and analyzed after 7 days. Resting or elicited peritoneal macrophages (PM) were isolated by peritoneal lavage before or 3-5 days after i.p. injection of 1 ml 4% aged thioglycollate medium. THP-1 cells were obtained from ATCC and were routinely tested for mycoplasma contamination. THP-1 cells were stably transduced with pLEX-based lentiviral particles. hMΦ, THP-1 cells, BMDM and PM were treated for the indicated times with 600 ng/mL E. coli LPS (0111:B4, Sigma) or pre-treated with ultra-pure E. coli LPS (0111:B4; Invivogen) (100 ng/mL), MSU (400 ng/mL; Invivogen), mouse and human IFN-β (1500 U/mL; Millipore), MG132 (10 μM; Calbiochem), mIL-1Ra (100 ng/mL; R&D Systems) or recombinant IL-1Ra (anakinra, 10 mg/mL, Amgen). Cells were transfected with poly(dA:dT) (2 ng/mL; Sigma), MDP (20 ug/mL; Invivogen), *Salmonella thyphimurium* flagellin (140 ng/mL; Invivogen) and *Bacillus anthracis* Lethal toxin and protective antigen (1 ug/mL; List Biological Laboratories) using Lipofectamine 2000 (Invitrogen). Where indicated, cells were pulsed for 20 min with ATP (5 mM; Sigma) or treated for 45 min with nigericin (5 µM).

Virus Preparation

Recombinant adenovirus was generated by cloning GFP or GFP-POP3 into pShuttle, recombination with pAdEasy in *E. coli* BJ5183 and purification from HEK293N cells on a caesium chloride gradient. Lentiviral particles were generated in HEK293T-Lenti cells (Clontech) transfected with pLEX containing GFP or GFP-POP3 and the packaging plasmids pMD.2G and psPAX2 (Addgene plasmids 12259 and 12260). Murine cytomegalovirus (MCMV, Smith strain, ATCC #VR-1399) was obtained from the American Type Culture Collection (ATCC) and propagated in mouse embryo fibroblast SG-1 cells (ATCC #CRL-1404) for cell-based experiments and passaged twice for 2 weeks each, in the salivary glands of 6-8 week-old BALB/c mice after i.p. injection of 1.5×105 PFU/mL MCMV. Mice were euthanized and salivary glands collected, homogenized in HBSS, clarified and the viral titer determined by plaque formation assay and a Taqman qPCR assay based on MCMV iE and glycoprotein B (Invitrogen), using a MCMV standard curve and stored in aliquots at −80° C. Non-infected clarified salivary gland homogenates were used for mock infection. 2.5×105 macrophages were infected with 1×105 PFU/well in 24-well plates. Vaccinia virus (MVA, modified Vaccinia virus Ankara, ATCC #VR-1508) was obtained from ATCC and amplified in hamster fibroblast BHK-21 cells (ATCC #CCL-10). MVA titer was determined by a plaque-forming assay using BHK-21 cells. 2.5×105 macrophages were infected with 1×106 PFU/well in 24-well plates. Kaposi's Sarcoma-associated herpes virus (KSHV) lytic cycle was induced from BCBL-1 cells by supplementing media with TPA (20 ng/mL). KSHV-containing culture SN was collected after 96 h, clarified by centrifugation (330×g for 5 min followed by centrifugation at 1540×g for 30 min) and filtered through 0.45 µm pore size filters. KSHV was subsequently concentrated by ultracentrifugation at 20,000 rpm for 90 min (SW28 rotor, 4° C.). Viral pellets were resuspended in EBM2 medium (Lonza), 0.45 µm filtered, and titered on the endothelial cell line iHMVEC52. KSHV was used to infect 2.5×105 macrophages at 1.2×105 IU/24-well.

Plasmids pCDNA3-based expression constructs for ASC, POP1 and POP2 are described in, for example, Dorfleutner A, et al. Virus Genes. 2007; 35:685-694; Dorfleutner A, et al. Infect Immun 2007; 75:1484-1492; Stehlik et al. Biochem J. 2003; 373:101-113; Khare S, et al. Immunity. 2012; 36:464-76; Bryan et al. J Inflamm (Lond) 2010; 7:23; Bryan et al. J Immunol. 2009; 182:3173-82; herein incorporated by reference in their entireties). POP3 (Acc. No.: KF562078), AIM2, AIM2-PYD, IFI16, IFI16-PYD, IFIX, IFIX-PYD, MNDA, MNDA-PYD, were generated by standard PCR from cDNAs and expressed sequence tags (EST) (Open Biosystems) and cloned in pcDNA3, pLEX or pShuttle with N-terminal myc, HA, Flag, GFP or RFP tags.

Immunoblot Analysis, Immunoprecipitation and Immunohistochemistry

Rabbit polyclonal and mouse monoclonal POP3 antibodies were custom raised (KLH-conjugated-CGSPS-SARSVSQSRL (SEQ ID NO: 63)), rabbit polyclonal antibody to ASC (Chemicon clone 2E1-7 and custom), mouse monoclonal antibody to ASC (custom), mouse polyclonal antibody to caspase-1 (Santa Cruz Biotech clone M-20), mouse monoclonal antibody to hCAR (Santa Cruz Biotech clone Mab.E[mh1]), mouse monoclonal antibody to GFP (Santa Cruz Biotech clone B-2), mouse monoclonal antibody to dsRED (Santa Cruz Biotech clone F-9), mouse monoclonal antibody to myc (Roche and Santa Cruz Biotech clone 9E10), mouse monoclonal antibody to the N-terminus of IFI16 (Santa Cruz Biotech clone 1G7), mouse monoclonal antibody to the C-terminus of IFI16 (Abcam clone ab104409), rabbit polyclonal antibody to the C-terminus of AIM2 (Cell Signaling Technology clone 8055), rabbit polyclonal antibodies to IκBα (clone 44D4)/p-IκBα (clone 14D4), JNK (clone 9252)/p-JNK (9251), p38 (clone 9212)/p-p38 (clone 12F8), p42/44 (clone 9102)/p-p42/44 (9101), IRF3 (clone D83B9), p-IRF3 (clone 4D4G) (all Cell Signaling Technology) and mouse monoclonal antibody to β-tubulin (Santa Cruz Biotech clone TU-02), mouse monoclonal antibody to GST (Santa Cruz Biotech clone B-14) and mouse monoclonal antibody to NLRP3 (Adipogen clone Cryo-2) were used for immunoblot. For co-immunoprecipitations (IP), HEK293 cells were transfected with GFP-POP3, HA-ASC, RFP-AIM2 or empty plasmid in 100 mm dishes (Lipofectamine 2000, Invitrogen). Cells were lysed (50 mM Hepes pH 7.4, 150 mM NaCl, 10% Glycerol, 2 mM EDTA, 0.5% Triton X-100, supplemented with protease inhibitors) 36 hrs post transfection. Cleared lysates were subjected to IP by incubating with immobilized antibodies as indicated for 16 hrs at 4° C., followed by extensive washing with lysis buffer. Bound proteins were separated by SDS-PAGE, transferred to PVDF membranes and analyzed by immunoblotting with indicated antibodies and HRP-conjugated secondary antibodies, ECL detection (Pierce), and image acquisition (Ultralum). TCL (5%) were also analyzed where indicated.

Endogenous NLRP3 and AIM2 inflammasome complexes were similarly purified from ultrapure LPS-primed (16 hrs, 100 ng/mL) THP-1 cells following nigericin treatment (45 min, 5 µM) or MVA-infection (90 min), respectively. For GST pull down experiments, POP3 was cloned into pGEX-4T1 and affinity purified as a GST fusion protein from *E. coli* BL21. Proteins were either prepared by in vitro transcription/translation (TNT Quick Coupled Transcription/Translation, Promega), or TCL were prepared from IFN-β-treated (16 hrs) BMDM or THP-1 cells by lysis (50 mM Hepes pH 7.4, 120 mM NaCl, 10% Glycerol, 2 mM EDTA, 0.5% Triton X-100, supplemented with protease inhibitors) as a source of endogenous proteins, and cleared lysates were incubated with immobilized GST-POP3 or GST control for 16 hrs at 4° C., followed by extensive washing with lysis buffer and analysis as above. For ASC cross-linking, $4 \times 10^6$ BMDM were seeded in 60 mm plates and subjected to cross-linking as described55. Briefly, cells were transfected with 1 µg/ml poly (dA:dT) for 5 hrs, supernatants were removed, cells rinsed with ice-cold PBS and lysed (20 mM Hepes pH 7.4, 100 mM NaCl, 1% NP-40, 1 mM sodium orthovanadate, supplemented with protease inhibitors) and further lysed by shearing. Cleared lysates were stored for immunoblot analysis and the insoluble pellets were resuspended in 500 µl PBS, supplemented with 2 mM disuccinimydyl suberate (DSS, Pierce) and incubated with rotation at room temperature for 30 min. Samples were centrifuged at 5,000 rpm for 10 min at 4° C. and the cross-linked pellets were resuspended in 50 µl Laemmli sample buffer and analyzed by immunoblot. Human lung tissue was embedded in paraffin, cut into 3 µm sections, mounted, deparaffinized and immunostained with mouse monoclonal CD68 (Dako)

and rabbit polyclonal POP3 and peroxidase (HRP)/DAB+ and alkaline phosphatase (AP)/Fast Red enzyme/chromogen combinations (Dako) and specific isotype controls (Dako) and haemotoxylin counterstaining of nuclei.

Immunofluorescence Microscopy hMΦ were grown on cover slips and either IFN-β treated for 16 hrs or infected with GFP, GFP-POP3 expressing adenovirus, MVA for 2 hrs or KSHV for 8 hrs, fixed, permeabilized, and immunostained with AIM2 (Cell Signaling clone 8055), IFI16 (Santa Cruz Biotech clone 1G7) and POP3 (custom raised) antibodies and secondary Alexa Fluor 546-conjugated antibodies and DAPI (Invitrogen) (Bryan et al. J Immunol. 2009; 182:3173-82; herein incorporated by reference in its entirety). Images were acquired by fluorescence microscopy on a Nikon TE2000E2-PFS with a 100× oil objective and image deconvolution (Nikon Elements).

Cytokine and Caspase-1 Measurement

IL-1β, IL-18, TNFα, IL-6, IFN-β and IFN-γ secretion was quantified from clarified culture SN obtained from hMΦ, BMDMs, PM and from mouse serum by ELISA (BD Biosciences, eBiosciences, Invitrogen). Samples were analyzed in triplicates and repeated at least three times, showing a representative result. Active caspase-1 p10 was detected by immunoblot in TCA-precipitated serum-free culture supernatants 4 hrs after treatment (Khare S, et al. Immunity. 2012; 36:464-76; herein incorporated by reference in its entirety).

mRNA Analysis mRNA expression of target genes was quantified by RT-PCR or in vivo by using gold nanoparticles conjugated to specific oligonucleotides duplexed with Cy5-labeled reporter strands, which are non-toxic and are endocytosed by live cells (SmartFlares; Millipore). Subsequent analysis was performed by flow cytometry in combination with linage specific markers. 7-12 weeks old mice received an i.p. injection of MCMV (105 PFU) for 6 hrs. Mice were euthanized and peritoneal cells were obtained by lavage. Blood was obtained by retro-orbital bleeding, collected in EDTA-containing tubes, and incubated for 16 hrs with control or POP3 specific SmartFlares (1:1000 dilution in HBSS). Subsequently, cells were blocked with Fc-Block (2.4G2, BD), stained with fluorochrome-conjugated antibodies (see below), fixed and depleted of red blood cells using BD FACS Lysing solution (BD Biosciences) and analyzed on a BD LSR II flow cytometer. Data were compensated and evaluated using FlowJo software (Tree Star, Ashland, Oreg., USA). Doublets and debris were excluded and leukocytes were identified using the pan-hematopoietic marker CD45 (30-F11, BD). Leukocyte subsets were identified as following: CD4 T cells as CD4+ (RM4-5, BD), CD8 T cells as CD8+ (53-6.7, BD), B cells as B220+ (RA3-6B2, BD), NK cells as NK1.1+ (PK-136, BD), neutrophils as CD11b+ (M1/70, eBioscience) and Ly6G+ (1A8, BD), monocytes as CD11b+ (M1/70, eBioscience) and Ly-6C+ (AL-21, BD) and macrophages as CD11b+ (M1/70, eBioscience) and F4/80+ (BM8, eBioscience). Monocytes were further subdivided into Ly-6Chi classical or inflammatory and Ly-6Clo/med non-classical or resident monocytes. Total RNA was isolated from hMΦ, BMDM or mouse blood using Trizol (Invitrogen) or the mouse RiboPure-blood RNA isolation kit (Invitrogen), treated with DNase I, reverse transcribed with GoScript (Promega) and analyzed by TaqMan Real-time gene expression system using predesigned FAM labeled primer/probes on an ABI 7300 Real time PCR machine (Applied Biosystems) and displayed as relative expression compared to GAPDH or β-actin. The POP3 TaqMan assay was custom designed: POP3-Fwd: 5'-AGCACGAGTAGCCAACTTGATT-3' (SEQ ID NO: 3), POP3-Rev: 5'-GGTCTTCCTCACTGCAGACA-3' (SEQ ID NO: 4) and POP3-FAM probe: 5'-CCATGCCAGCGTTTTA-3' (SEQ ID NO: 5). The RT-PCR primers for POP3 were: POP3-Fwd: 5'-ATGGAGAGTAAATATAAGGAG-3' (SEQ ID NO: 6), POP3-Rev: 5'-TCAACATGCATTCCCAGAAAT-3' (SEQ ID NO: 7).

In Vivo Virus Infection and Intracellular IFN-γ Staining 8-10 week-old age and gender matched wild type (WT) and CD68-POP3 mice were randomly infected with 1×105 to 1×106 PFU by i.p. injection of MCMV or mock salivary gland homogenates and euthanized after 36 hrs. Spleens were digested with collagenase type D (Roche) (1 mg/mL) and DNase I (Roche) (0.1 mg/mL) in HBSS at 37° C. for 15 min, passed through 40 μm nylon cell strainers (BD Biosciences), after which red cells were lysed using 1× BD Pharm Lyse buffer (BD Biosciences), and washed with complete RPMI medium (RPMI 1640 with 10% FCS, 2 mM glutamine, 100 U penicillin/0.1 mg streptomycin/mL, 10 mM HEPES buffer, and 1 mM sodium pyruvate). Splenocytes were counted (Countess cell counter; Invitrogen) and 3×106 splenocytes were directly stained for IFN-γ expression, and an additional 3×106 splenocytes were first suspended in complete RPMI medium and stimulated for 4 hrs in the presence of leukocyte activation cocktail (2 μL/mL, BD Biosciences) before staining (Rathinam V A, et al. Nat Immunol. 2010; 11:395-402; herein incorporated by reference in its entirety). Splenocytes were pre-incubated with mouse Fc block, and labeled with pre-titrated fluorescent antibodies to B220, CD4, CD8, CD11b, CD69, NK1.1, as described above and Ly49H (3D10, eBioscience). Intracellular staining for IFN-γ (XMG1.2, eBioscience) was accomplished using a BD Cytofix/Cytoperm Kit according to the manufacturer's specifications (BD Biosciences) and dead cells were excluded using Aqua live/dead staining (Invitrogen). At least 400,000 events per sample were acquired on a BD LSRII instrument and data were analyzed with FlowJo software (TreeStar, Inc).

MSU-Induced Peritonitis 10-12 week-old age and gender matched WT and CD68-POP3 mice were randomly i.p. injected with either PBS (0.5 mL/mouse) or MSU crystals in PBS (10 mg in 0.5 mL PBS/mouse). 5 hrs after MSU injection, mice were i.p. administered the luminescent Xenolight Rediject Inflammation probe (200 mg/kg, PerkinElmer) (Gross S, et al. Nat Med. 2009; 15:455-61; herein incorporated by reference in its entirety). Images were exposed for 5 min (IVIS Spectrum, PerkinElmer) and luminescence quantified with Living Image (PerkinElmer). Mice were also euthanized 7 hrs after MSU injection and peritoneal cavities were flushed with 2 mL of ice-cold PBS/10% FBS, clarified by centrifugation, and analyzed for IL-1β by ELISA.

POP3 is Expressed in Response to Type-I Interferons

Figure 1C:
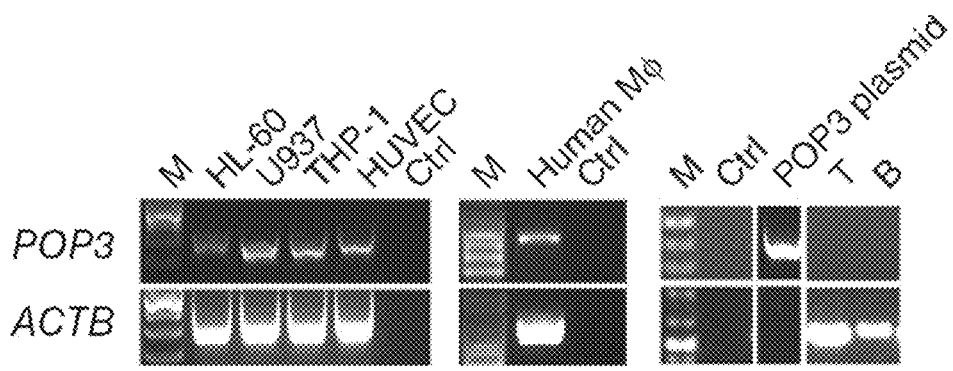
Figure 1E:
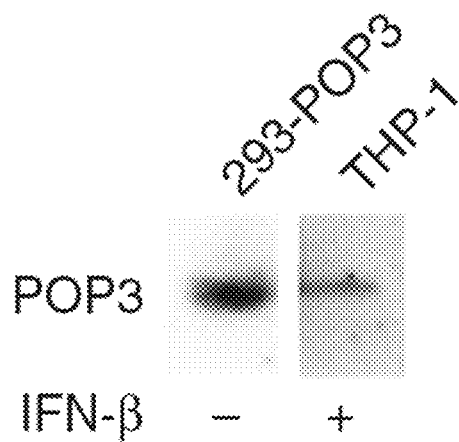
Figure 1B:
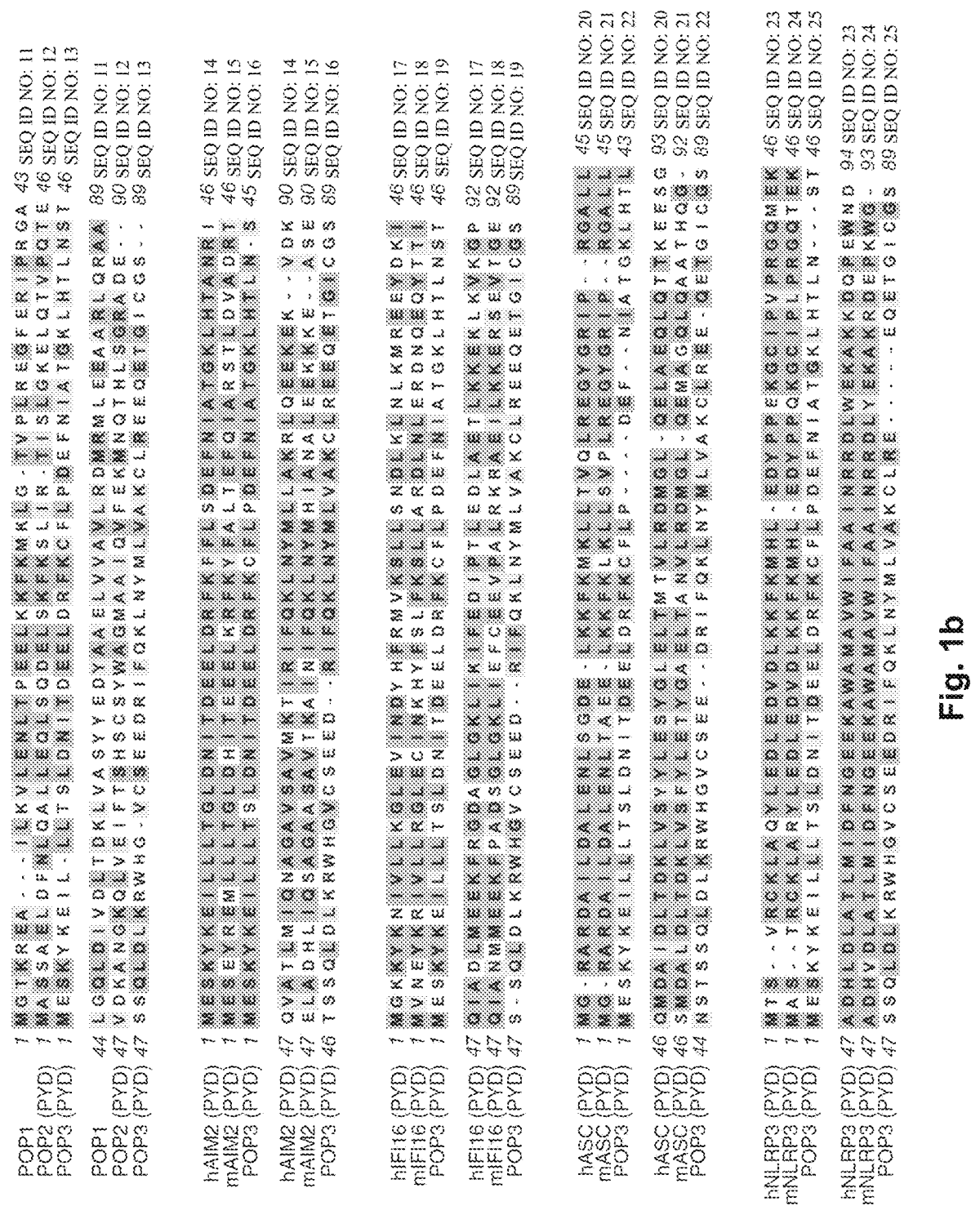
Figure 1D:
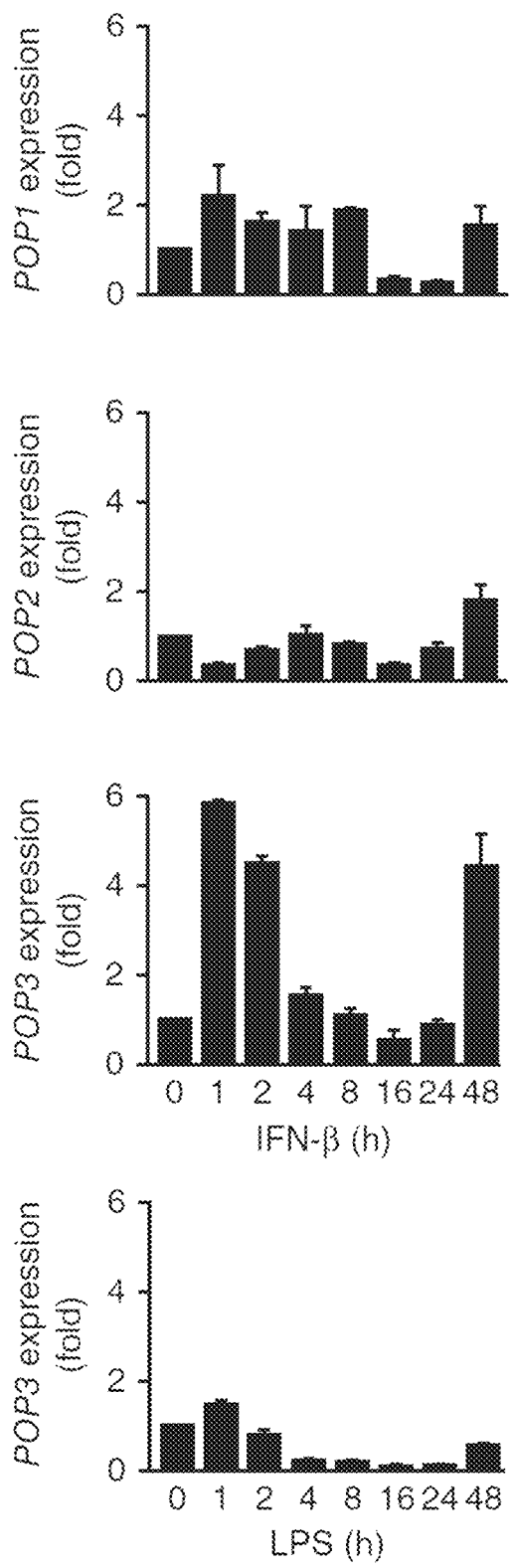
Figure 1F:
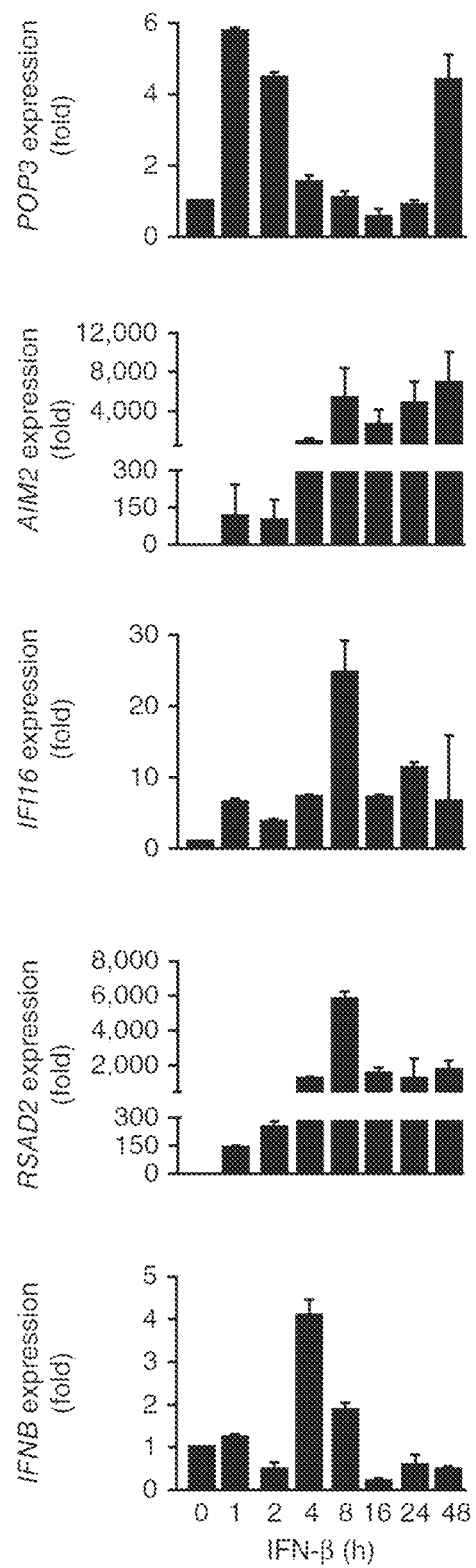
Figure 2B:
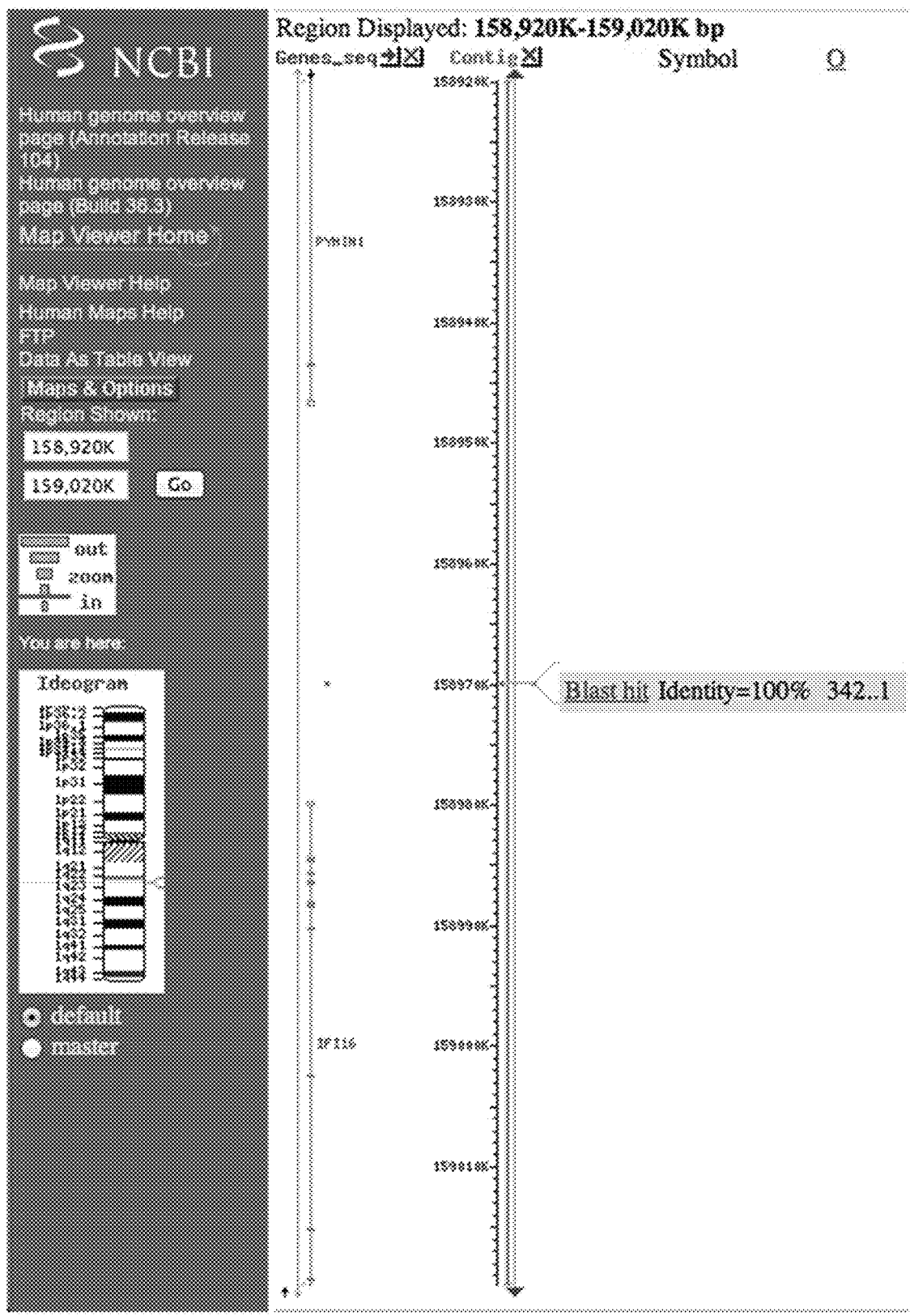
Figure 3C:
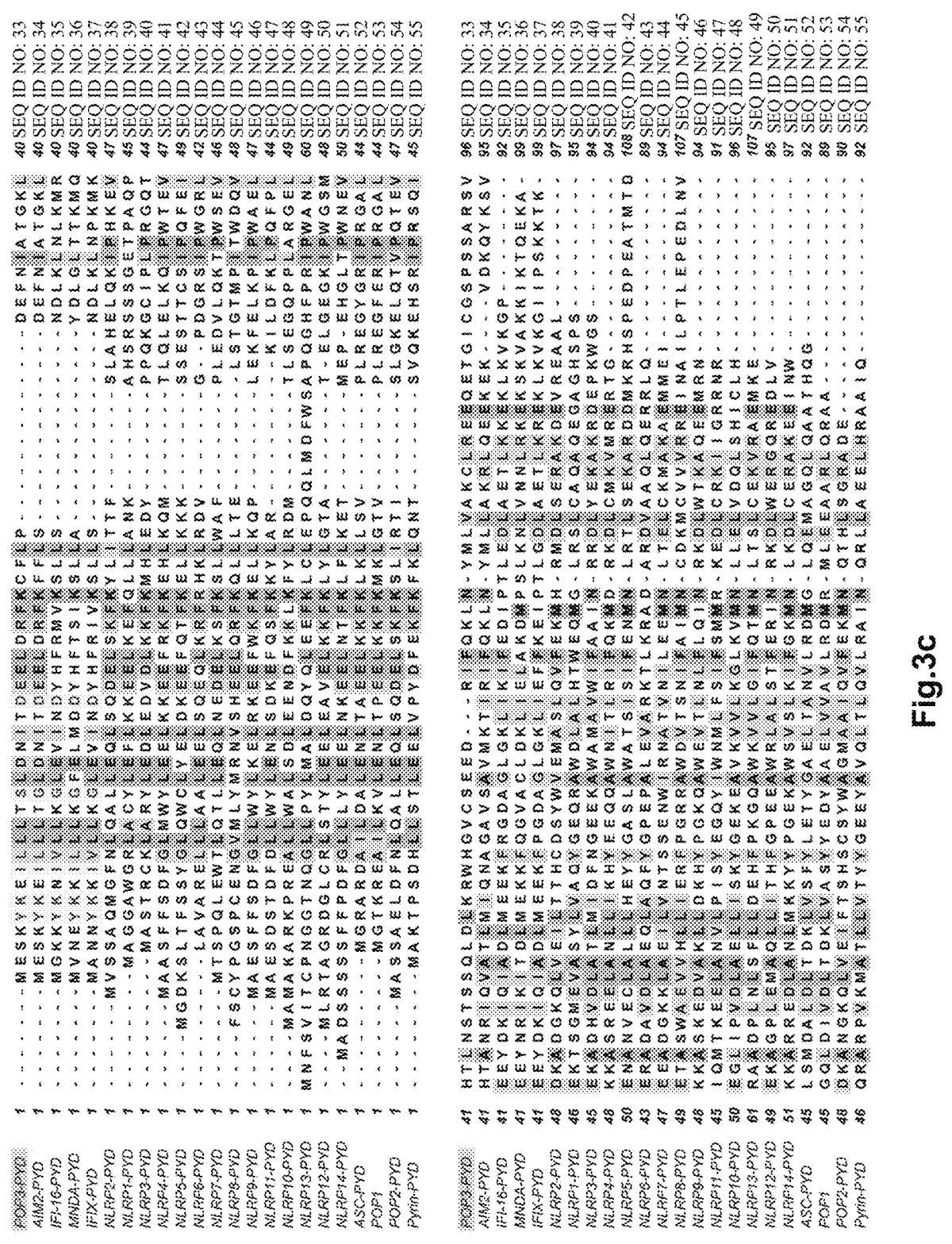
Figure 3D:
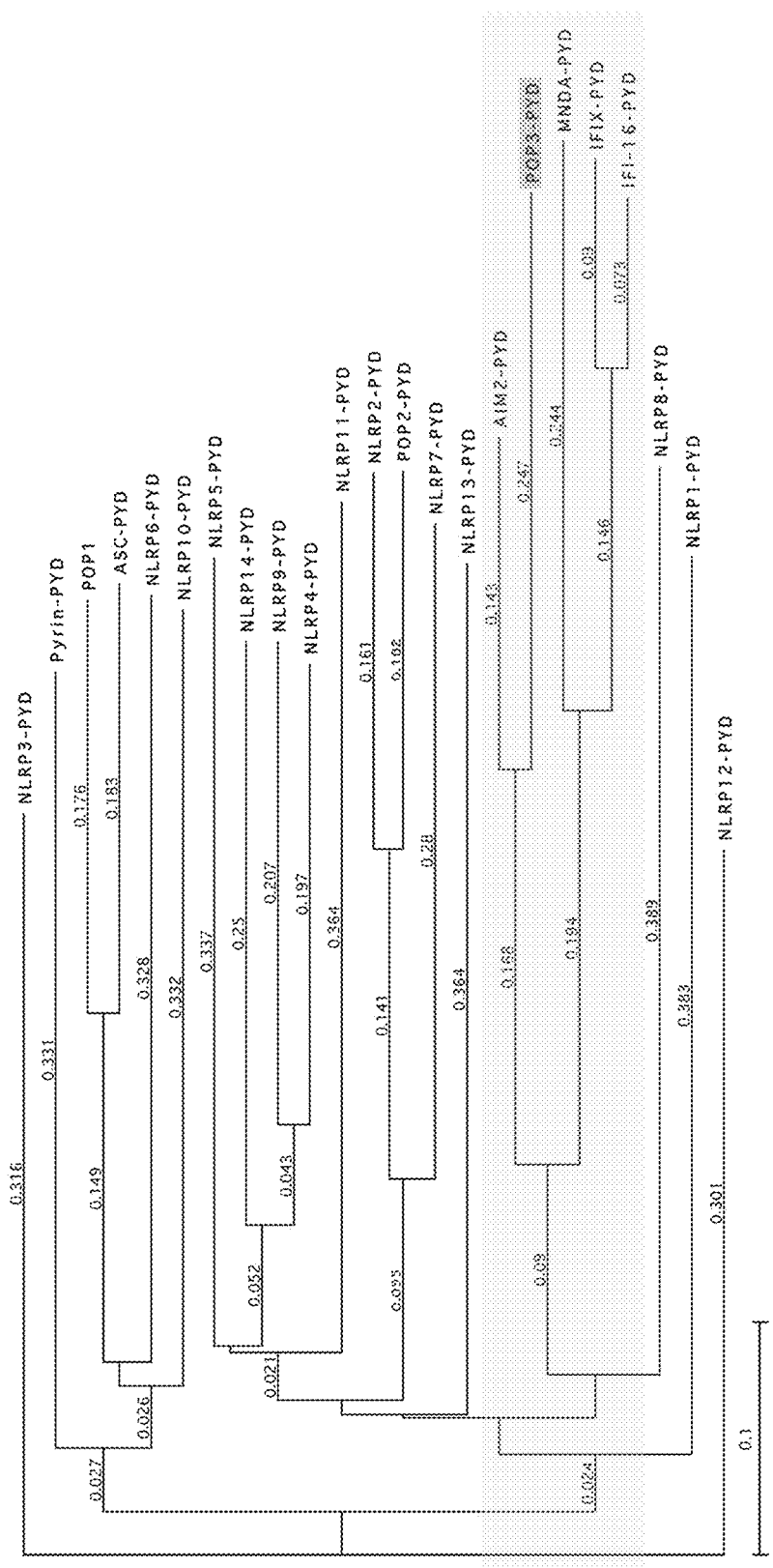
Figure 4C:
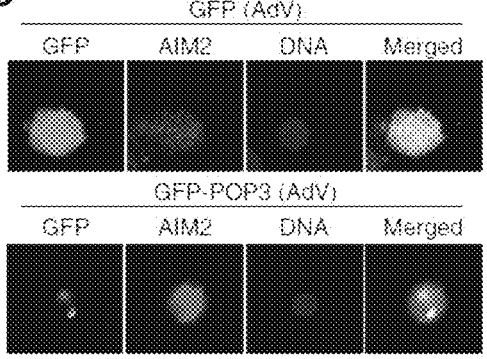
Figure 4D:
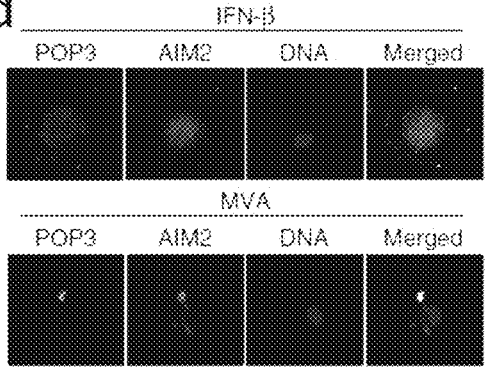
Figure 4E:
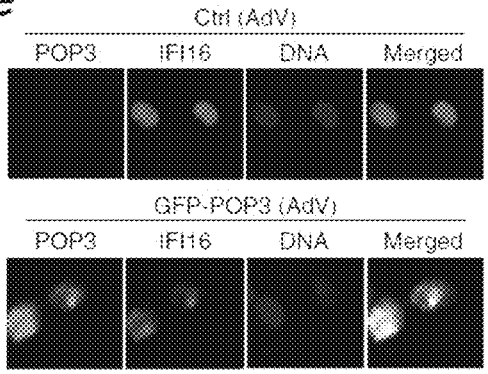
Figure 4F:
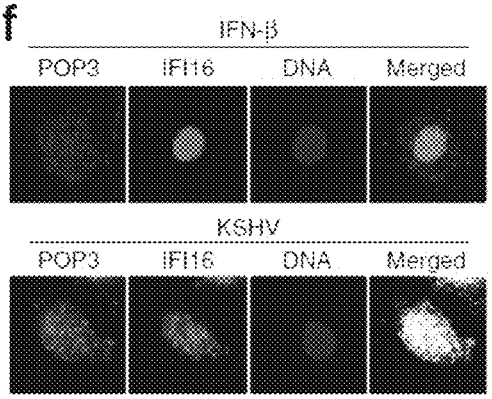

A previously undescribed human POP family member, POP3, was identified (Genbank accession number: KF562078) (FIG. 1a). The POP3 cDNA revealed an open reading frame of 342 bp (FIG. 2a) encoded from a single exon located within the IFN-inducible gene cluster between IFI16 and pyrin and HIN domain family member 1 (PYHIN1) on chromosome 1q23, which also contains AIM2 and myeloid cell nuclear differentiation antigen (MNDA) (FIG. 2b). In comparison, the syntenic mouse chromosomal region 1H3 is amplified and contains 13 predicted genes, but not a POP3 ortholog (Schattgen & Fitzgerald. Immunol Rev. 2011; 243:109-18; Ludlow et al. Exp Cell Res. 2005; 308:1-17; herein incorporated by reference in their entireties). POP3 encodes a single PYD of 113 aa with 5 α-helices, whereas the PYD of AIM2 consists of 6 α-helices. Hence, the 3rd AIM2-PYD α-helix appears to be unstructured in POP3 (FIG. 3a), reminiscent to the structure observed for the PYD of NLRP1, which forms a flexible loop instead of α-helix 3 and is predicted to become stabilized upon PYD-PYD interaction23. All 3 POPs exhibited low sequence homology to each other, indicating that they have unique functions (FIG. 1b). In contrast to POP1 and POP2, POP3 showed high sequence similarity to the PYD of AIM2 (FIG. 1b, Table 1), and showed overall high similarity to the PYDs of HIN-200 family members (FIG. 3b) (Jin et al. J Biol Chem. 2013; 288:13225-35; herein incorporated by reference in its entirety). POP3 shared several of the characteristic sequence motifs within α-helices 1 and 2 of HIN-200 PYDs, but not those present within α-helices 5 and 6 (FIG. 3c). Phylogenetic tree analysis of all PYD proteins also placed POP3 within the HIN-200 family (FIG. 3d). Thus, POP3 most likely originated from exon duplication of the AIM2-PYD, reminiscent to POP1, which is derived from the PYD of ASC (Stehlik C, Krajewska M, Welsh K, Krajewski S, Godzik A, Reed J C. The PAAD/PYRIN-only protein POP1/ASC2 is a modulator of ASC-mediated NF-κB and pro-Caspase-1 regulation. Biochem J. 2003; 373:101-113; herein incorporated by reference in its entirety). Consistently, POP3 revealed low sequence homology with the PYDs of mouse and human ASC and NLRP3 (FIG. 1b, Table 1). POP3 mRNA was expressed in monocytic cell lines and human primary macrophages (hMΦ), but not in B and T cells (FIG. 1c). Similar to ALRs, POP3 expression was upregulated in response to IFN-β in hMΦ, but the TLR4 agonist LPS did not induce POP3 expression (FIG. 1d). Accordingly, POP3 was also detected by immunoblot in IFN-β-treated THP-1 macrophages (FIG. 1e). The POP3 expression pattern was unique, since neither POP1 nor POP2 were regulated by IFNβ, emphasizing a selective role of POP3 within the type I-IFN-mediated host response. POP3 expression was upregulated as an early response gene within the first two hours, as well as a late response gene after 48 hours of IFN-β treatment, which was distinctive from AIM2, IFI16, IFNB and the IFN-stimulated gene RSAD2 (also known as VIPERIN) (FIG. 10. Thus, the IFN-β-inducible POP3 is a member of the POP family and shows similarity to the PYDs of HIN-200 proteins.

with ASC, albeit at different sites and in response to different stimuli (Ludlow et al. Exp Cell Res. 2005; 308:1-17; Fernandes-Alnemri et al. Nature. 2009; 458:509-13; Kerur N, et al. Cell Host Microbe. 2011; 9:363-75; herein incorporated by reference in their entireties). While DNA from Modified Vaccinia virus Ankara (MVA) and murine cytomegalovirus (MCMV) is sensed by AIM2 in the cytosol11-14, modified DNA originating from latent Kaposi's Sarcoma-Associated Herpesvirus (KSHV) infection is recognized by IFI16 within the nucleus in vitro (Kerur N, et al. Cell Host Microbe. 2011; 9:363-75; herein incorporated by reference in its entirety). AIM2 was predominantly localized to cytosolic punctate structures, and this pattern was not altered in response to GFP adenovirus (AdV) infection (FIG. 4c), while adenovirus-mediated GFP-POP3 expression resulted in co-localization in cytoplasmic punctate structures (FIG. 4c). We also observed very limited co-localization of endogenous AIM2 with endogenous POP3 in a few cytosolic punctate structures in hMΦ treated with IFN-β to up-regulate AIM2 and POP3 expression (FIG. 4d), but co-localization was greatly enhanced 2 hours after MVA infection (FIG. 4d). In contrast to the predominantly cytosolic AIM2 localization, IFI16 localizes within the nucleus in endothelial cells, where it interacts with ASC. Similarly, solely nuclear IFI16 localization we observed in hMΦ, which was not altered in response to control adenovirus infection (FIG. 4e). However, in response to adenovirus-mediated expression of GFP-POP3, IFI16 was re-distributed to the cytosol, where it partially co-localized with GFP-POP3 (FIG. 4e). In agreement, co-localization of endogenous IFI16 and POP3 was not observed in IFN-β-treated hMΦ (FIG. 4f), nor did MVA infection alter IFI16 distribution or promote co-localization with POP3 at the tested times. Yet, KSHV infection caused partial cytosolic redistribution of IFI16 as quickly as 2 hours p.i. (data not shown), which was more prominent 8 hours p.i. At that time we observed partial co-localization of IFI16 with POP3 (FIG. 4f), although KSHV did not cause aggregation of IFI16 in hMΦ at the titer used in our experiments. These results further supported an interaction of POP3 with ALRs.

Accordingly, GST-POP3 also purified endogenous AIM2 and IFI16 (FIG. 4g). However, in contrast to POP1 and POP2 (Dorfleutner A, et al. Infect Immun 2007; 75:1484-

TABLE 1

BLOSSUM identity scores.
Identity in % is shown for POP3 and the proteins aligned in FIG. 1b.

|  | hAIM2 | mAIM2 | hIFI16 | mIFI16 | hASC | mASC | hNLRP3 | mNLRP3 | POP1 | POP2 |
|---|---|---|---|---|---|---|---|---|---|---|
| POP3 identity (%) | 60.9 | 43.5 | 17.4 | 15.2 | 18.9 | 16.8 | 20.2 | 12.5 | 21.7 | 11.1 |

Since PYDs usually exhibit homotypic interactions and POP3 contained several HIN-200 PYD-specific sequence motifs and displayed high homology to the PYD of AIM2, experiments were conducted during development of embodiments described herein to determine if POP3 was able to bind to the PYD of HIN-200 proteins. GST-POP3, but not GST control, bound to the PYD of AIM2 and IFI16. However, GST-POP3 showed no significant interaction with the PYDs of MNDA and PYHIN1 (FIG. 4a). Upon transient co-transfection of POP3 with AIM2 and IFI16 in HEK293 cells, their interaction was confirmed by co-immunoprecipitation (FIG. 4b).

This observation was further supported by co-localization studies. AIM2 and IFI16 have been shown to co-localize 1492; herein incorporated by reference in its entirety), POP3 did not bind to the inflammasome adaptor ASC. Unexpectedly, weak binding of recombinant POP3 to NLRP3 we also observed in vitro (FIG. 4g), in spite of the rather low degree of homology and the presence of the HIN-200 PYD-specific sequence motifs within POP3. Assembly of the inflammasome through PYD-PYD interactions is a key step for its activation and subsequent cytokine release. The PYD of ALRs and NLRP3 interact with the PYD of ASC, and it was contemplated that the PYD-containing POP3 could interfere with this interaction. Contrary to the interaction of recombinant POP3 with NLRP3 in vitro, POP3 was not recruited to and did not disrupt the NLRP3-ASC complex in LPS-primed and nigericin-treated THP-1 cells (FIG. 4h). However, POP3 was recruited to, and disrupted the endogenous AIM2-ASC complex in response to MVA infection in THP-1 cells (FIG. 4i). Moreover, POP3 also caused a reduced interaction of ectopically expressed ASC and AIM2 in HEK293 cells by co-immunoprecipitation, indicating that POP3 is able to disrupt ALR inflammasome complex assembly by competing with ASC for the PYD binding site in AIM2 (FIG. 4j). These data indicate that POP3 functions selectively as an ALR inflammasome inhibitor.

AIM2 inflammasome assembly causes the formation of ASC oligomers (Fernandes-Alnemri et al. Nature. 2009; 458:509-13; herein incorporated by reference in its entirety). Only co-transfection of AIM2 and ASC in HEK293 cells caused the formation of ASC dimers and oligomers, but not transfection of ASC and POP3 or POP3, ASC or AIM2 alone. However, in the presence of POP3, AIM2-mediated ASC dimers and oligomers were significantly reduced (FIG. 4k), indicating that POP3 can inhibit the PYD-dependent recruitment of ASC to AIM2. These data indicate that POP3 is a previously undescribed IFN-β-inducible protein, which directly interacts with the ALRs AIM2 and IFI16 through PYD-PYD interaction to prevent inflammasome formation.

POP3 Inhibits ALR-Mediated IL-1β and IL-18 Release

Figure 5A:
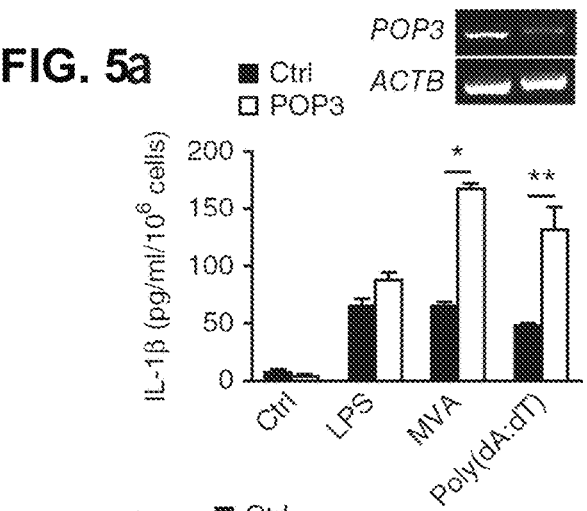
Figure 5B:
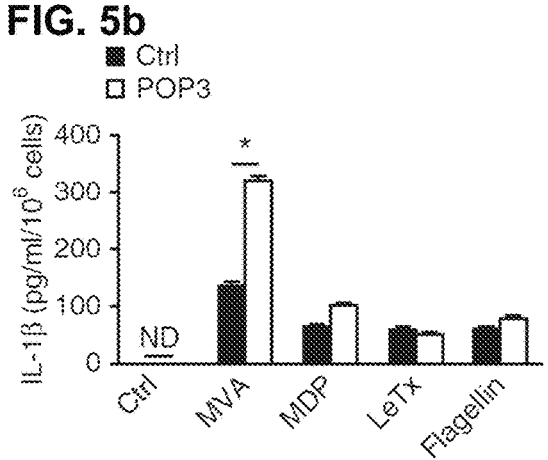
Figure 5F:
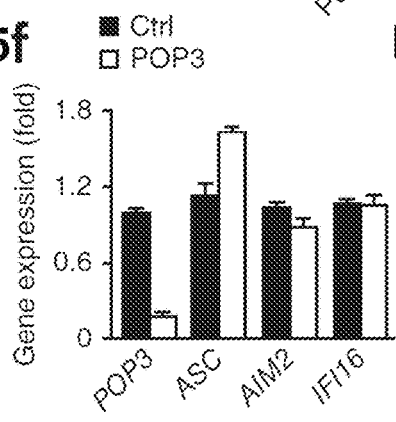
Figure 5G:
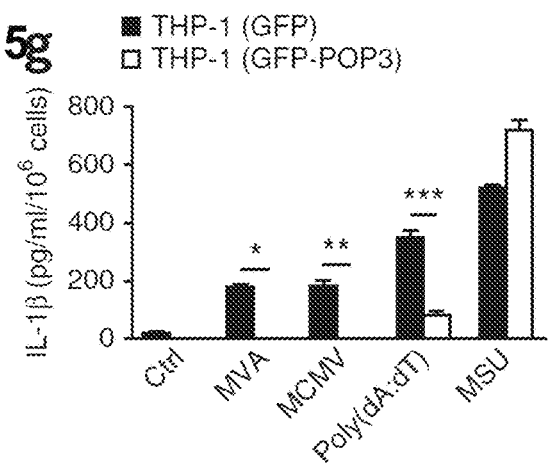
Figure 6A:
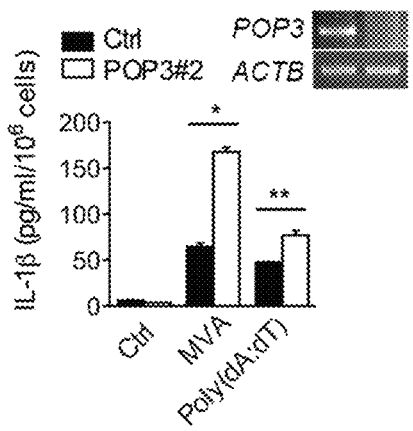
FIGS. 6a-i. Silencing of POP3 specifically affects the AIM2 inflammasome.
Figure 6B:
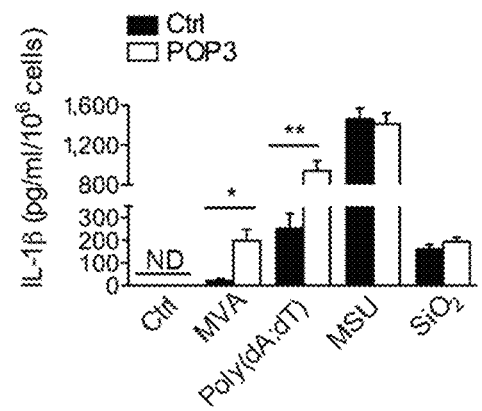
Figure 6E:
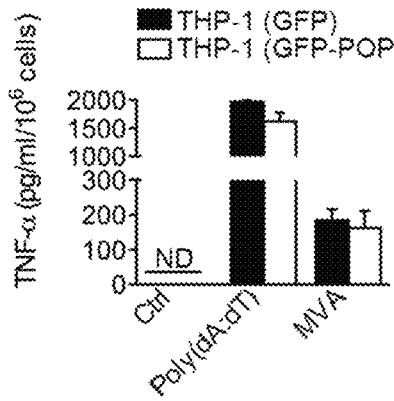
Figure 6F:
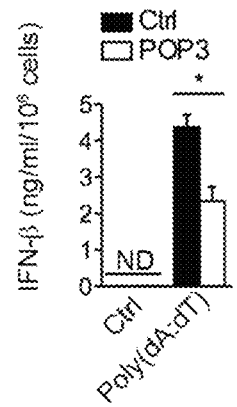
Figure 6H:
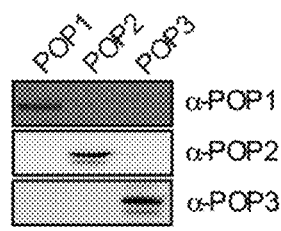
Figure 6I:
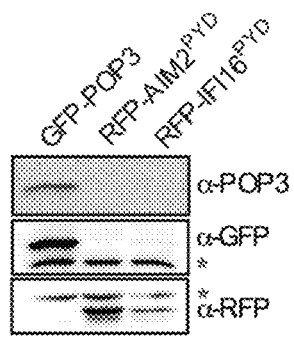
Figure 6C:
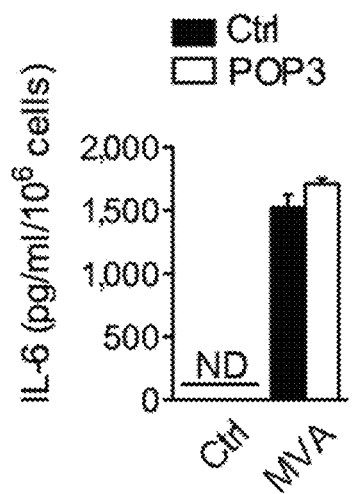
Figure 6D:
Figure 6G:
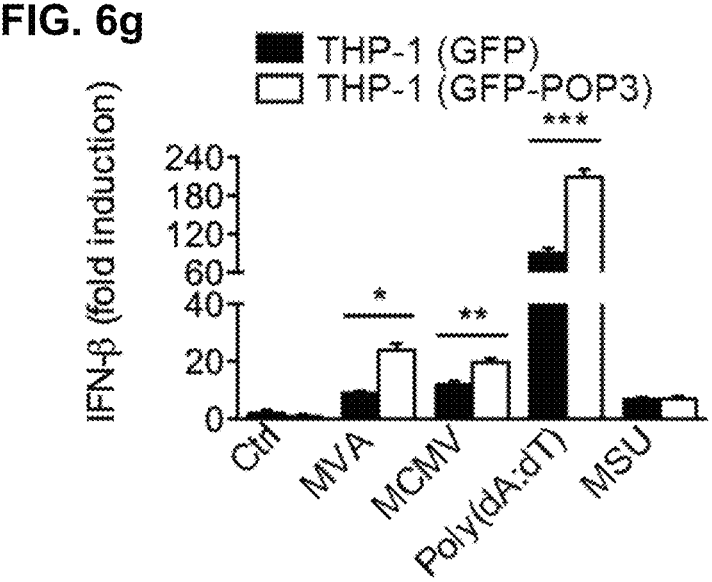

In response to DNA virus infection, AIM2 and IFI16 function as cytosolic and nuclear inflammasome-activating DNA-sensors, respectively (Fernandes-Alnemri T, et al. Nat Immunol. 2010; 11:385-393; Rathinam V A, et al. Nat Immunol. 2010; 11:395-402; Jones J W, et al. Proc Natl Acad Sci USA. 2010; 107:9771-6; Kerur N, et al. Cell Host Microbe. 2011; 9:363-75; herein incorporated by reference in their entireties). In the absence of POP3, following siRNA-mediated silencing in as determined by RT-PCR (FIG. 5a), IL-1β release in response to cytosolic double strand (ds) DNA, such as transfection of poly(dA:dT) or infection with MVA, was significantly enhanced (FIG. 5a). Comparable results were also obtained with a second POP3-targeting siRNA (FIG. 6a). However, POP3 silencing did not affect IL-1β release triggered upon activation of non-ALR inflammasomes, including inflammasome responses to LPS, the NLRP1 inflammasome in response to B. anthracis lethal toxin (LeTx) (Boyden et al. Nat Genet. 2006; 38:240-4; herein incorporated by reference in its entirety) and muramyldipeptide (MDP) (Faustin B, et al. Mol Cell. 2007; 25:713-24; herein incorporated by reference in its entirety), the NLRP3 inflammasome in response to monosodium urate (MSU) crystals (Martinon et al. Nature. 2006; 440:237-241; herein incorporated by reference in its entirety) or silica (SiO2) (Cassel S L, et al. Proc Natl Acad Sci USA. 2008; 105:9035-40; Dostert et al. Science. 2008; 320:674-677; Hornung V, et al. Nat Immunol. 2008; 9:847-56; herein incorporated by reference in their entireties) and the NLRC4 inflammasome in response to S. typhimurium flagellin (Franchi L, et al. Nat Immunol. 2006; 7:576-82; Miao E A, et al. 2006; 7:569-75; herein incorporated by reference in their entireties) (FIG. 5a, b, c). THP-1 cells are widely used to study inflammasome responses and elevated AIM2-dependent release of IL-1β in POP3 silenced THP-1 cells was also observed in response to AIM2-, but not NLRP3-dependent stimuli (6b). Increased MVA-induced IL-18 release upon silencing of POP3 was also observed (FIG. 5d). This effect of POP3 was specific for inflammasome-dependent cytokines, since the release of the inflammasome-independent cytokines TNF (FIG. 5e) and IL-6 (6c) was not affected by POP3 silencing. POP3 silencing also did not affect mRNA expression of ASC, AIM2 and IFI16, as determined by real-time PCR (FIG. 5f) or protein expression (FIG. 6d). Conversely, THP-1 cells stably expressing GFP-POP3, but not GFP control, showed significantly reduced release of IL-1β (FIG. 5g) and IL-18 (FIG. 5h), but not TNF (FIG. 6e), in response to MVA and MCMV infection and transfection of poly(dA:dT), but not in response to MSU crystals, further supporting the observations obtained in hMΦ upon POP3 silencing. Moreover, this cell system also recapitulated the IFN-(3-inducible expression of POP3 (FIG. 5i). Next, POP3 expression in POP3 silenced hMΦ was restored by adenoviral delivery of GFP-POP3, as determined by immunoblot (FIG. 5j). While transduction with a GFP-expressing adenovirus into control siRNA transfected cells slightly increased MVA-induced IL-1β secretion, transduction with a GFP-POP3 expressing adenovirus strongly suppressed this response (FIG. 5j). Overall the data suggest that POP3 functions as an inhibitor of DNA-induced inflammasome activation, while showing no impact on NLRP1, NLRP3 and NLRC4 inflammasomes. In addition to being defective in inflammasome activation, Aim2−/− macrophages show elevated IFN-β production in response to dsDNA, MVA or bacterial infection through a yet unknown mechanism (Rathinam V A, et al. Nat Immunol. 2010; 11:395-402; Fernandes-Alnemri et al. Nature. 2009; 458:509-13; Hornung et al. Nature. 2009; 458:514-8; herein incorporated by reference in its entirety), and IFI16 functions as a sensor promoting IFN-β production in response to DNA virus infection (Unterholzner L, et al. Nat Immunol. 2010; 11:997-1004; herein incorporated by reference in its entirety). In agreement with the elevated IFN-β secretion in Aim2−/− macrophages, which indicates that it may negatively regulate IFN-β production, it was observed that silencing of POP3 decreases IFN-β production in response to MVA infection of hMΦ (FIG. 5k), and poly(dA:dT) transfection in THP-1 cells (FIG. 6f). Conversely, stable GFP-POP3, but not GFP expressing THP-1 cells displayed elevated IFN-β production in response AIM2-specific stimuli (FIG. 6g). Type I IFNs block IL-la and IL-1β synthesis through an IL-10-STATS-dependent autocrine mechanism 34, while simultaneously upregulating expression of IL-1RA and IL-18BP to compete with IL-1β and IL-18 for receptor binding, respectively 35,36. Elevated I11ra and I118 bp transcripts in POP3 expressing and MVA-infected BMDM was consistently observed (FIG. 5h). Collectively, these results indicate that POP3 functions as an inhibitor of ALR inflammasome-mediated release of IL-1β and IL-18 in human macrophages and promotes a type I IFN response.

Macrophage-Specific POP3-Expressing Transgenic Mice

Figure 7A:
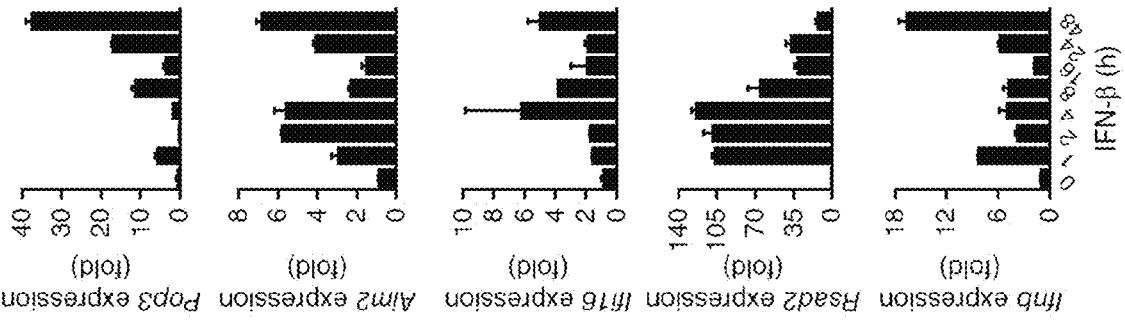
FIGS. 7a-e. Monocyte/macrophage-lineage-specific expression of POP3 in CD68-POP3 TG mice.
Figure 7B:
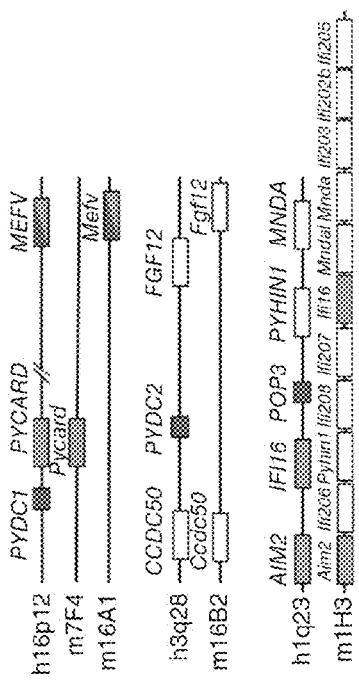
Figure 7C:
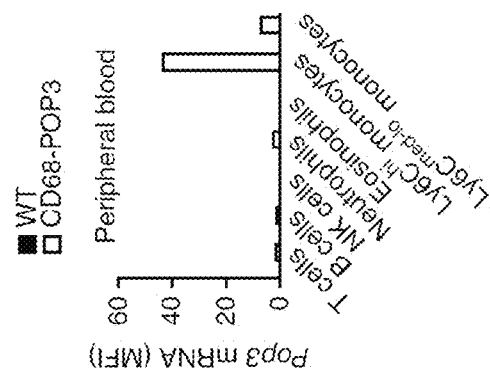
Figure 7D:
Figure 7E:
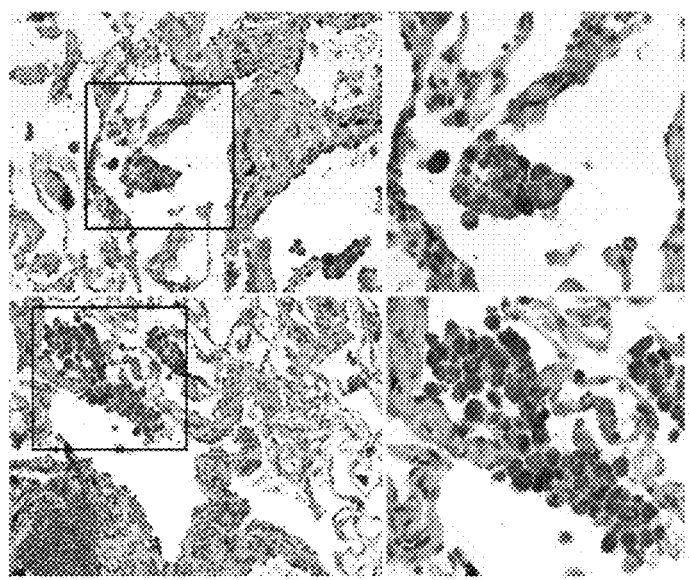
Figure 8A:
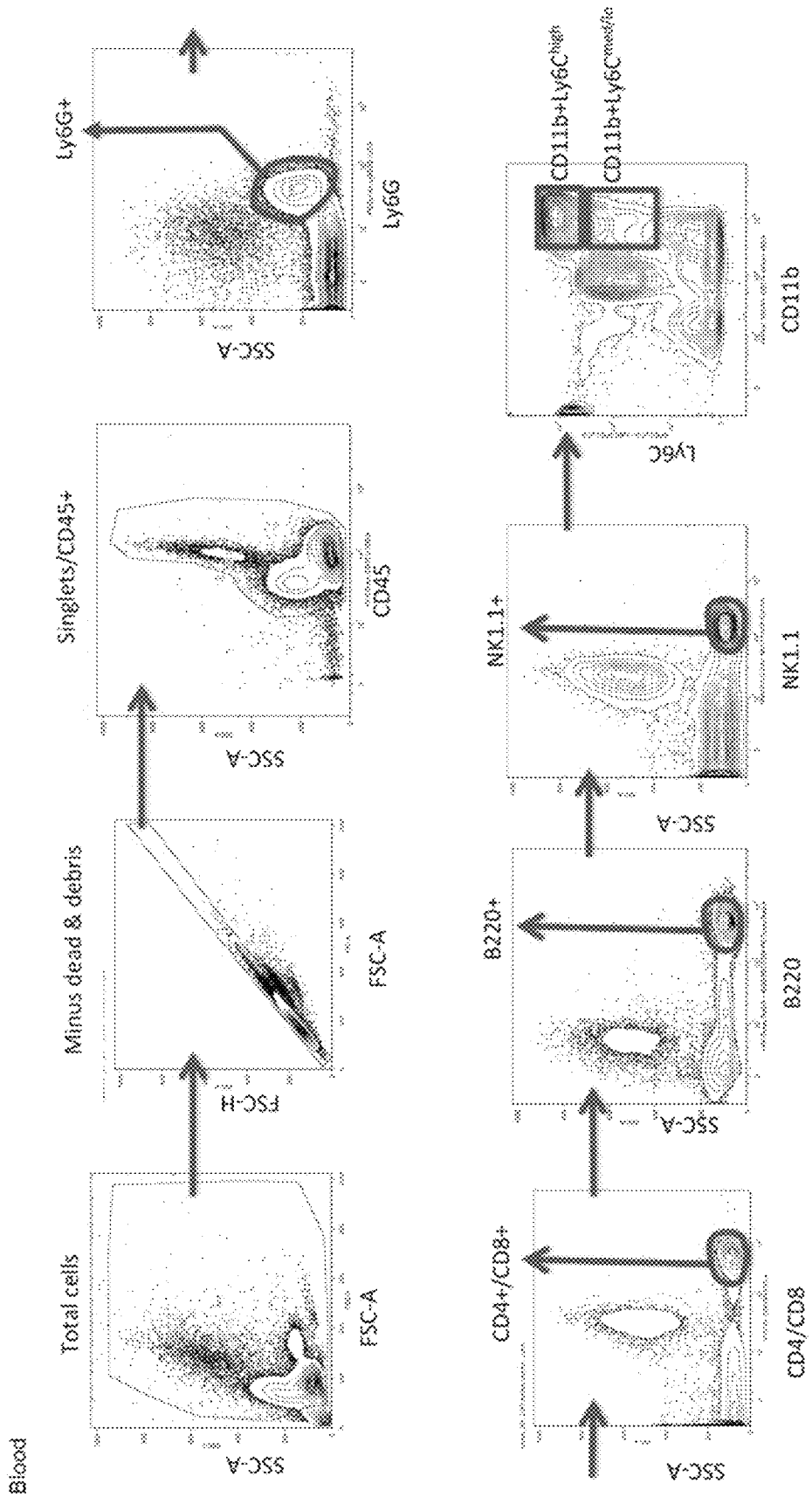
FIGS. 8a-b. A gating strategy used for immunophenotyping of peripheral blood and peritoneal lavage cells. (a) Peripheral blood cells and (b) peritoneal lavage cells obtained 6 h after MCMV infection were gated according to established cell surface markers, as indicated.
Figure 8B:
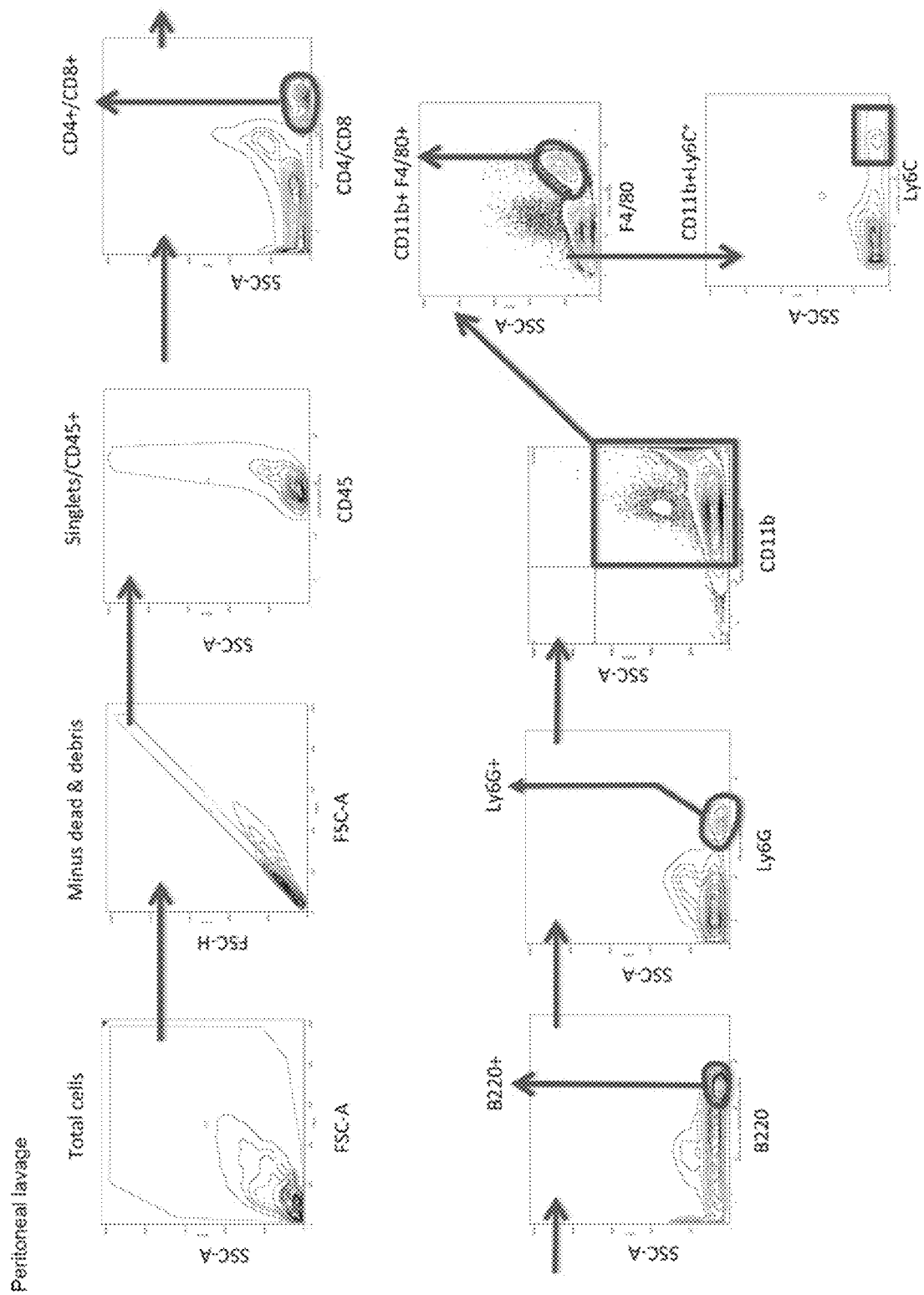

POP1 and POP2 are lacking from mice (Stehlik & Dorfleutner. J Immunol. 2007; 179:7993-8; herein incorporated by reference in its entirety). Similar to the close chromosomal location of POP1 and ASC, POP3 is found next to AIM2 and IFI16, and POP3 is also absent in mice, despite significant amplification of this gene cluster (FIG. 7a). To study the POP3 function in vivo, and in particular its role in inflammasome regulation in macrophages, transgenic (TG) mice were generated expressing POP3 from the human CD68 (hCD68) promoter in combination with the IVS-1 intron containing a macrophage-specific enhancer (Gough et al. Immunology. 2001; 103:351-61; Greaves et al. Genomics. 1998; 54:165-8; herein incorporated by reference in their entireties). Promoter choice was at least partially based on the observation that POP3 was specifically expressed in human CD68+ macrophages in inflamed lung lesions (FIG. 7b), using a custom-raised antibody that did not cross react with other POPs, nor with the related IFI16 and AIM2 PYDs (FIG. 6i, j). Analysis of POP3 mRNA expression in CD68-POP3 TG mice by flow cytometry using SmartFlares, verified expression specifically in the monocyte/macrophage lineage, and particularly in the CD11b+Ly6Chi classical monocytes in peripheral blood and in CD11b+F4/80+ peritoneal macrophages (FIG. 7c, and FIG. 8), thus making the experiments conducted during development of embodiments of the described herein the first macrophage-specific mouse model to study inflammasomes and the first mouse model to study POPs. The low abundance POP3 expression in BMDM generated from CD68-POP3 TG mice was induced by IFN-β as an early and late response gene at the transcriptional level (FIG. 7d), thus closely resembling its regulation observed in hMΦ Aim2, Ifi16 and Rsad2 show higher inducibility in hMΦ than in BMDM, despite the similar Ifnb transcription. Similarly, POP3 protein was inducibly expressed in response to IFN-β or MVA and MCMV infection (FIG. 7e). It was also observed that POP3 protein expression is stabilized in the presence of the proteasome inhibitor MG132 (FIG. 7e), indicating that POP3 expression is not only tightly regulated on the transcriptional-, but also on the post-translational level. Post-translational regulation is further supported by the observation that THP-1 cells expressing GFP-POP3 from the constitutive CMV promoter express elevated levels of POP3 protein after treatment with IFN-β (FIG. 5i). Overall these results support the rationale for using this particular POP3 mouse model.

POP3 Inhibits ALR-Mediated Cytokine Release in BMDM

Figure 9A:
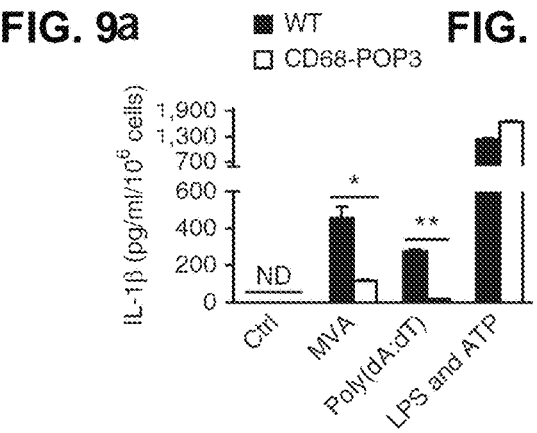
FIGS. 9a-h. POP3 expression in BMDM inhibits AIM2 and IFI16 inflammasome-mediated cytokine release.
Figure 9B:
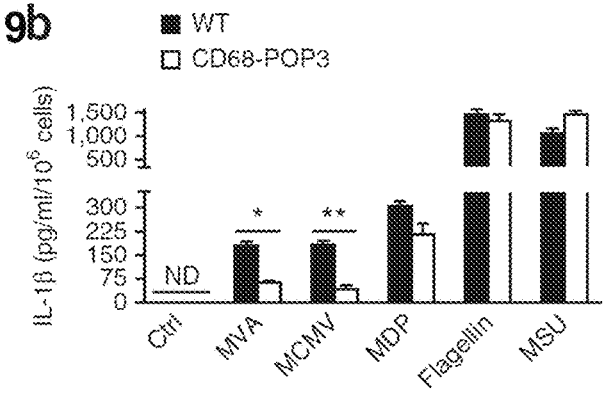
Figure 9C:
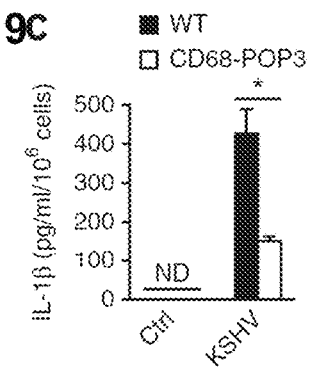
Figure 9D:
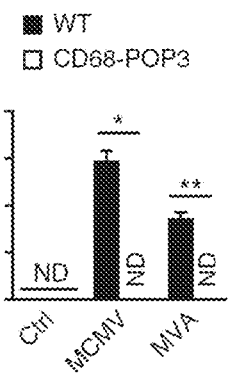
Figure 9E:
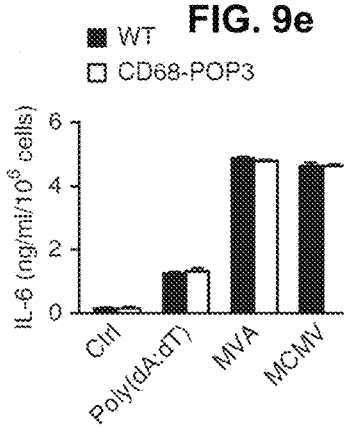
Figure 9F:
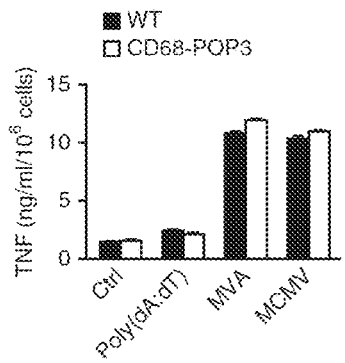
Figure 9G:
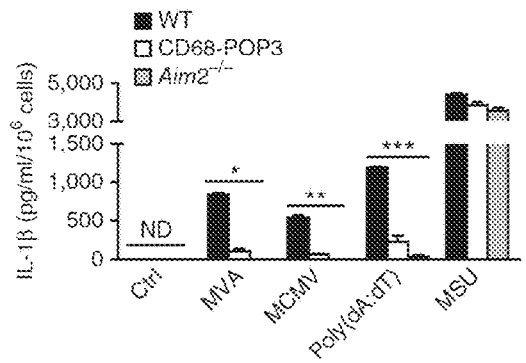
Figure 9H:
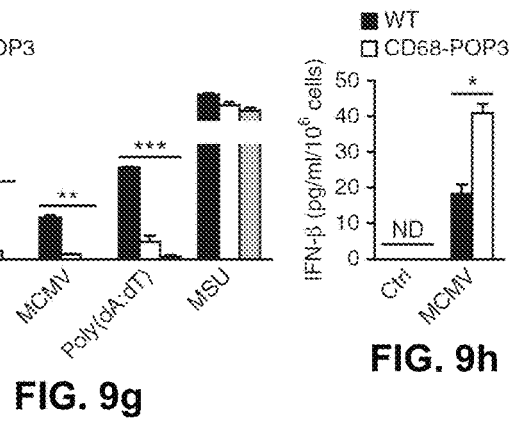

Next, the effect of POP3 expression on AIM2 and other inflammasomes was analyzed. Consistent with the increased inflammasome response observed in the absence of POP3 in POP3 expression resulted in a significant decrease of IL-1β release in response to poly(dA:dT) transfection and MVA or MCMV infections, but not in response to MDP, flagellin, LPS+ATP or monosodium urate crystals (MSU) in BMDM (FIG. 9a, b) and in peritoneal macrophages (FIG. 10a). These results underscore the same selectivity of POP3 for AIM2 inflammasomes in mice and humans without affecting NLRP1b, NLRC4 and NLRP3 inflammasomes (Boyden & Dietrich. Nat Genet. 2006; 38:240-4; Martinon et al. Nature. 2006; 440:p237; Franchi L, et al. Nat Immunol. 2006; 7:576-82; Miao E A, et al. Nat Immunol. 2006; 7:569-75; Mariathasan S, et al. Nature. 2006; 440:228-232; herein incorporated by reference in their entireties). Whereas DNA from MVA and MCMV is sensed by AIM2 in the cytosol, modified DNA originating from latent KSHV infection is recognized by IFI16 within the nucleus in vitro. Based on the observation that POP3 and IFI16 are able to interact, the release of IL-1β in response to KSHV infection was investigated, which was significantly decreased in the presence of POP3, establishing that POP3 impairs AIM2 and likely also IFI16 inflammasomes (FIG. 9c). As for POP3 also inhibited DNA virus-induced IL-18 release (FIG. 9d), but did not alter the release of the caspase-1-independent inflammatory cytokines IL-6 and TNF (FIG. 9e, f). To ensure that random TG POP3 integration was not responsible for the observed phenotype, findings were validated in an independent, second TG line with identical outcomes (FIG. 10b). TG mice were generated ubiquitously expressing the human coxsackie and adenovirus receptor with deleted cytoplasmic domain (hCARΔcyt)40 from the ubiquitin C promoter (FIG. 10c), which allows efficient infection with recombinant adenovirus at low MOI (FIG. 10d). Infection of UbiC-hCARΔcyt BMDM with GFP-POP3 or GFP control expressing adenovirus further confirmed the inhibitory function of POP3 on the AIM2-induced IL-1β release independently of POP3 integration (FIG. 10e). The AIM2-mediated IL-1β release by POP3 was not completely abolished, but nevertheless reached levels close to Aim2–/– macrophages in response to AIM2-dependent stimuli. Neither CD68-POP3 TG-nor Aim2–/– BMDM showed any diminished IL-1β release in response to MSU (FIG. 9g). In agreement with the observation that silencing of POP3 in hMΦ and THP-1 cells partially inhibited IFN-β production (FIG. 9k, FIG. 10f), POP3 expressing BMDM showed elevated levels of IFN-β in response to MCMV infection (FIG. 9h), reminiscent of Aim2–/– macrophages 6. Thus, TG expression of POP3 in mouse macrophages further confirmed a role of POP3 in inhibiting ALR-mediated cytokine release as initially observed by POP3 silencing in and confirmed that human POP3 is functional in mice.

POP3 Inhibits ALR-Mediated Caspase-1 Activation in BMDM

The PYDs of human and mouse ALRs are well conserved. POP3 co-purified IFI16 and AIM2, but not ASC from BMDM (FIG. 11a), similar to what was observed in THP-1 cells (FIG. 4g). As observed in human THP-1 cells, recombinant POP3 also weakly co-purified NLRP3 in BMDM in vitro (FIG. 11a). To delineate the mechanism by which POP3 inhibits ALR inflammasomes in mouse macrophages, ASC oligomerization was analyzed in response to AIM2 inflammasome stimulation with poly(dA:dT) in WT and CD68-POP3 TG BMDM as a readout for AIM2 inflammasome formation (Fernandes-Alnemri et al. Nature. 2009; 458:509-13; herein incorporated by reference in its entirety). Insoluble ASC monomers, dimers and oligomers were drastically decreased in the presence of POP3 (FIG. 11b), supporting impaired AIM2 inflammasome formation in the presence of POP3. Inflammasome formation is essential for caspase-1 activation, and although the protein amount of pro-caspase-1 was not altered in POP3 expressing BMDM, active caspase-1 p10 was significantly reduced in response to MVA and MCMV, but not in response to LPS+ ATP in culture supernatants (FIG. 11c), further emphasizing the functional specificity of POP3 for AIM2, but not NLRP3 inflammasome formation. The POP3 effect was specific for caspase-1 and was not caused by modulating NF-κB activation, since the NF-κB-inducible cytokines TNF and IL-6 were equally secreted (FIG. 9e, f). In addition, similar NF-κB activation and MAPK signaling responses were observed upon MVA infection in the absence and presence of POP3 in BMDM (FIG. 11d). Furthermore, transcription of Il1b, Il18, Ifnb, Asc, Aim2 and Ifi16 was not reduced in POP3 expressing mock and MVA-infected BMDMs (FIG. 11e), further demonstrating a role of POP3 in regulating AIM2-mediated inflammasome activation and caspase maturation, but not in modulating the expression of inflammasome components. Enhanced IFN-β production in POP3 expressing BMDM was supported by the increased and sustained phosphorylation of IRF3 in CD68-POP3 TG BMDM in response to MVA infection (FIG. 11d). POP3 expression was significantly elevated in response to MVA infection (FIG. 11e), similar to its binding partners IFI16 and AIM2, and reminiscent to what was observed by immunoblot in response to MVA infection and IFN-β treatment (FIG. 7d, e). These results demonstrate that POP3 affects cytokine release by inhibiting ALR-mediated caspase-1 activation.

POP3 Blunts ALR-Mediated Anti-Viral Host Defense In Vivo

Figure 13:
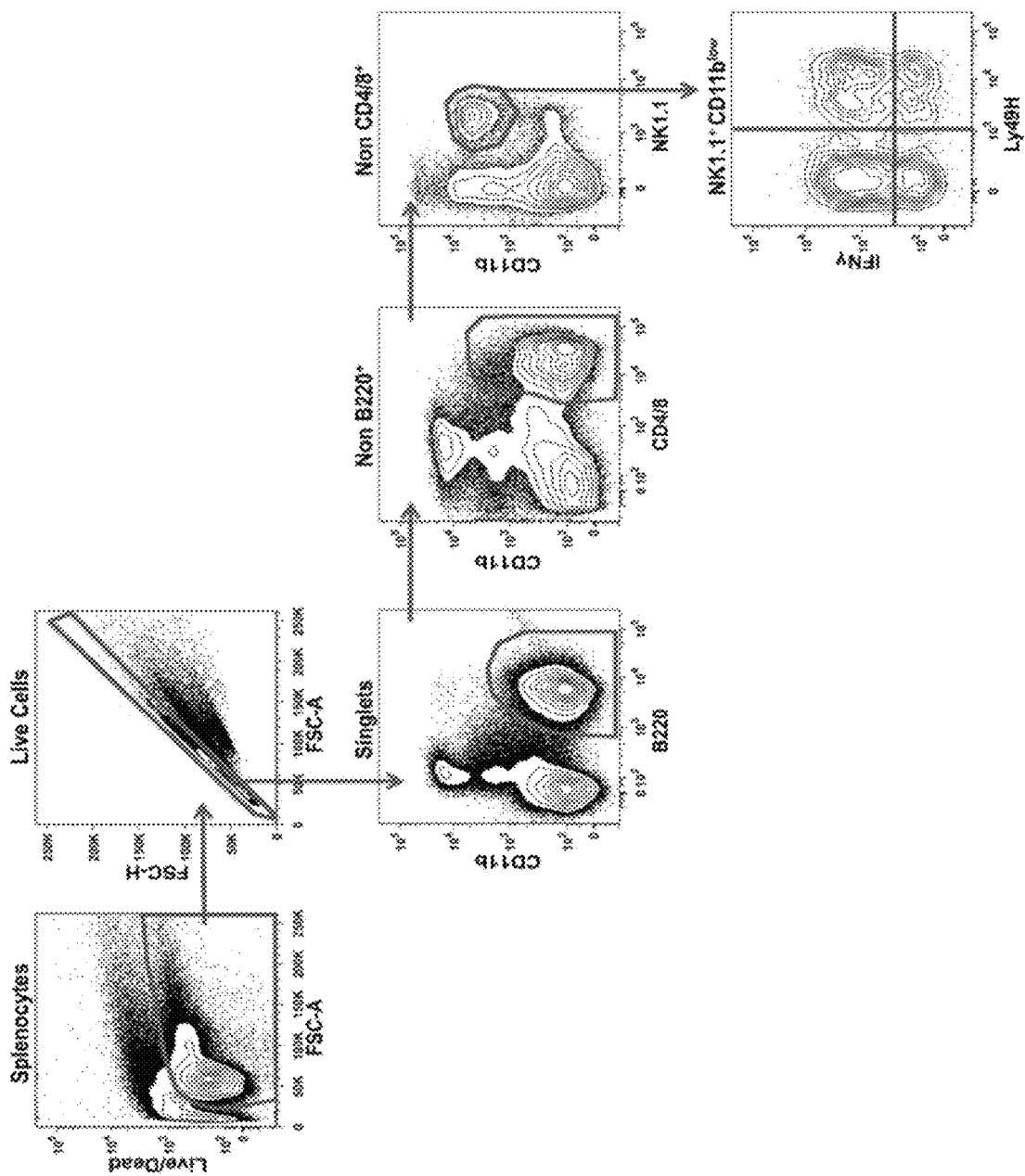
FIG. 13. A gating strategy for immunophenotyping of splenocytes. Splenocytes obtained 36 h after MCMV infection were gated according to established cell surface markers, as indicated.

Aim2–/– mice are severely impaired in mounting an efficient host response to MCMV infection, due to a deficiency in the inflammasome-dependent systemic IL-18 release. IL-18 acts in synergy with IL-12 to stimulate IFN-γ production by splenic NK cells, which is crucial for the early anti-viral response against DNA viruses, including MCMV. WT and CD68-POP3 TG mice were challenged with MCMV, and, similar to Aim2 deficiency, serum IL-18 and IFN-γ concentrations were also strongly decreased in CD68-POP3 expressing mice at 36 hours post i.p. infection. However, TNF serum concentrations were not affected (FIG. 12a). CD68-POP3 TG mice displayed a similar spleen weight as WT mice after MCMV infection, but showed slightly reduced splenocyte numbers (FIG. 12b). IL-18 is required for Ly49H+NK cell expansion (Andrews et al. Nat Immunol. 2003; 4:175-81; herein incorporated by reference in its entirety). Reduced IL-18 concentration in CD68-POP3 TG mice was observed in experiments conducted during development of embodiments described herein (FIG. 12a). CD68-POP3 TG mice displayed a decreased number of NK1.1+Ly49H+ cells, whereas NK1.1+Ly49H− cells were increased. However, comparable numbers of T and B cells were found (FIG. 12c and FIG. 13). Accordingly, CD68-POP3 TG mice had significantly less IFN-γ producing splenic NK cells ex vivo at 36 hours post infection (FIG. 12d, e), reminiscent of Aim2−/− mice 6. This response was specific to MCMV and not due to an intrinsic defect of splenic NK cells from CD68-POP3 TG mice to produce IFN-γ, since activation of WT and POP3 splenic NK cells with the phorbol ester PMA and ionomycin ex vivo, produced comparable numbers of IFN-γ+ NK cells (~95%) (FIG. 12e). In addition to impaired IL-18 and IFN-γ production, CD68-POP3 TG mice displayed elevated serum IFN-β concentration at early (11 hours), but not at later time points (36 hours) post MCMV infection (FIG. 12f). These results indicate that the deficient IFN-γ response is due to impaired systemic IL-18 observed in CD68-POP3 TG mice upon MCMV infection. Significant increase in the splenic MCMV titer in CD68-POP3 TG mice was observable (FIG. 12g). The 2-fold increase was comparable to the 2-fold increase observed in Asc−/− mice in a previously published experiment (Rathinam V A, et al. Nat Immunol. 2010; 11:395-402; herein incorporated by reference in its entirety).

Figure 14A:
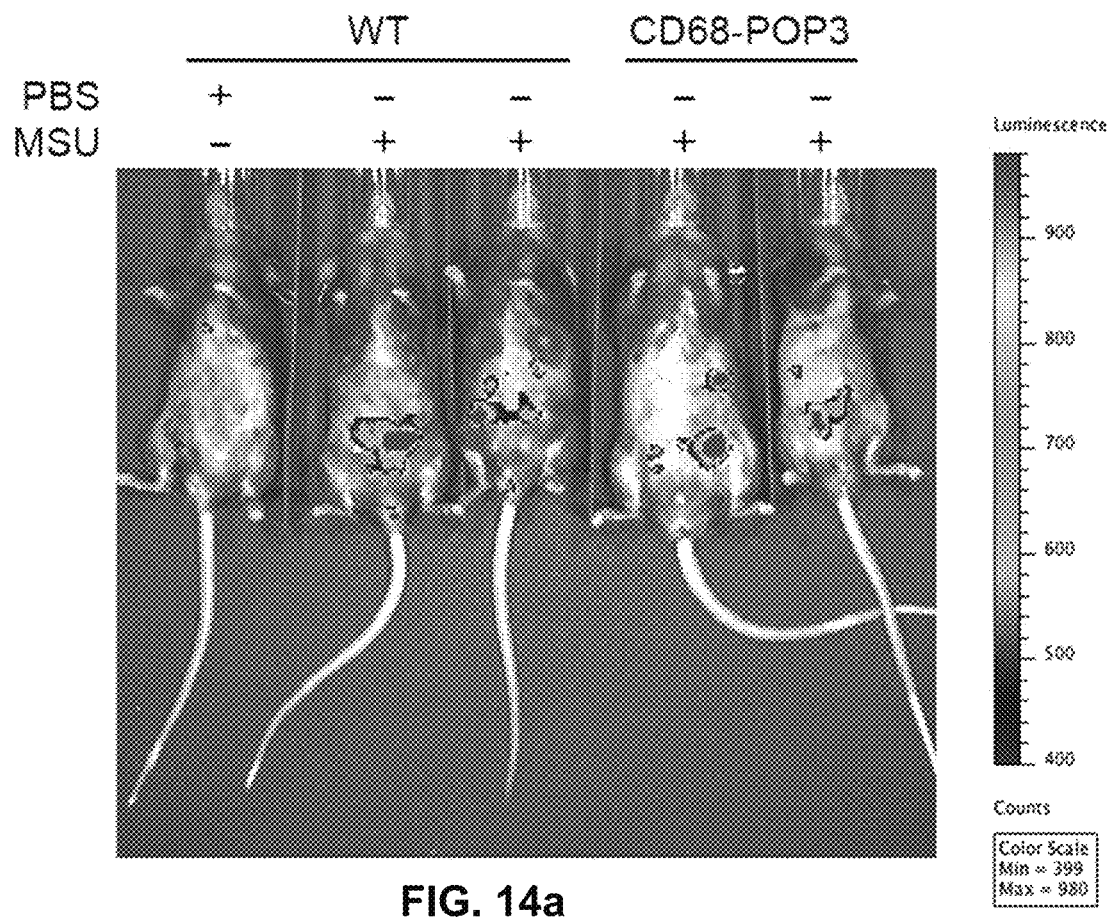
FIGS. 14a-b. POP3 does not ameliorate MSU-induced peritonitis. (a) WT and CD68-POP3 TG mice were i.p. injected with PBS or MSU crystals (10 mg/mouse) and mice were imaged for MPO activity in vivo 5 h later (n=3-7), showing representative examples. (b) Model of the type I IFN-induced regulatory loop of cytosolic DNA-induced inflammasome response that involves POP3.
Figure 14B:
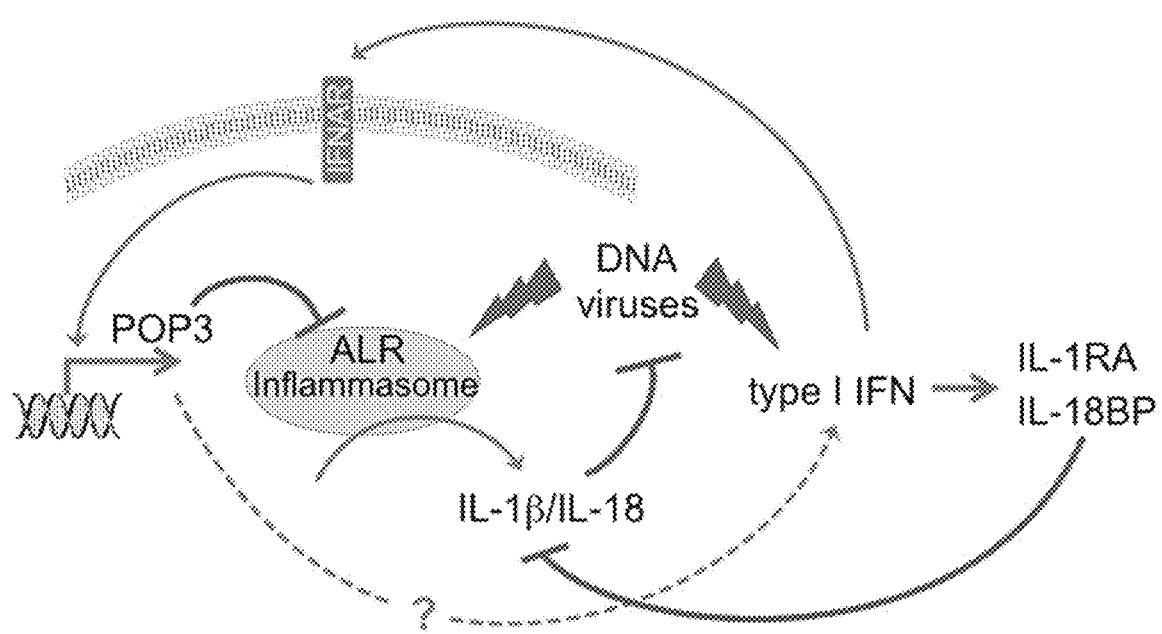

A functional specificity of POP3 for ALRs is further supported by the observation that WT and CD68-POP3 TG mice did not show significant differences in their response to MSU crystal-challenge in vivo. Severity of MSU-induced peritonitis was comparable in both genotypes, showing similar peritoneal IL-1β concentrations 7 hours after MSU challenge (FIG. 12h). IL-1β produced by macrophages is essential for neutrophil infiltration into the peritoneal cavity (McDonald B, et al. Science. 2010; 330:362-366; herein incorporated by reference in its entirety); no differences in neutrophil infiltration were observed in vivo by utilizing a luminescent myeloperoxidase (MPO) probe (FIG. 12i, FIG. 14a). These results clearly demonstrate that POP3 has a critical role in the host response to MCMV through regulating the AIM2 inflammasome in vivo, without functionally affecting the NLRP3 inflammasome. Data demonstrate that POP3 functions in the anti-viral host response within a type I IFN-mediated inflammasome regulatory feedback loop (FIG. 14b).

Example 2

The PYRIN Domain-Only Protein POP1 Inhibits Inflammasome Assembly and Ameliorates Inflammatory Disease Animals pCD68-POP1 was generated by replacing CAT in pCAT-Basic containing the human CD68 promoter and the macrophage-specific IVS-1 enhancer (Khare et al. Nat Immunol 15, 343-353 (2014); Iqbal et al. Blood blood-2014-04-568691 (2014); herein incorporated by reference in their entireties) with GFP-POP1 and flanking the cassette with AatII restriction sites. The AatII fragment was excised, purified and B6.TgN(CD68-POP1) TG mice were generated by pronuclear injection into C57BL/6 embryos by the Northwestern University Transgenic and Targeted Mutagenesis Facility. C57BL/6 wild type (WT) and Lysozyme M-Cre knock-in mice (CreL) were obtained from the Jackson Laboratories and NLRP3$^{-/-}$, ASC$^{-/-}$ and floxed NLRP3$^{A350V}$ knock-in mice were described earlier (Mariathasan et al. Nature 430, 213-8 (2004); Mariathasan et al. Nature 440, 228-232 (2006); Brydges et al Immunity 30, 875-87 (2009); herein incorporated by reference in their entireties). Mice were housed in a specific pathogen-free animal facility and all experiments were performed on age and gender-matched, randomly assigned 8-14 week old mice conducted according to procedures approved by the Northwestern University Committee on Use and Care of Animals.

Human Subjects

Available datasets of septic and CAPS patients in the NCBI Gene Expression Omnibus (GEO) database were searched for the inclusion of POP1 and were analysed for expression of POP1 and ASC with GEO2R. GEO accession number GDS3085 contains expression data of leukocytes of critically ill adult patients not diagnosed with sepsis (n=17), diagnosed with Gram negative, Gram positive or mixed sepsis (n=55) that were analysed using CompuGen Human OligoLibrary V1.0 (Tang et al. Crit Care Med 36, 1125-8 (2008); herein incorporated by reference in its entirety). GEO accession number GSE13904 contains expression data obtained from whole blood drawn from pediatric healthy controls (n=18) and patients diagnosed with systemic inflammatory response syndrome (SIRS), sepsis or septic shock (n=209) that were analysed with the Affymetrix Human Genome U133 Plus 2.0 Array (Wong et al. Crit Care Med 37, 1558-66 (2009); herein incorporated by reference in its entirety). GEO accession number GSE40561 contains expression data obtained from whole blood drawn from CINCA (n=2) and MWS (n=5) that were analysed using Illumina human HT-12 beadchips (Boisson et al. Nat Immunol 13, 1178-86 (2012); herein incorporated by reference in its entirety). GEO accession number GSE3284 contains expression data of leukocytes isolated at the indicated times from human healthy male and female subjects (n=8) after intravenous administration of NIH Clinical Center Reference endotoxin (CC-RE-Lot 2) (2 ng/kg body weight) over a 5 min period that were analyzed with Affymetrix Hu133A and Hu133B oligonucleotide array (Calvano et al. Nature 437, 1032-7 (2005); herein incorporated by reference in its entirety).

Macrophage Isolation, Culture and Transfection

Peripheral blood-derived hMΦ were isolated from healthy donor blood after obtaining informed consent under a protocol approved by Northwestern University Institutional Review Board by Ficoll-Hypaque centrifugation (Sigma) and countercurrent centrifugal elutriation in the presence of 10 µg/ml polymyxin B using a JE-6B rotor (Beckman Coulter), as described (Khare et al. Nat Immunol 15, 343-353 (2014); herein incorporated by reference in its entirety). Bone marrow cells flushed from femurs were differentiated into BMDM with GM-CSF either in recombinant form (100 ng/ml; Peprotech), or conditioned medium from L929 (25%) in DMEM medium supplemented with 10% heat inactivated FCS (Invitrogen), 5% horse serum (Gibco) and analyzed after 7 days. Peritoneal macrophages (PM) were obtained by peritoneal lavage. HEK293 and THP-1 cells were obtained from ATCC and were routinely tested for mycoplasma contamination by PCR. hΦ were transfected in 24-well dishes ($3.3 \times 10^5$ cells) with 100 nM siRNA duplexes (F2/virofect; Targeting Systems) and analyzed 72 hr posttransfection (POP1 siRNA sense strand: 5'-ccuccuacuacgaggacuatt-3' and Ctrl siRNA F, Santa Cruz, Qiagen), as described (Khare et al. Nat Immunol 15, 343-353 (2014); herein incorporated by reference in its entirety). Transfection efficiency was confirmed by qPCR. THP-1 cells were stably transduced with pLEX or pLKO-based lentiviral particles using magnetic beads (ExpressMag, Sigma) and selected with Puromycin. Recombinant lentivirus was produced in HEK293-lenti cells (Clontech) by Xfect-based transfection (Clontech) with pLKO or pLEX and the packaging plasmids pMD.2G and psPAX2 (Addgene plasmids 12259 and 12260), followed by concentration of virus-containing conditioned medium (Lenii-X Concentrator, Clontech). POP1 shRNA #1: 5'-ccggtcctactacgaggactacgcactcgagtgcgtagtcctcgtagtaggatttttg-3' (TRC N0000423651; SEQ ID NO: 8); POP1 shRNA #3: 5'-ccggacaagctggtcgcctcctactctcgagagtaggaggcgaccagcttgttttttg-3' (TRC N0000436892; SEQ ID NO: 9) and a non-targeting scrambled control shRNA (Sigma). hMΦ, THP-1 cells, BMDM and PM were treated for the indicated times with 600 ng/mL E. coli LPS (0111:B4, Sigma) or pre-treated with ultra-pure E. coli LPS (0111:B4; Invivogen) (100 ng/mL), recombinant IL-1β (10 ng/ml, Millipore), recombinant IL-1Ra (anakinra, 10 mg/mL, Amgen), MDP (20 ug/mL; Invivogen), CPPD (125 ug/ml; Invivogen), Cholera Toxin B subnit (CTB) (10 ug/ml; List Biological Laboratories) for 16 h. Cells were transfected with poly(dA:dT) (2 ng/mL; Sigma), Salmonella thyphimurium flagellin (140 ng/mL; Invivogen), ultra-pure E. coli LPS (0111:B4; Invivogen) (1000 ng/mL) using Lipofectamine 2000 (Invitrogen). Where indicated, cells were pulsed for 20 min with ATP (5 mM; Sigma) or treated for 45 min with nigericin (5 μM). In caspase-1 inhibition studies, the caspase-1 inhibitor zYVAD-fmk was added to cells 30 min prior stimulation with LPS. LPS-primed cells were incubated for 3 h in K±free medium containing 0.8 mM $MgCl_2$, 1.5 mM $CaCl_2$), 10 mM HEPES, 5 mM Glucose, 140 mM NaCl, pH 7.2.

LPS-Induced Peritonitis 8-12 weeks old female WT and CD68-POP1 TG mice had their abdomen shaved under anaesthesia, and were randomly selected for i.p. injection with PBS or LPS (2.5 mg/kg, E. coli 0111:B4, Sigma). After 3 h, mice were i.p. injected with XenoLight Rediject Inflammation probe (200 mg/kg, PerkinElmer) (Gross et al. Nat Med 15, 455-61 (2009); herein incorporated by reference in its entirety) and in vivo bioluminescence was captured by imaging (IVIS Spectrum, PerkinElmer) 10 min post injection with a 5 min exposure on anesthetized mice. Images were quantified with Living Image software (PerkinElmer). Endotoxic shock was induced by i.p. injection of a lethal dose of 20 mg/kg LPS (E. coli 0111:B4) and mice were monitored 4 times daily for survival. Body temperature was measured with an animal rectal probe. Blood was collected 3 h post LPS injection by mandibular bleed, and serum cytokine levels were quantified by ELISA.

Cryopyrinopathy

Floxed $NLRP3^{A350V}$ mice (Brydges et al. Immunity 30, 875-87 (2009); Brydges et al. J Clin Invest 123, 4695-4705 (2013); herein incorporated by reference in their entireties) were crossed with Lysozyme M-Cre recombinase (CreL) and CD68-POP1 TG mice and male and female offsprings analysed for body weight and survival. Histological analysis was performed at day 8 after birth.

ASC-GFP Particle Purification

HEK293 cells were infected with an ASC-GFP-expressing lentivirus as described above. Total cell lysates were prepared by hypotonic lysis (20 mM HEPES-KOH, pH 7.5, 5 mM $MgCl_2$, 0.5 mM EGTA, 0.1% CHAPS, supplemented with protease inhibitor) and aggregation of ASC-GFP was induced by incubation of cell lysates at 37° C. for 30 min as previously described (Fernandes-Alnemri et al. Methods Enzymol 442, 251-270; herein incorporated by reference in its entirety). ASC-GFP particles were sorted by flow cytometry and polymerization of ASC-specks was confirmed by fluorescent microscopy. HEK293 cells transiently transfected with ASC-GFP and RFP-POP1. were used for isolation of ASC/POP1 particles. LPS-primed THP-1 cells were treated with $2 \times 10^3$ particles for 16 h.

ASC-Particle-Induced Peritonitis 14 weeks old male WT and CD68-POP1 TG mice had their abdomen shaved under anaesthesia, and were randomly selected for i.p. injection with PBS or FACS-purified ASC-GFP particles ($1 \times 10^5$ particles/mouse). After 4 h, mice were i.p. injected with XenoLight Rediject Inflammation probe (200 mg/kg, PerkinElmer) (Gross et al. Nat Med 15, 455-61 (2009); herein incorporated by reference in its entirety) and in vivo bioluminescence was captured by imaging (IVIS Spectrum, PerkinElmer) 10 min post injection with a 5 min exposure on anesthetized mice[15]. Images were quantified with Living Image software (PerkinElmer). Peritoneal lavage fluids were collected and assayed for IL-1β by ELISA.

Plasmids pcDNA3 and pGEX-based expression constructs for ASC, POP1, NLRP3, $ASC^{PYD}$ and NLRP3PYD were described earlier (Stehlik et al. J. Immunol 171, 6154-63 (2003); Khare et al. Nat Immunol 15, 343-353 (2014); Stehlik et al. Biochem. J 373, 101-113 (2003); herein incorporated by reference in their entireties).

Antibody-Based Detection

Rabbit polyclonal and mouse monoclonal POP1 antibodies were custom raised, rabbit polyclonal antibody to ASC (Santa Cruz Biotech), mouse monoclonal antibody to ASC (custom), mouse polyclonal antibody to caspase-1 (Santa Cruz Biotech clone M-20), mouse monoclonal antibody to GFP (Santa Cruz Biotech clone B-2), mouse monoclonal antibody to myc (Roche and Santa Cruz Biotech clone 9E10), mouse monoclonal antibody to HA (Santa Cruz Biotech clone F-7), rabbit polyclonal antibody to IL-1β (Santa Cruz Biotech), rabbit polyclonal antibodies to IκBα (clone 44D4)/p-IκBα (clone 14D4), JNK (clone 9252)/p-JNK (9251), p38 (clone 9212)/p-p38 (clone 12F8), p42/44 (clone 9102)/p-p42/44 (9101) (all Cell Signaling Technology) and mouse monoclonal antibody to β-tubulin (Santa Cruz Biotech clone TU-02), mouse monoclonal antibody to GST (Santa Cruz Biotech clone B-14), mouse monoclonal antibody to β-actin (Sigma clone AC-74) and mouse monoclonal antibody to NLRP3 (Adipogen clone Cryo-2) were used for immunoblot.

Co-immunoprecipitation (IP): HEK293 cells were transfected with GFP, GFP-POP1, HA-ASC, MYC-NLRP3, HA-$ASC^{PYD}$, MYC-$ASC^{PYD}$ or empty plasmid in 100 mm dishes using Lipofectamine 2000 (Invitrogen). 24 h post transfection, cells were lysed under hypotonic conditions (20 mM HEPES pH 7.4, 10 mM KCl, 1 mM EDTA, supplemented with protease inhibitors) using a 231/2 G syringe needle, cleared and adjusted to 50 mM Hepes pH 7.4, 150 mM NaCl, 10% Glycerol, 2 mM EDTA, 0.5%

Triton X-100, supplemented with protease inhibitors, and subjected to IP by incubating with sepharose immobilized antibodies as indicated for 16 h at 4° C., followed by extensive washing with lysis buffer. Bound proteins were separated as above. TCL (5-10%) were also analyzed where indicated. Endogenous NLRP3 inflammasome complexes were similarly purified from ultrapure LPS-primed (16 h, 100 ng/mL) THP-1 cells following nigericin treatment (45 mM, 5 µM).

GST pull down: POP1 was expressed from pGEX-4T1 and affinity purified as a GST fusion protein from *E. coli* BL21 (Stehlik et al. Biochem. J 373, 101-113 (2003); herein incorporated by reference in its entirety). Protein lysates were prepared from LPS-treated (16 h) BMDM or THP-1 cells by lysis (50 mM Hepes pH 7.4, 120 mM NaCl, 10% Glycerol, 2 mM EDTA, 0.5% Triton X-100, supplemented with protease inhibitors), and cleared lysates were incubated with immobilized GST-POP1 or GST control for 16 h at 4° C., followed by extensive washing with lysis buffer and analysis as above.

ASC cross-linking: $4 \times 10^6$ BMDM were seeded in 60 mm plates and subjected to cross-linking. Cells were either left untreated or treated with LPS (4 h) and pulsed with ATP (20 min), culture SN were removed, cells rinsed with ice-cold PBS and lysed (20 mM Hepes pH 7.4, 100 mM NaCl, 1% NP-40, 1 mM sodium orthovanadate, supplemented with protease inhibitors) and further lysed by shearing. Cleared lysates were stored for immunoblot analysis and the insoluble pellets were resuspended in 500 µl PBS, supplemented with 2 mM disuccinimydyl suberate (DSS, Pierce) and incubated with rotation at room temperature for 30 min Samples were centrifuged at 5,000 rpm for 10 min at 4° C. and the cross-linked pellets were resuspended in 50 µl Laemmli sample buffer and analyzed by immunoblot.

Immunohistochemistry: Human lung tissue was embedded in paraffin, cut into 3 µm sections, mounted, deparaffinized and immunostained with mouse monoclonal CD68 (Dako) and rabbit polyclonal POP1 (custom raised) and peroxidase (HRP)/DAB$^+$ and alkaline phosphatase (AP)/Fast Red enzyme/chromogen combinations (Dako) and specific isotype controls (Dako) and hematoxylin counterstaining of nuclei. Mouse tissues were dissected, fixed in 10% formalin, embedded in paraffin, sectioned and stained with hematoxylin and eosin (H&E) at the Northwestern University Mouse Histology and Phenotyping Laboratory.

ELISA: IL-1α, IL-1β, IL-18 and TNFα secretion was quantified from clarified culture SN obtained from hMΦ, THP-1 cells, BMDMs, PM and from mouse serum by ELISA (BD Biosciences, eBiosciences, Invitrogen). Samples were analyzed in triplicates and repeated at least three times, showing a representative result.

Flow cytometry: Blood was collected into EDTA-containing tubes either via facial vein bleed (from live animals) or via cardiac puncture (from euthanized animals). Whole blood was stained with fluorochrome-conjugated antibodies and erythrocytes were then lysed using BD FACS lysing solution (BD Biosciences). Cells from the peritoneal cavity were harvested after lavage of the peritoneal cavity with 10 ml of ice-cold MACS buffer. Bone marrow was harvested from femurs and tibias. Spleen and lungs were digested using mixture of Collagenase D and DNase I (Roche) in HBSS at 37° C. for 30 min and filtered through 40 µm nylon mesh. Erythrocytes were lysed using BD Pharm Lyse (BD Biosciences) and cells were counted using Countess automated cell counter (Invitrogen). Dead cells were discriminated using trypan blue. Cells were stained with live/dead Aqua (Invitrogen) or eFluor 506 (eBioscience) viability dyes, incubated with FcBlock (BD Bioscience) and stained with fluorochrome-conjugated antibodies. Data were acquired on a BD LSR II flow cytometer (BD Biosciences). Compensation and analysis of the flow cytometry data were performed using FlowJo software (TreeStar). "Fluorescence minus one" controls were used when necessary to set up gates.

Active caspase-1: Cells were primed with LPS for 4 h, followed by a 20 min pulse with ATP. After 1 h incubation in fresh medium, active caspase-1 p10 was detected in 10% TCA precipitated culture supernatants (SN). Total cell lysate (TCL) and concentrated culture SN pellets were resuspended in Laemmli buffer. Samples were separated by SDS-PAGE, transferred to PVDF membranes and analyzed by immunoblotting with indicated antibodies and HRP-conjugated secondary antibodies, ECL detection (Pierce), and image acquisition (Ultralum). Alternatively, cells were incubated with biotin-conjugated YVAD-CMK (Anaspec) for 30 min at 37° C. with 5% CO2 before LPS priming (40 min) and ATP stimulation (20 min). Alexa Fluor 647 conjugate streptavidin (Molecular Probes) was used to quantify active caspase-1 by flow cytometry.

Lactate Dehydrogenase (LDH) Release

Cleared culture supernatants were analyzed for LDH release as a measurement for pyroptosis by colorimetric enzyme activity assay accordingly to the manufacturer's instructions (Clontech LDH cytotoxicity detection assay).

Cell Penetrating Recombinant Proteins

6xHIS-POP1 and a 6xHIS-GFP cDNAs in pET28a (Invitrogen) were fused with the HIV TAT sequence (YGRKKRRQRRR (SEQ ID NO: 10)) by standard PCR, produced under native conditions in *E. coli* BL21 after induction with 2 mM IPTG for 4 h and affinity purified on Talon columns (Invitrogen) in the presence of 10 mM imidazole (pH 6.5), eluted with 1 M imidazole and further purified by anion exchange chromatography (pH6.5, Macro-Prep High S, Biorad) to eliminate endotoxin, which was verified by the LAL assay, desalting (Econo-Pac columns 10DG, Biorad) and protein concentration (Nanosep 3 k, Pall Life Sciences). C57BL/6 mice were i.p. injected with 50 µg TAT-GFP, followed by peritoneal lavage after 1 h and FACS analysis with the indicated lineage markers for uptake control. 12 weeks old male WT mice had their abdomen shaved under anaesthesia, were randomly selected for i.p. injection with TAT-GFP or TAT-POP1 (40 µg/kg) for 30 min prior LPS i.p. injection (2.5 mg/kg, *E. coli* 0111:B4, Sigma), and were quantified for MPO activity in vivo 1 h later, as described above.

Quantitative Real-Time PCR

Total RNA was isolated from hMΦ, BMDM or THP-1 cells using Trizol reagent (Invitrogen) and from mouse peripheral blood using the mouse RiboPure-blood RNA isolation kit (Invitrogen), treated with DNase I, reverse transcribed with GoScript (Promega) and analyzed by TaqMan Real-time gene expression system using predesigned FAM labeled primer/probes on an ABI 7300 Real time PCR machine (Applied Biosystems) and displayed as relative expression compared to β-actin.

IL-1 (Induced Expression of POP1 is Reduced in Inflammatory Disease Patients

NLRP3 inflammasome activity is required for homeostasis in several tissues, including the lung and contributes to the pathology of lung inflammation (De Nardo et al. Am J Pathol 184, 42-54 (2014); herein incorporated by reference in its entirety). POP1 expression was found in human lung tissue, particularly in CD68$^+$ alveolar macrophages (Me) by immunohistochemistry (FIG. 15a), using a custom raised antibody that neither cross reacts with other POPs (Khare et al. Nat Immunol 15, 343-353 (2014); herein incorporated by reference in its entirety), nor with the highly similar ASCPYD (FIG. 16a, b). Lung infections commonly lead to sepsis, which also causes secondary acute lung injury, and excessive inflammasome activation contributes to sepsis in human and mice (Kayagaki et al. Nature 479, 117-21 (2011); Exline et al. PLoS One 9, e90968 (2014).); herein incorporated by reference in their entireties). Thus, POP1 expression was determined in leukocytes from septic patients in two different cohorts (Tang et al. Crit Care Med 36, 1125-8 (2008); Wong et al. Crit Care Med 37, 1558-66 (2009); herein incorporated by reference in their entireties), where POP1 was expressed up to 34% less compared to healthy controls (FIG. 15b, c). Cryopyrinopathies (or Cryopyrin-associated periodic syndromes; CAPS) are caused by mutations in NLRP3 and are directly linked to the NLRP3 inflammasome (Hoffman et al. Nat Genet 29, 301-5 (2001); herein incorporated by reference in its entirety). We found that CAPS patients (Boisson et al. Nat Immunol 13, 1178-86 (2012); herein incorporated by reference in its entirety) displayed significantly lower POP1 expression compared to healthy controls (FIG. 15d). Overwhelming evidence supports the necessity for a balanced NLRP3 inflammasome response to maintain homeostasis (Henao-Mejia et al. Nat Immunol 13, 321-4 (2012); herein incorporated by reference in its entirety). LPS-induced late response gene expression of POP1 was observed in primary human (h) MΦ (FIG. 15e) and THP-1 cells (FIG. 16c), but contrary to POP3, POP1 was not up-regulated in response to IFN-β, which emphasizes the distinct function of individual POPs. Notably, POP1 expression peaked right before the inducible expression of HMGB1 (FIG. 15e), which is released through pyroptosis and is a key mediator of sepsis (Wang et al. Science 285, 248-51 (1999); herein incorporated by reference in its entirety). Thus, the late response expression of POP1 potentially enables inflammasome functions in early host defense and may provide a mechanism to counter excessive release of late mediators that perpetuate systemic inflammation. This LPS-inducible expression of POP1 was also observed in leukocytes isolated from human subjects following LPS infusion in vivo (Calvano et al. Nature 437, 1032-7 (2005); herein incorporated by reference in its entirety) (FIG. 15f). LPS is a potent activator of IL1B transcription through IκBβ-regulated NF-κB activation (Scheibel et al. J Exp Med 207, 2621-30 (2010); herein incorporated by reference in its entirety), and IL-1β acts downstream of LPS in an autocrine loop in platelets (Brown et al. J Immunol 191, 5196-203 (2013); herein incorporated by reference in its entirety). Experiments were conducted during development of embodiments described herein to determine wwhether IL-1β plays a role in LPS-induced transcription of POP1. Pre-treatment of hMΦ with the IL-1 receptor antagonist anakinra prevented the LPS-inducible expression of POP1 (FIG. 15g), indicating that LPS-induced autocrine and paracrine IL-1β signalling occurs also in hMΦ and that IL-1β is responsible for the inducible expression of POP1. Accordingly, POP1 expression was also elevated in hMΦ after IL-1β treatment (FIG. 15h), confirming that IL-1β drives POP1 expression in an inflammasome regulatory feedback loop.

POP1 Inhibits Inflammasome-Mediated Cytokine Release in Human Macrophages

Figure 17A:
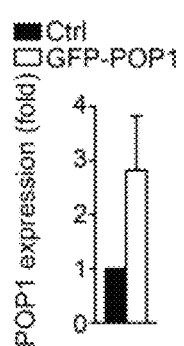
Figure 17E:
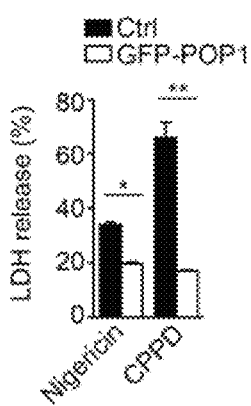
Figure 17H:
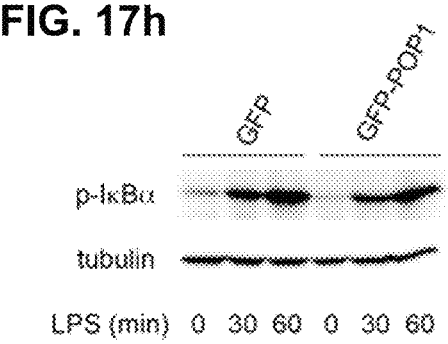
Figure 17I:
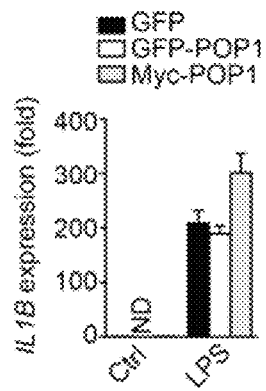
Figure 17C:
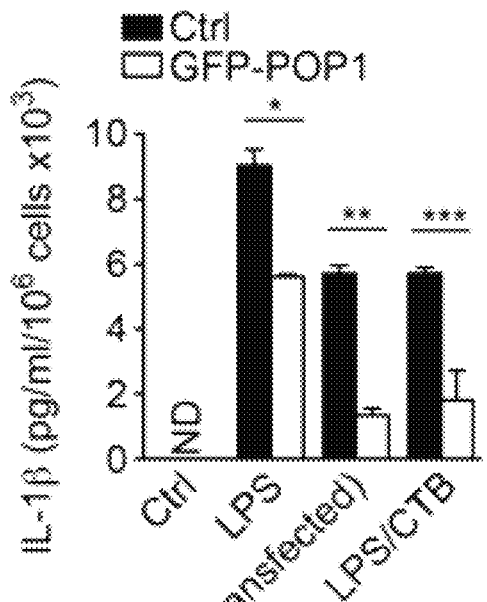
Figure 17D:
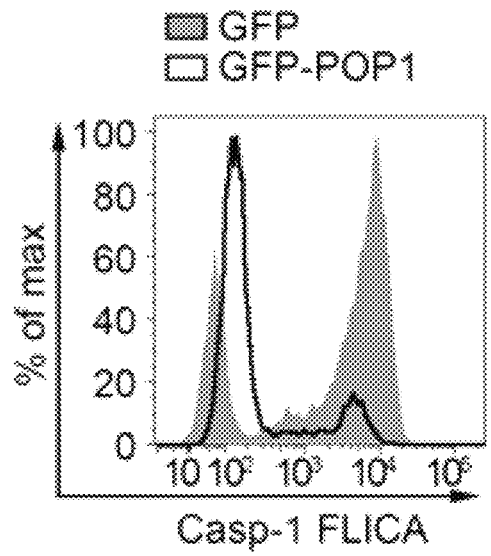
Figure 17G:
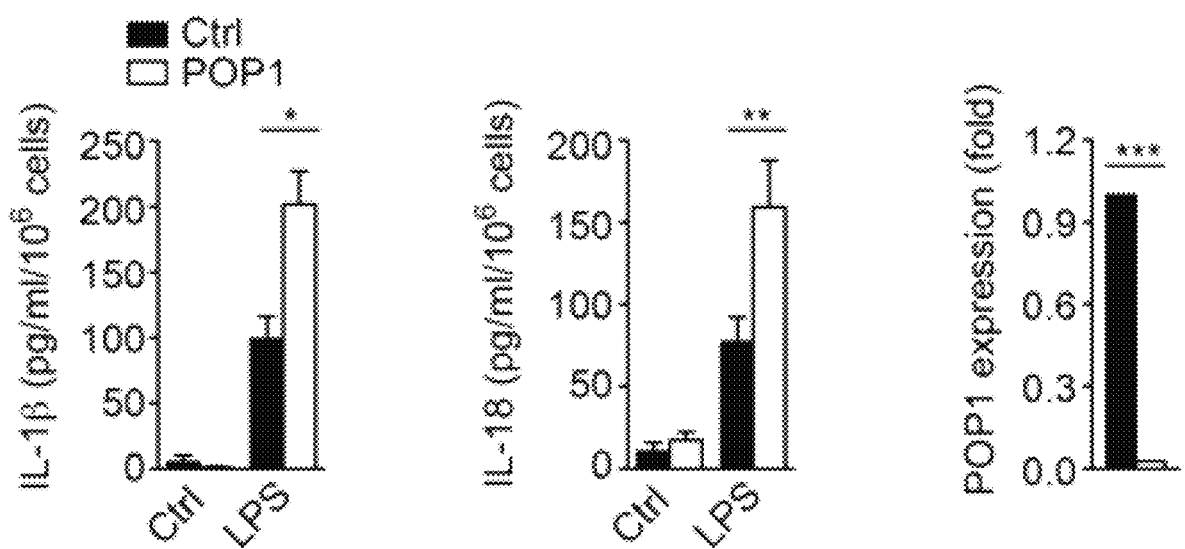

To investigate the role of POP1 in NLRP3 inflammasome activation a human monocytic THP-1 cell line stably expressing POP1 (THP-1$^{GFP-POP1}$) was generated, which was confirmed by qPCR (FIG. 17a). THP-1$^{GFP-POP1}$ revealed diminished secretion of mature IL-1β in response to NLRP3 activation with nigericin, CPPD or K$^+$ depletion, and in response to activation of the AIM2, NLRC4 and NLRP1 inflammasomes with poly(dA:dT) transfection, flagellin transfection or with MDP treatment in LPS-primed cells, respectively (FIG. 17b). Furthermore, POP1 blocked IL-1β release by the non-canonical inflammasome in response to cytosolic LPS upon LPS treatment, cytosolic LPS upon LPS transfection or cytosolic delivery of LPS with cholera toxin subunit B (CTB) (FIG. 17c). Comparable results were obtained for myc-tagged POP1 (FIG. 16d). Accordingly, THP-1$^{GFP-POP1}$ cells also showed markedly blunted NLRP3-mediated caspase-1 activity in LPS-primed and nigericin-treated cells (FIG. 17d), and consequently reduced LDH release (FIG. 17e). Conversely, stable shRNA-mediated POP1 silencing in THP-1 cells (THP-1$^{shPOP1}$) resulted in elevated IL-1β release in response to LPS and POP1 silencing was confirmed by qPCR (FIG. 17f). Similarly, siRNA-mediated silencing of POP1 in hMΦ resulted in elevated release of IL-1β and IL-18 in response to LPS and POP1 silencing was confirmed by qPCR (FIG. 17g). In vitro experiments with POP1 in epithelial cell lines showed an inhibitory effect on NF-κB activation (Stehlik et al. Biochem. J 373, 101-113 (2003); incorporated by reference in its entirety). TLR-mediated NF-κB priming is necessary for NLRP3 inflammasome activation (Bauernfeind et al. J Immunol 183, 787-91 (2009); Juliana et al. J Biol Chem 287, 36617-22 (2012); Schroder et al. Immunobiology 217, 1325-9 (2012); herein incorporated by reference in their entireties), but, in contrast to over-expression in epithelial cell lines, stable POP1 expression in THP-1 cells did neither affect phosphorylation of IκBc (FIG. 17h) nor transcription of IL1B (FIG. 17i) in response to LPS, thus implicating POP1 in directly regulating the NLRP3 inflammasome in MΦ.

POP1 Blocks NLRP3'-Mediated ASC' Nucleation in Human Macrophages

Figure 18A:
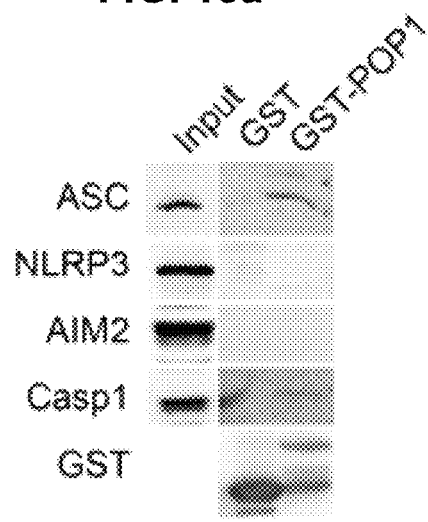
FIGS. 18a-e. POP1 inhibits nucleation of the NLRP3 inflammasome in human macrophages. a, Interaction of GST-POP1 with endogenous ASC in THP-1 total cell lysates (TCL) using GST as negative control and showing 10% TCL as input. b, Immunoprecipitation (IP) of proteins, with antibody to ASC, from HEK293 cells transfected to express NLRP3, ASC and POP1 as indicated, followed by immunoblot analysis alongside TCL. c, IP of proteins, with antibody to ASC or with control immunoglobulin G (IgG), from LPS primed and nigericin-treated THP-1 cells stably expressing GFP or GFP-POP1, followed by immunoblot analysis alongside total TCL. d, IP of proteins, with antibody to HA, from HEK293 cells transfected to express Myc-ASC, HA-ASCPYD and GFP-POP1 as indicated, followed by immunoblot analysis alongside TCL. e, Immunoblot of HA-ASCPYD and GFP-POP1, as indicated, after protein cross linking; data are representative of two (a-c), three (d), and one (e) replicates.
Figure 18B:
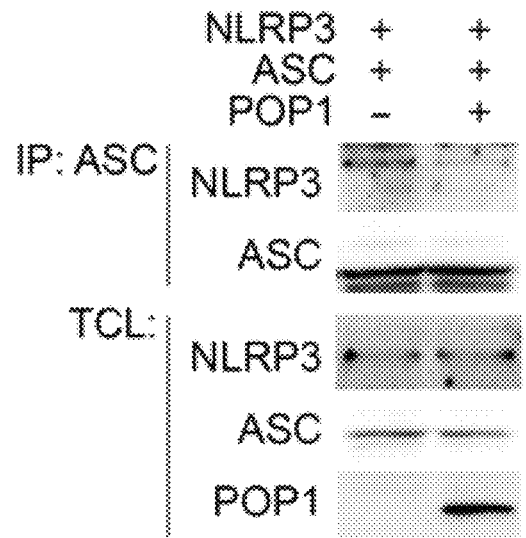
Figure 18C:
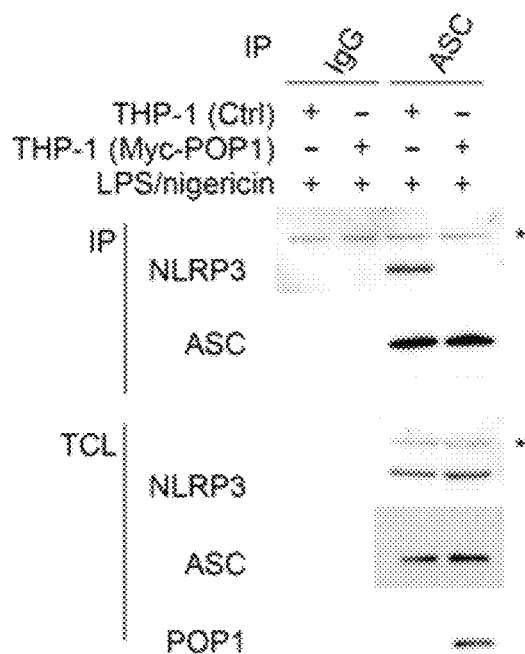
Figure 18D:
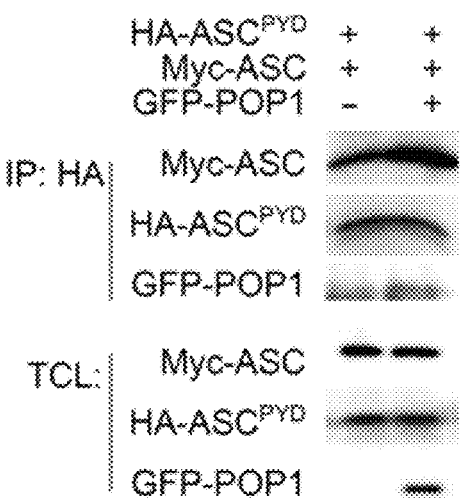
Figure 18E:
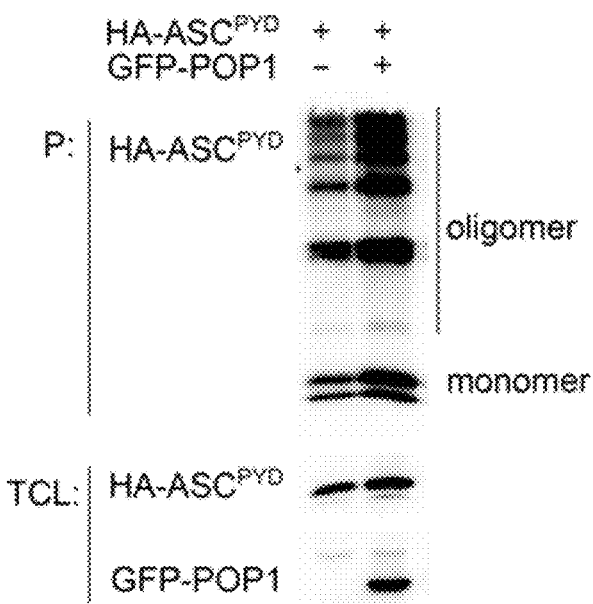

Recruitment of ASC to upstream sensors is essential for inflammasome activation. POP1 specifically bound to endogenous ASC, but not to the PYD-containing PRRs NLRP3 and AIM2 in LPS-primed THP-1 cells (FIG. 18a), emphasizing the selectivity of these interactions. POP1 also indirectly co-purified pro-caspase-1, and since POP1 interacts with the ASCPYD, which did not affect the CARD-mediated binding of ASC to caspase-1 (FIG. 18a). Binding of ASC to NLRP3 induces ASC$^{PYD}$ nucleation, which provides the oligomeric platform essential for caspase-1 activation (Lu et al. Cell 156, 1193-206 (2014); Cai et al. Cell 156, 1207-22 (2014); herein incorporated by reference in their entireties). Co-expression of POP1 with ASC and NLRP3 in HEK293 cells strongly reduced the binding of ASC with NLRP3, as determined by co-immunoprecipitation (coIP) (FIG. 18b). Furthermore, in LPS-primed THP-1$^{GFP-POP1}$ cells the nigericin-induced interaction of endogenous NLRP3 and ASC is prevented, indicating that POP1 can prevent NLRP3-mediated nucleation of ASC (FIG. 18c). POP1 binding to the ASC$^{PYD}$ could also directly prevent ASC$^{PYD}$ self-polymerization. However, coIP experiments between Myc-ASC and HA-ASC' in the presence or absence of POP1 revealed that POP1 did not impair the ASC$^{PYD}$ self-interaction, although POP1 interacts with the ASC$^{PYD}$ (FIG. 18d). ASC can spontaneously nucleate and polymerize upon overexpression[6], which was also not affected by POP1 (FIG. 18e), indicating that POP1 prevents the ASC nucleation step in human macrophages, which is essential for inflammasome assembly.

POP1 Prevents NLRP3 Inflammasome Assembly in Mouse Macrophages

Figure 19A:
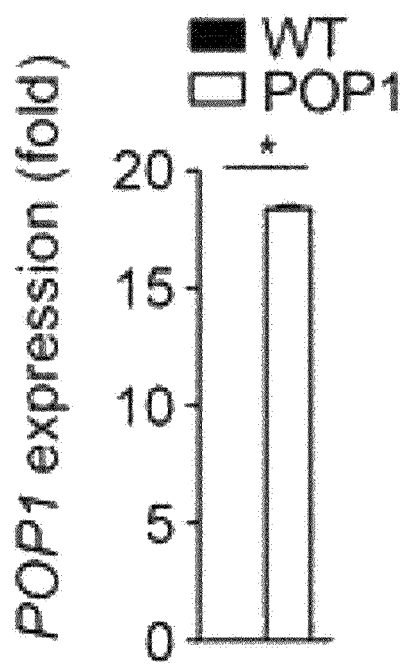
FIGS. 19a-c. POP1 is specifically expressed in peripheral blood monocytes. a, b, (a) Peripheral blood cells and (b) BMDM from WT and CD68-POP1 (POP1) transgenic mice were analysed by Real-time PCR for POP1 expression. c, Gating strategy for peripheral blood cells isolated from mice.
Figure 19B:
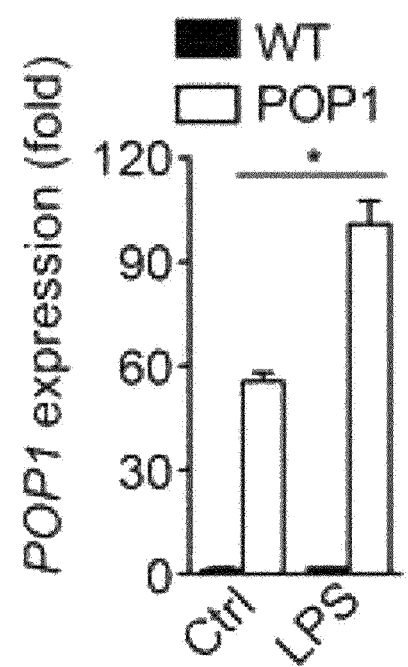
Figure 19C:
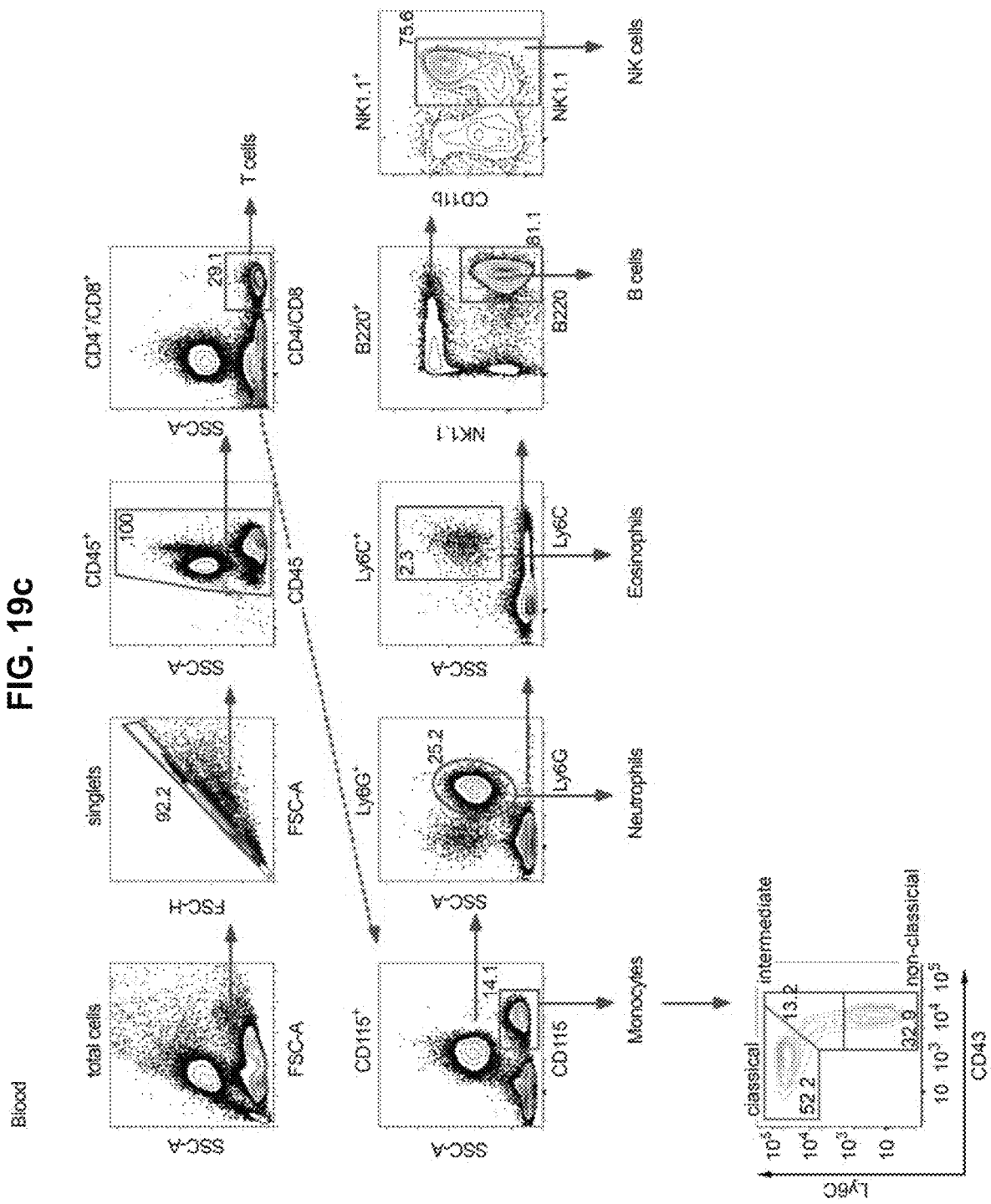
Figures 20A, 20B:
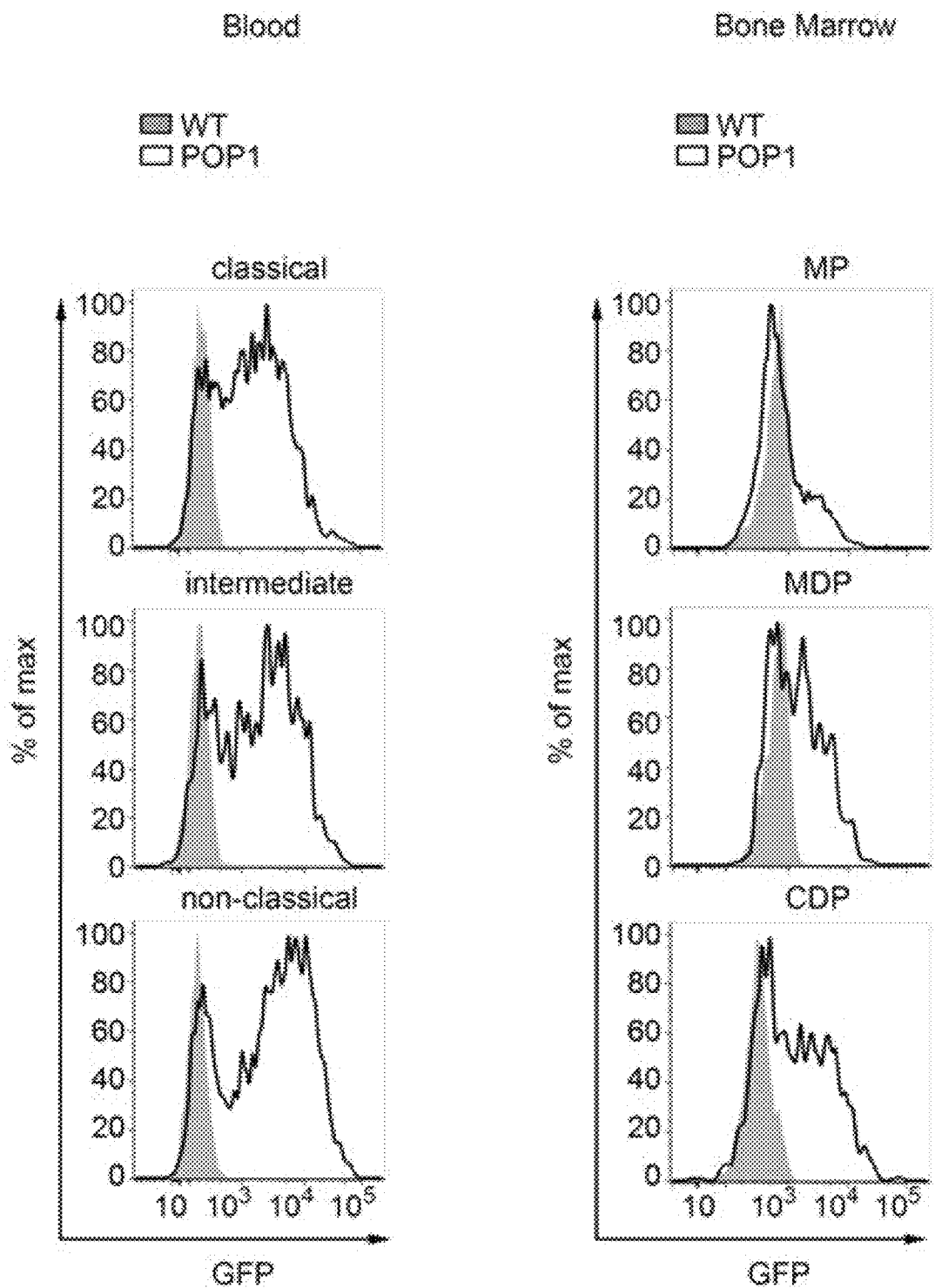
FIG. 20a-d. POP1 is specifically expressed in tissue macrophages and conventional DCs. a-d, Analysis of POP1 expression by flow cytometry in (a) different monocyte populations in peripheral blood, (b) cell populations in bone marrow, (c) peritoneal cavity and (d) spleen isolated from WT and CD68-POP1 (POP1) transgenic mice. Data are representative of three (a-d) replicates.
Figure 20C:
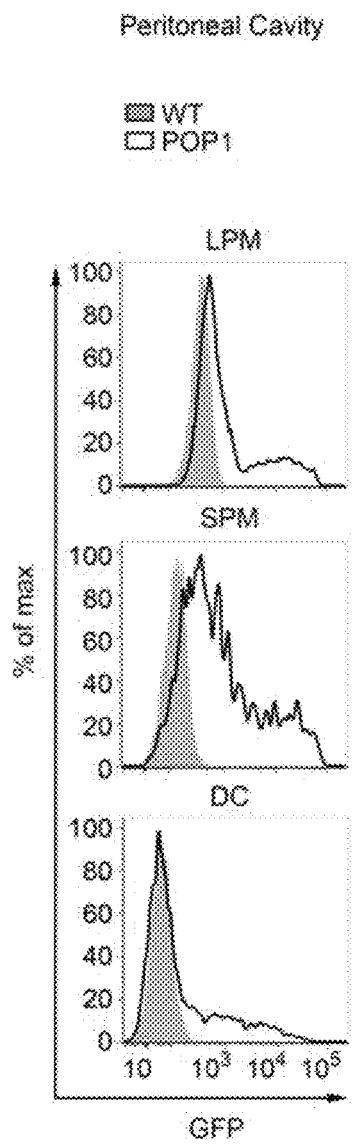
Figure 20D:
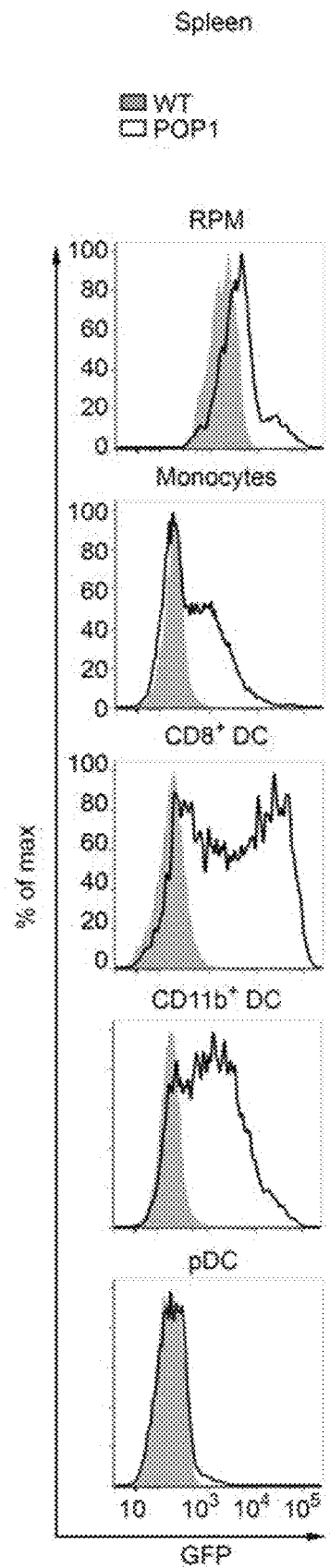
Figure 21A:
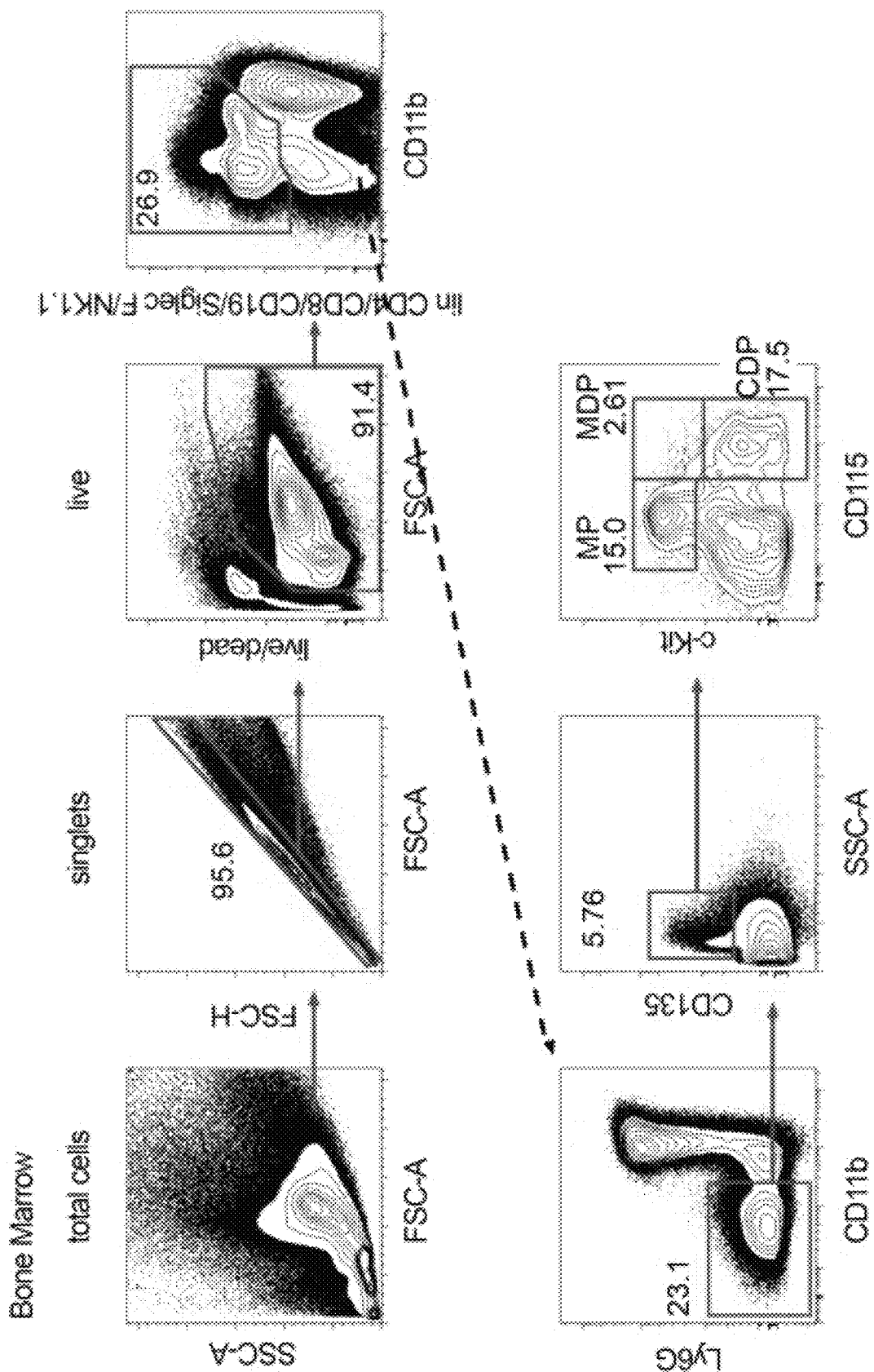
FIGS. 21a-c. Gating strategy to define cell populations expressing transgenic POP1 in a, bone marrow, b, peritoneal cavity and c, spleen. Data are representative of three (a-c) replicates.
Figure 21B:
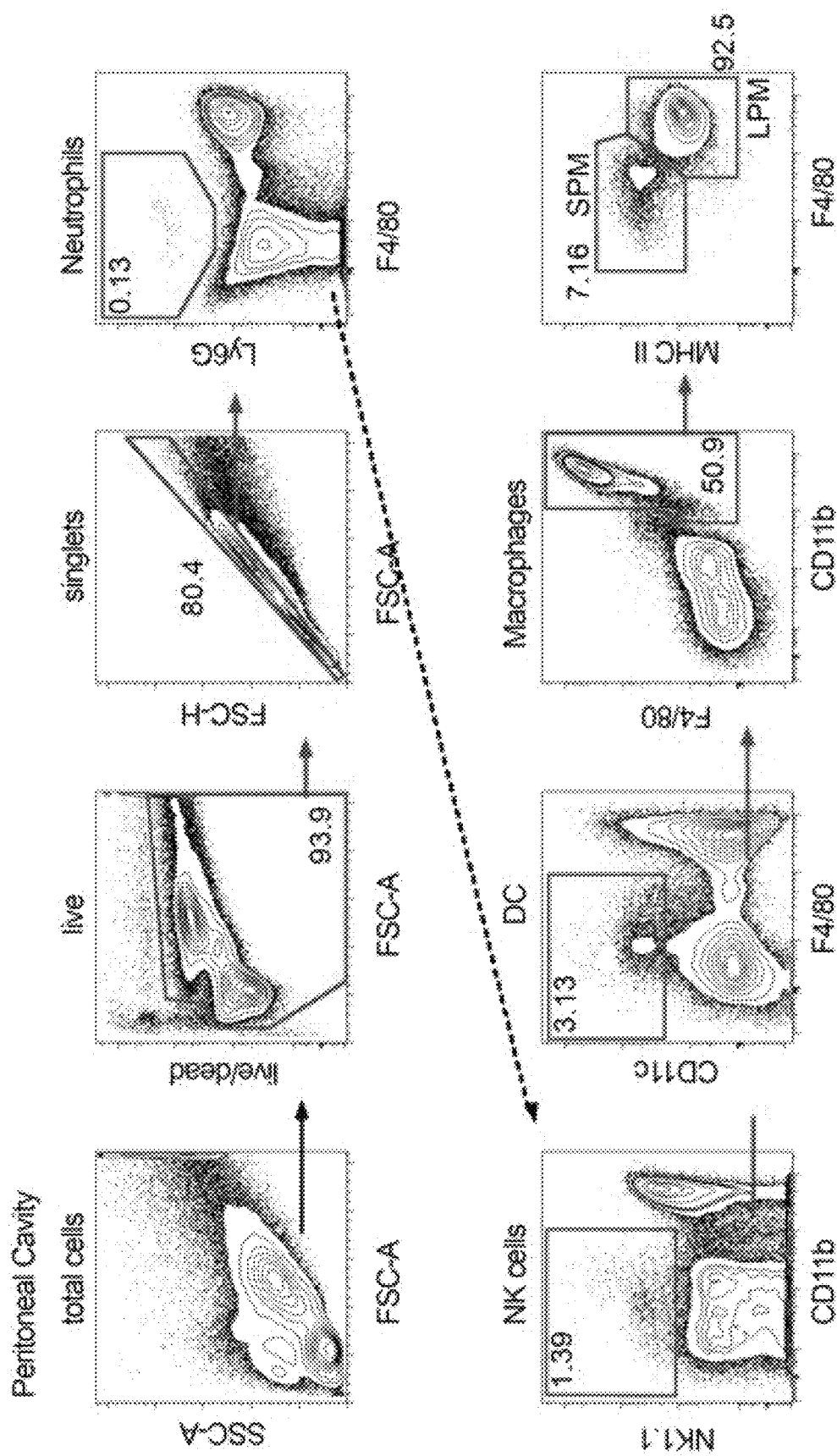
Figure 21C:
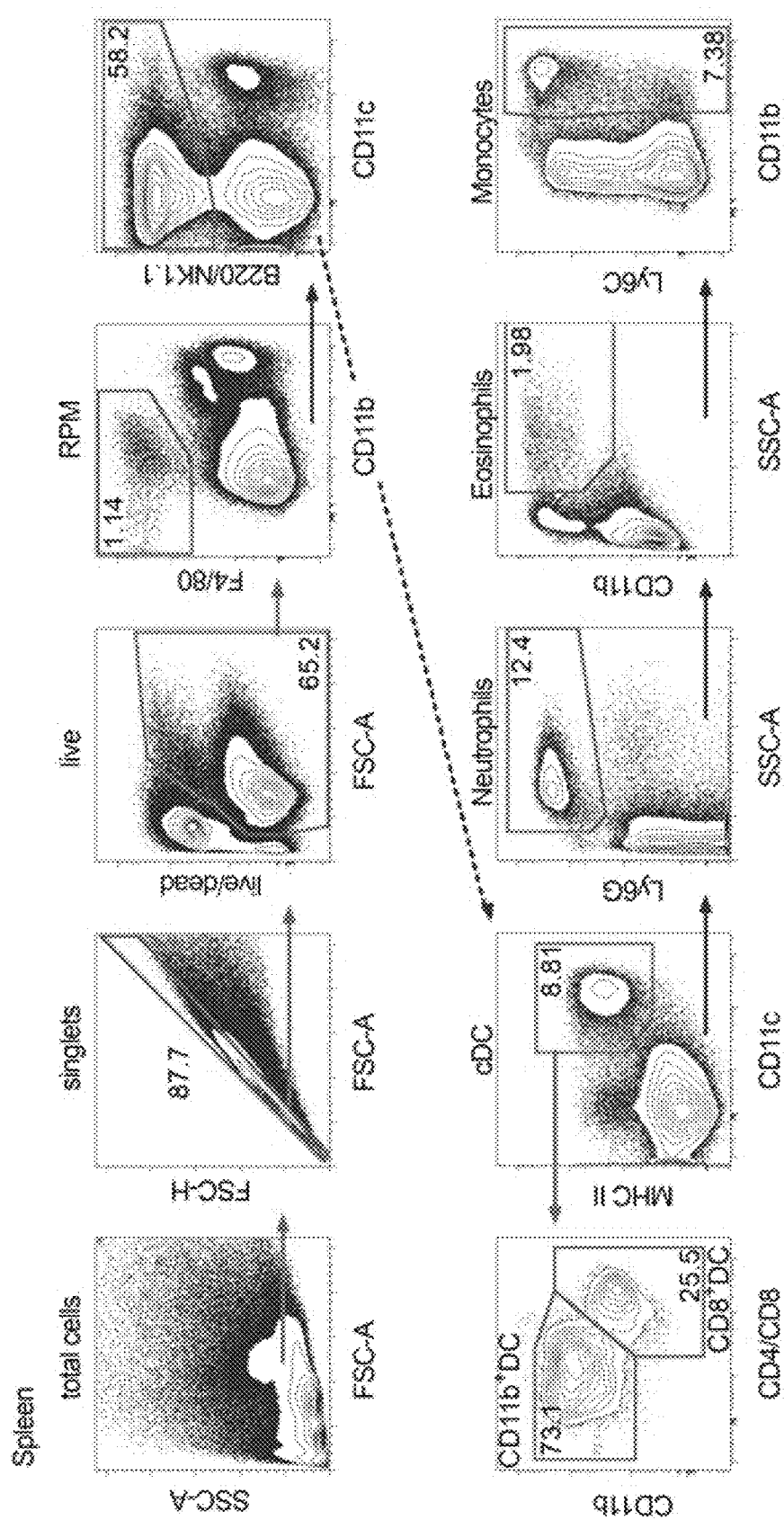
Figure 23:
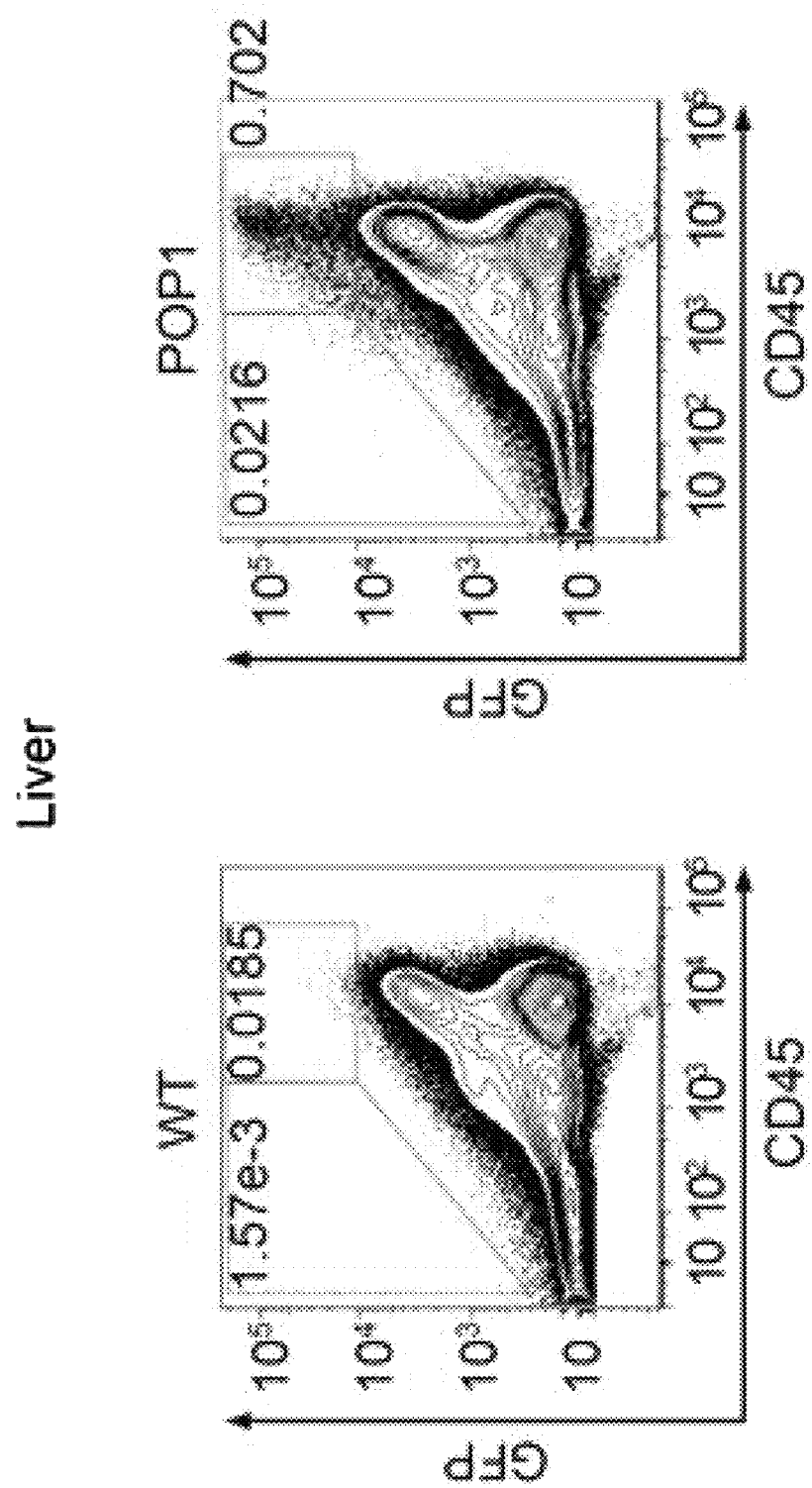
FIG. 23. POP1 is specifically expressed in CD45+ cells in CD68-POP1 transgenic mice. Analysis of POP1 expression by flow cytometry in CD45- and CD45+ cell populations in liver isolated from wilt type (WT) and CD68-POP1 (POP1) transgenic mice. Data are representative of three replicates.

Since all POPs, including POP1, are lacking from mice (Stehlik et al J Immunol 179, 7993-8 (2007); Khare et al. Nat Immunol 15, 343-353 (2014); herein incorporated by reference in their entireties), GFP-POP1 transgenic (TG) mice were generated and POP1 expression to MΦ was restricted using the hCD68/IVS-1 promoter/enhancer (Iqbal et al. Blood blood-2014-04-568691 (2014); Khare et al. Nat Immunol 15, 343-353 (2014); Gough et al. Immunology 103, 351-61 (2001); herein incorporated by reference in their entireties), based on the expression observed in CD68$^+$MΦ (FIG. 15a). qPCR analysis of whole blood cell RNA revealed expression of POP1 specifically in CD68-POP1 TG, but not in wild-type (WT) mice (FIG. 19a). POP1 expression from the CD68/IVS-1 promoter in BMDM$^{POP1}$ was LPS-inducible (FIG. 19b), thus recapitulating the inducible expression found in hMΦ (FIG. 15e, f). Flow cytometry analysis of peripheral blood demonstrated POP1 expression selectively in monocytes (FIG. 22a, FIG. 17c), with equal expression in classical Ly6C$^{hi}$CD43$^-$, intermediate Ly6C$^{int}$CD43$^+$ and non-classical Ly6C$^{lo}$CD43$^+$ monocytes (FIG. 21a). POP1 was also expressed in the myeloid-(MP), MΦ and DC-(MDP) and common DC precursor (CDP) in bone marrow (FIG. 20b, 21a), large peritoneal MΦ (LPM), small peritoneal MΦ(SPM) and peritoneal DC (FIG. 18c, 22b), as well as in splenic red pulp MΦ (RPM), monocytes and CD11b$^+$DCs, but not plasmacytoid DC (pDC) (FIG. 18d, 23c). Expression was also detected in BMDM by immunoblot (FIG. 22b). Monocyte/MΦ-specific POP1 expression was also observed in other tissues, with no detectable expression in CD45$^-$ cells (FIG. 23). Mouse and human ASC are highly homologous within the PYD (FIG. 25a), and as observed for THP-1 cells, POP1 also interacted with mouse ASC, but not NLRP3 or AIM2 in BMDM (FIG. 22c). In vivo, oligomerization of ASC requires nucleation by NLRP3 and the subsequent ASC polymerization can be captured by non-reversible cross-linking and functions as a readout for inflammasome activation (Fernandes-Alnemri et al. Cell Death Differ 14, 1590-604 (2007); herein incorporated by reference in its entirety), which was markedly reduced in LPS primed and ATP-treated BMDM$^{POP1}$ compared to BMDM$^{WT}$ (FIG. 22d). Consequently, BMDM$^{POP1}$ lacked active caspase-1 p10 and mature IL-1β in culture supernatants of LPS/ATP treated cells to a similar extent as the caspase-1 inhibitor zYVAD-fmk (FIG. 22e), and revealed reduced active caspase-1 as quantified by flow cytometry in intact cells (FIG. 22f).

POP1 Prevents Inflammasome-Dependent Cytokine Release in Mouse Macrophages

Figure 24A:
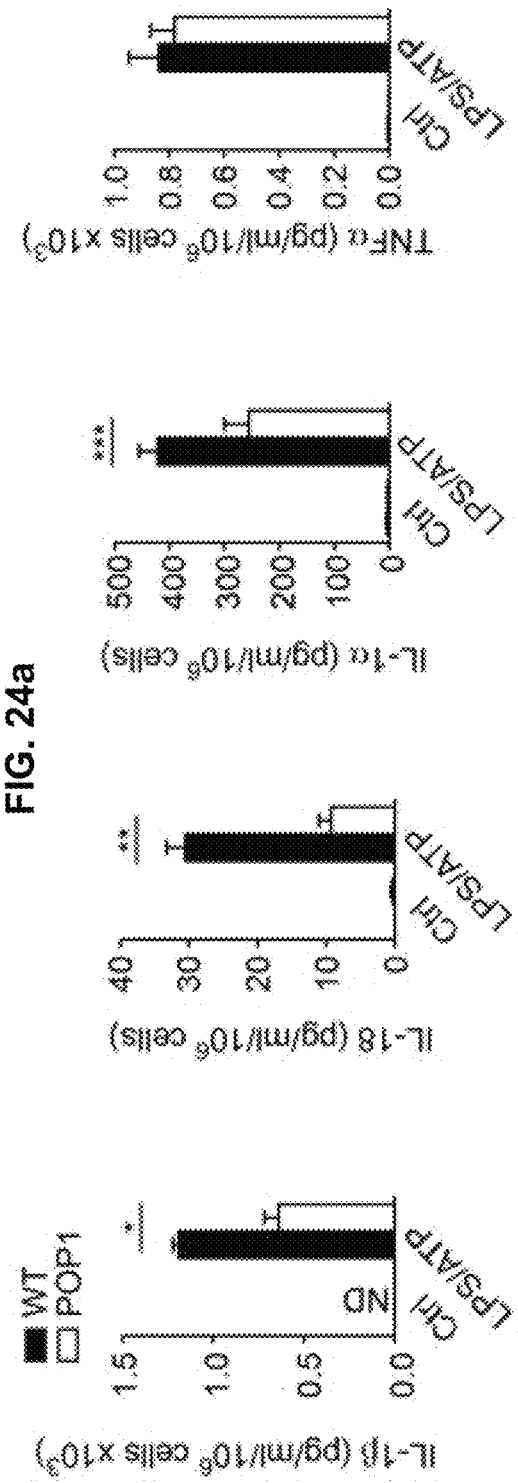
Figure 24B:
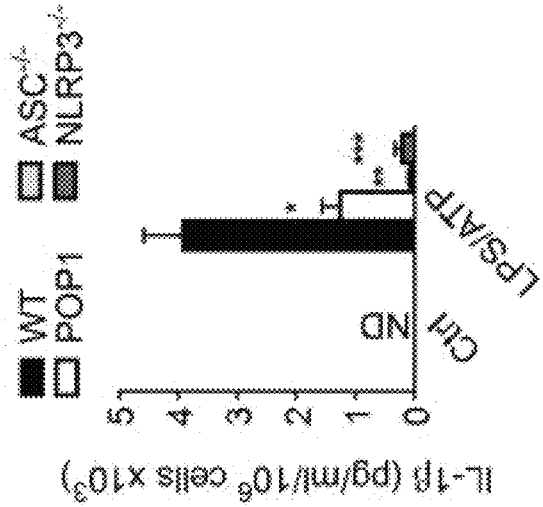

LPS/ATP treated BMDM$^{POP1}$ also displayed significantly reduced levels of IL-1β, IL-1α and IL-18 in culture supernatants by ELISA. However, secretion of TNFα, which occurs independently of caspase-1, was not affected (FIG. 24a). Significantly, reduced IL-1β release in BMDM$^{POP1}$ was comparable to BMDM$^{ASC-/-}$ and BMDM$^{NLRP3-/-}$ (FIG. 24b). K$^+$ efflux is the unifying mechanism of NLRP3 activation (Munoz-Planillo et al Immunity 38, 1142-1153 (2013); herein incorporated by reference in its entirety). Hence, culturing BMDM$^{POP1}$ in K$^+$-free medium showed impaired IL-1β release compared to BMDM$^{WT}$ (FIG. 24c). Similarly, peritoneal macrophages (PM$^{POP1}$) showed impaired IL-1β release in response to agonists for NLRP3 and other ASC-dependent inflammasomes, including poly (dA:dT) (activating AIM2) and flagellin (activating NLRC4) (FIG. 24d). BMDM' also showed reduced LDH release, and thus pyroptosis, when compared to BMDM$^{WT}$ in response to NLRP3 activation (FIG. 24e), but did not reveal any altered LPS-induced activation of NF-κB, p38, JNK or ERK (FIG. 25b), or altered transcription of Il1b and Il18 (FIG. 25c), ruling out POP1 effects on inflammasome priming, as observed in human macrophages. Collectively, these data indicate that POP1 impairs assembly of the NLRP3 inflammasome in macrophages, by impairing the NLRP3'-mediated nucleation of ASC and consequently, release of inflammasome-dependent cytokines.

Figure 27A:
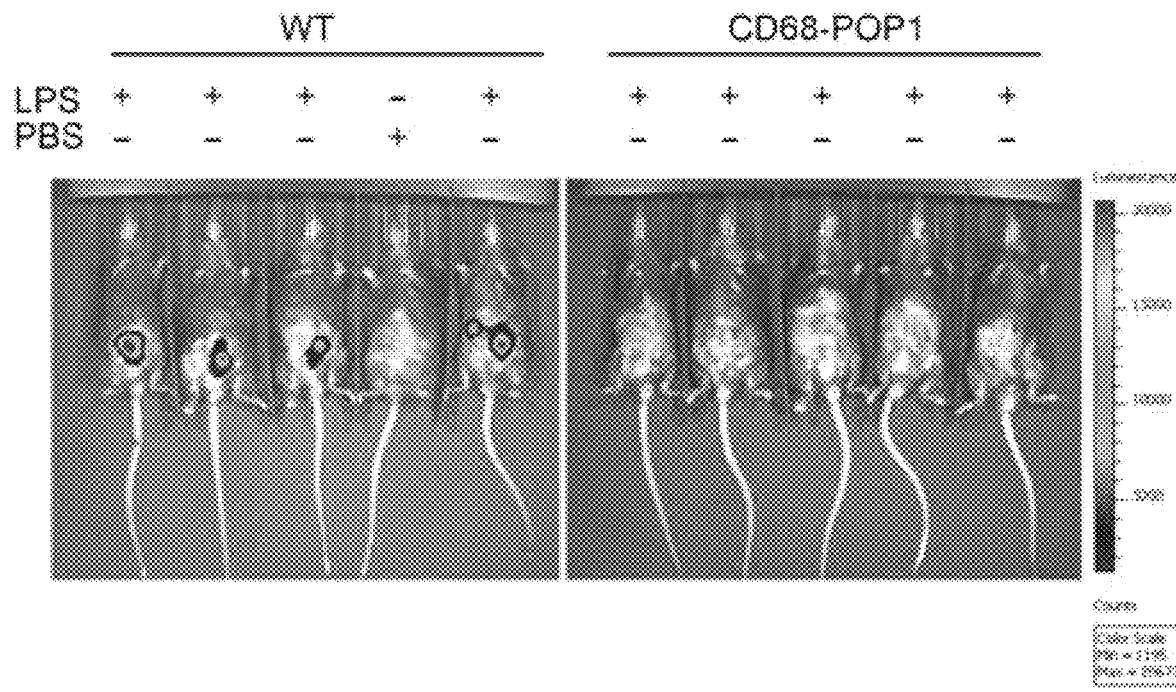
FIGS. 27a-f. Reduced LPS and ASC particle-induced neutrophil infiltration in CD68-POP1 transgenic mice. a, In vivo image of MPO activity in mice 3 h after i.p. injection of PBS or *E. coli* LPS (2.5 mg/kg body weight) in wild-type (WT) and CD68-POP1 transgenic mice. The range of the luminescence signal is from 1195 to 20677 photons/sec/cm2/sr. b, FACS purification of ASC-GFP particles from stable ASC-GFP expressing HEK293 cells and of ASC-GFP/RFP-POP1 particles from transiently transfected HEK293 cells. c, In vivo imaging as above in WT and CD68-POP1 mice 4 h after i.p. injection of PBS or 1×105 FACS-purified ASC-GFP particles. The range of the luminescence radiance is from 206 to 1080 photons/sec/cm2/sr. d, Coomassie staining of purified TAT-GFP and TAT-POP1. e, Uptake of TAT-GFP by CD45+CD11b+ peritoneal lavage cells after 1 h of i.p. TAT-GFP injection. (n=5). f, Mice were i.p. injected with TAT-GFP and TAT-POP1 (40 μg/kg), followed by LPS injection (2.5 mg/kg) 30 min. later and in vivo image of MPO activity 1 h after LPS injection. The range of the luminescence radiance is 860 to 5814 photons/sec/cm2/sr.

Monocyte/Macrophage-Specific Expression of POP1 Ameliorates LPS-Induced Peritonitis and Mouse CAPS in CD68-POP1 Transgenic Mice Caspase-11 is responsible for LPS- and Gram negative bacteria-induced lethal shock, but ASC and NLRP3 are both necessary for amplifying this lethal response to LPS in vivo (Kayagaki et al. Nature 479, 117-21 (2011); herein incorporated by reference in its entirety). Accordingly, Asc$^{-/-}$ and Nlrp3$^{-/-}$ mice are protected from LPS-induced lethality in response to moderate LPS doses (Kayagaki et al. Nature 479, 117-21 (2011); Mariathasan et al. Nature 440, 228-232 (2006); Mariathasan et al. Nature 430, 213-8 (2004); herein incorporated by reference in their entireties). Experiments were conducted to determine whether POP1 also modulates NLRP3 activity in vivo. As NLRP3 inflammasome-released IL-1β is essential for neutrophil recruitment during sterile inflammation (McDonald et al. Science 330, 362-366 (2010); herein incorporated by reference in its entirety), WT and CD68-POP1 TG mice we injected i.p. with a low dose of LPS and determined neutrophil infiltration 3 hours after LPS challenge by quantifying myeloperoxidase (MPO) activity in vivo. Contrary to PBS, injection of LPS recruited a substantial number of neutrophils into the peritoneal cavity, which was completely abolished in CD68-POP1 TG mice (FIG. 26a, FIG. 27a). Consequently, CD68-POP1 TG mice experienced significantly less hypothermia (FIG. 26b) and were significantly more protected from a lethal LPS dose (FIG. 26c). Compared to 100% lethality in WT mice, only 30% of CD68-POP1 TG mice died within 96 hours, which is similar to ASC$^{-/-}$ mice (Mariathasan et al. Nature 430, 213-8 (2004); herein incorporated by reference in its entirety). Consistent with reduced neutrophil infiltration and increased survival, serum IL-1β and IL-18 levels were also reduced, but TNFα levels remained unchanged (FIG. 26d). CAPS can be recapitulated in mice by knocking-in CAPS-associated NLRP3 mutations (Brydges et al. Immunity 30, 875-87 (2009); Meng et al. Immunity 30, 860-74 (2009); Brydges et al. J Clin Invest 123, 4695-4705 (2013); herein incorporated by reference in their entireties). A mouse model for Muckle Wells Syndrome (MWS) was employed, where floxed NLRP3$^{A350V}$, corresponding to human NLRP3$^{A352V}$, is expressed exclusively in myeloid cells in the presence of lysozyme M-Cre (CreL) (Brydges et al. Immunity 30, 875-87 (2009); Brydges et al. J Clin Invest 123, 4695-4705 (2013); herein incorporated by reference in their entireties). NLRP3$^{A350V/+}$ CreL mice develop systemic inflammation affecting multiple organs, display characteristic skin inflammation and die within two weeks of birth, a phenotype caused by excessive IL-1β and IL-18 release and pyroptosis. NLRP3$^{A350V/+}$ CreL mice had inflammatory skin abscesses and lesions shortly after birth, which developed into scaling erythema, but NLRP3$^{A350V1+}$ CreL CD68-POP1 mice did not display this phenotype (FIG. 26e). Histological analysis revealed that POP1 expression prevented leukocytic infiltrates in multiple organs, including the liver and the skin and also restored skin architecture (FIG. 26f), and reduced systemic IL-1β levels (FIG. 26g). Significantly, POP1 expression restored the severely delayed growth (FIG. 26h)

and prevented mortality of NLRP3$^{A350V/+}$ CreL mice from multi-system organ failure (FIG. 26i). Overall, these findings further indicate that POP1 acts on ASC to inhibit the NLRP3 inflammasome and thereby blocks the secretion of the pro-inflammatory cytokines IL-1β and IL-18, thereby ameliorating systemic inflammation and lethality in vivo.

Figure 27C:
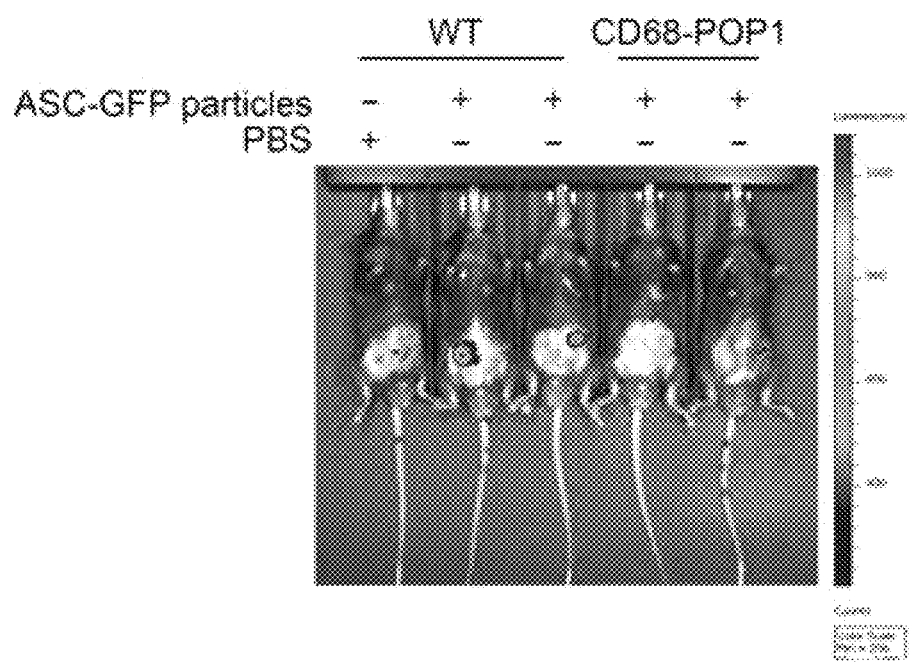
Figure 27B:
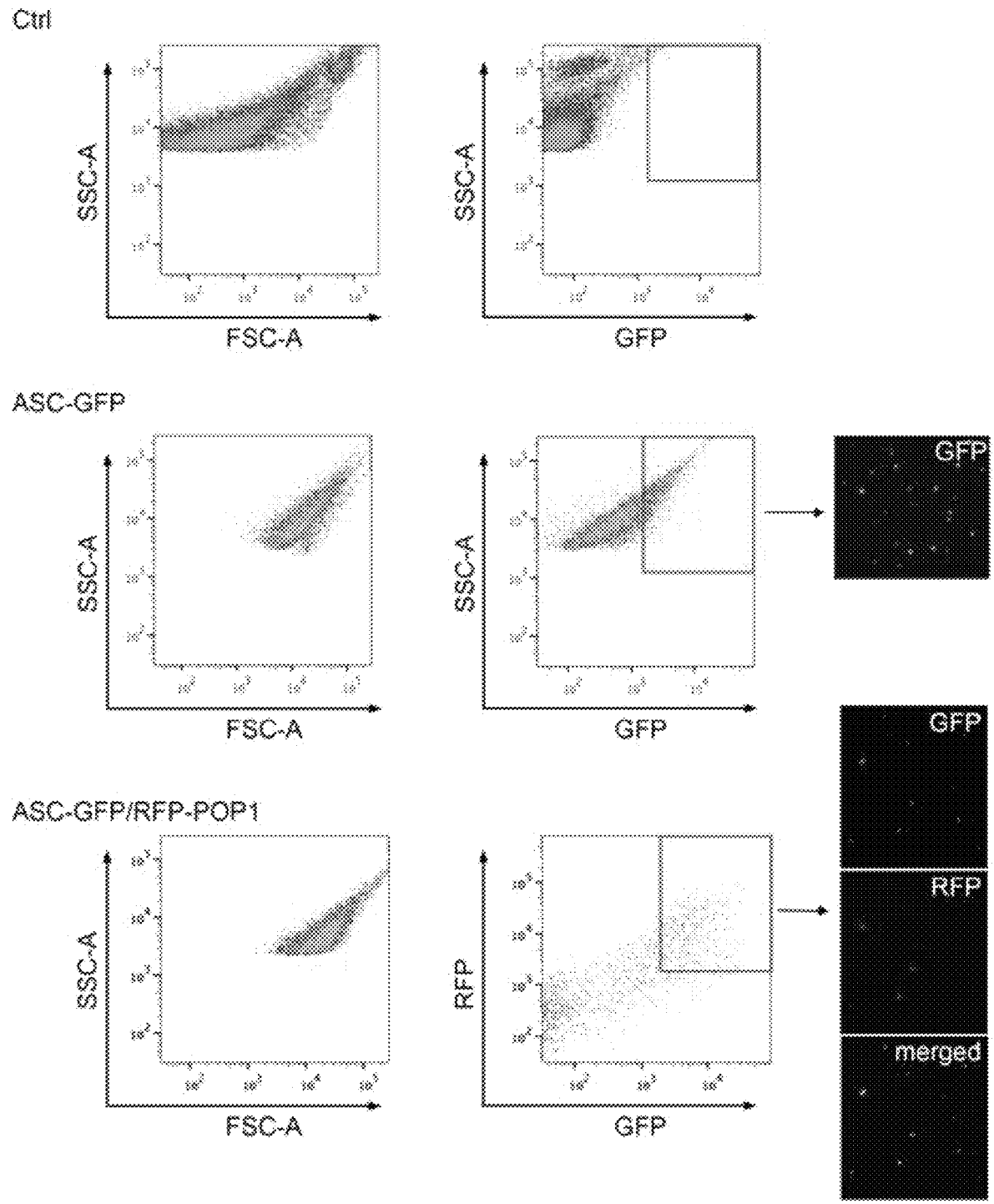
Figure 27F:
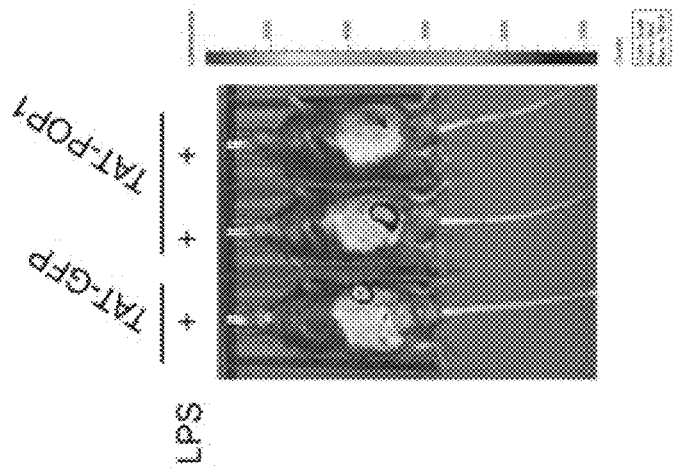
Figure 27E:
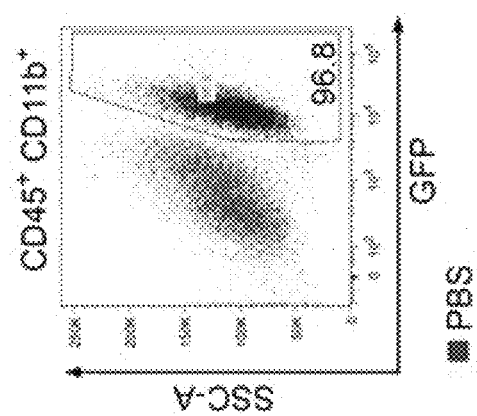
Figure 27D:
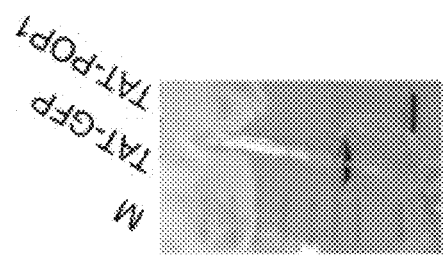
Figure 28A:
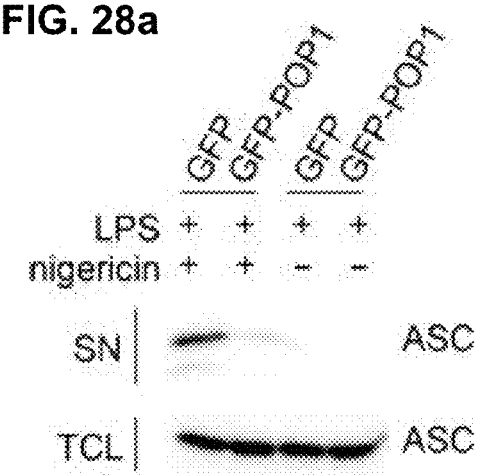
FIGS. 28a-h. Expression of POP1 prevents ASC particle release and ameliorates ASC particle-induced inflammatory disease. a, b LPS primed (a) THP-1 cells expressing GFP or GFP-POP1 were treated with nigericin and (b) WT and POP1 BMDM were treated with ATP and released ASC determined by immunoblot in total cell lysates (TCL) and culture supernatants (SN). c, as in (a), but SN were cross linked before analysis. d, ASC-GFP particles were FACS purified and imaged by immunofluorescence microscopy, showing the characteristic filamentous structure. Scale bar is 2 μm. Culture supernatants from THP-1 cells stably expressing GFP or GFP-POP1 were analysed for IL-1β release by ELISA in LPS primed cells before (Ctrl) and after treatment with 1×103 FACS-purified ASC-GFP particles. e, Mixed ASC-GFP/RFP-POP1 particles were FACS purified as above, showing identical structure. Scale bar is 2 μm. Culture supernatants from THP-1 cells were analysed for IL-1β release by ELISA in LPS primed cells before (Ctrl) and after treatment with 1×10³ FACS-purified ASC-GFP and ASC-GFP/RFP-POP1 particles. f, Representative in vivo image of MPO activity in WT and CD68-POP1 TG mice 4 h after i.p. injection of PBS or 1×10⁵ FACS-purified ASC-GFP particles, and quantification (n=2/genotype). The range of the luminescence radiance is 206 to 1080 photons/sec/cm2/sr. g, ELISA of total IL-1β in the peritoneal cavity in above mice 4 h after i.p. ASC-GFP particle challenge. h, Mice were i.p. injected with TAT-GFP and TAT-POP1 (40 μg/kg), followed by LPS injection (2.5 mg/kg) 30 min later and in vivo image of MPO activity 1 h after LPS injection. The range of the luminescence radiance is 2500 to 12500 photons/sec/cm2/sr.
Figure 28B:
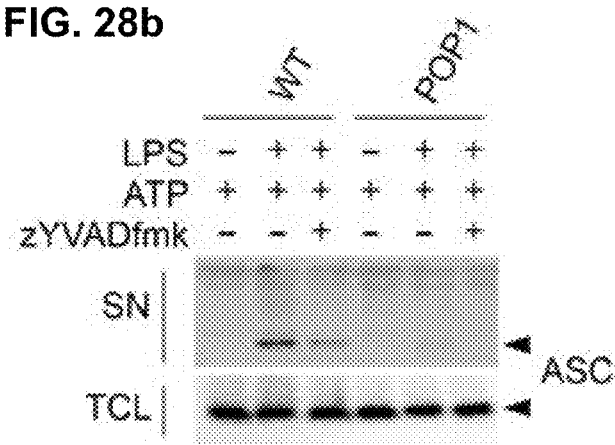
Figure 28C:
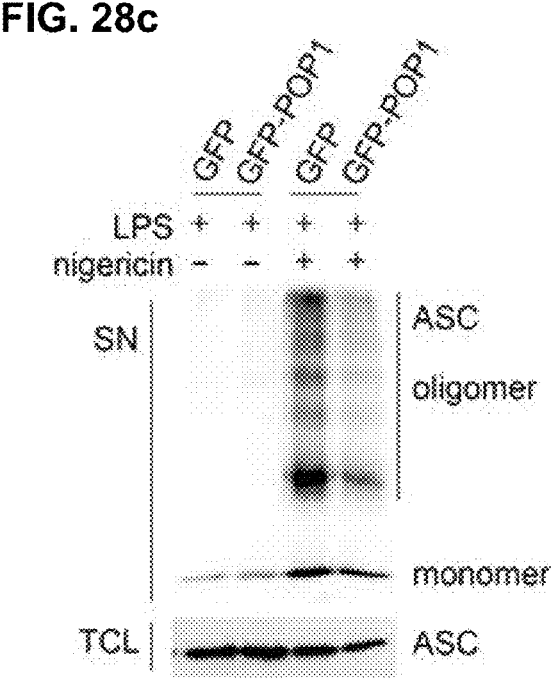
Figure 28D:
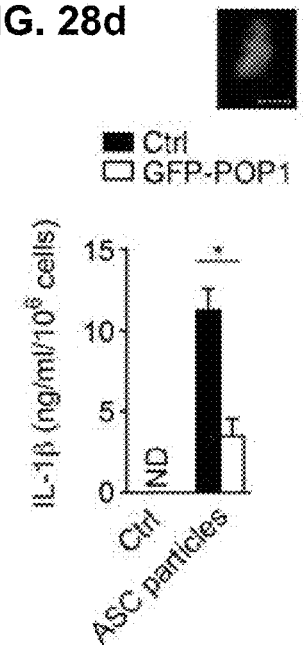
Figure 28E:
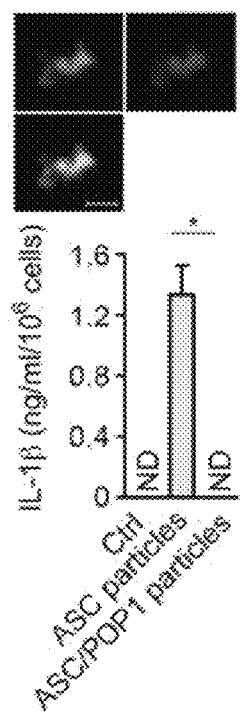
Figure 28H:
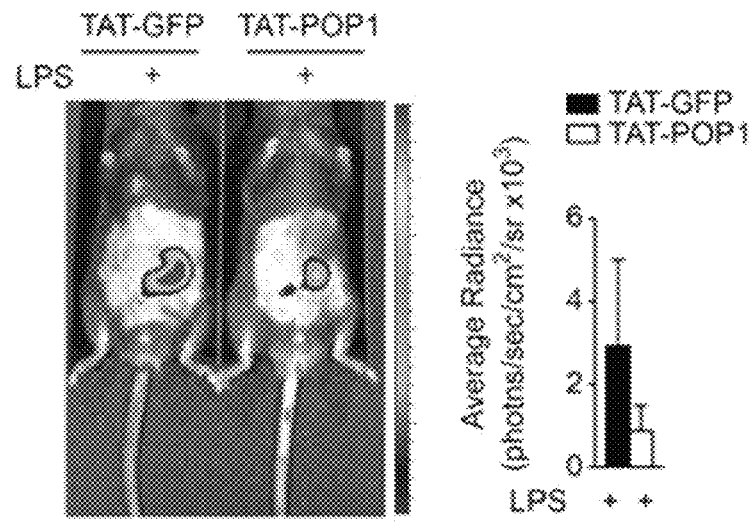
Figure 28F:
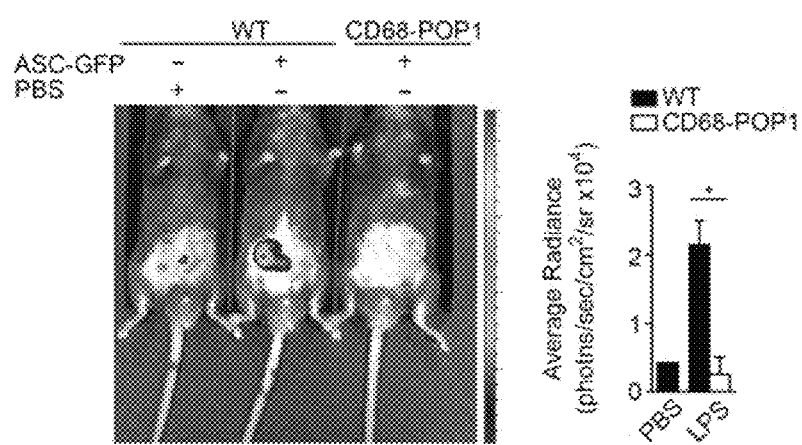
Figure 28G:
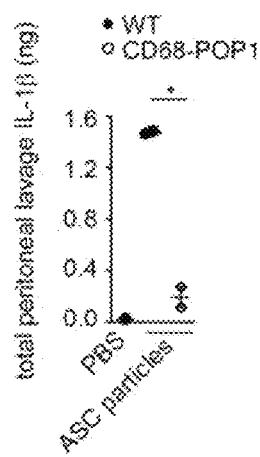
Figure 29:
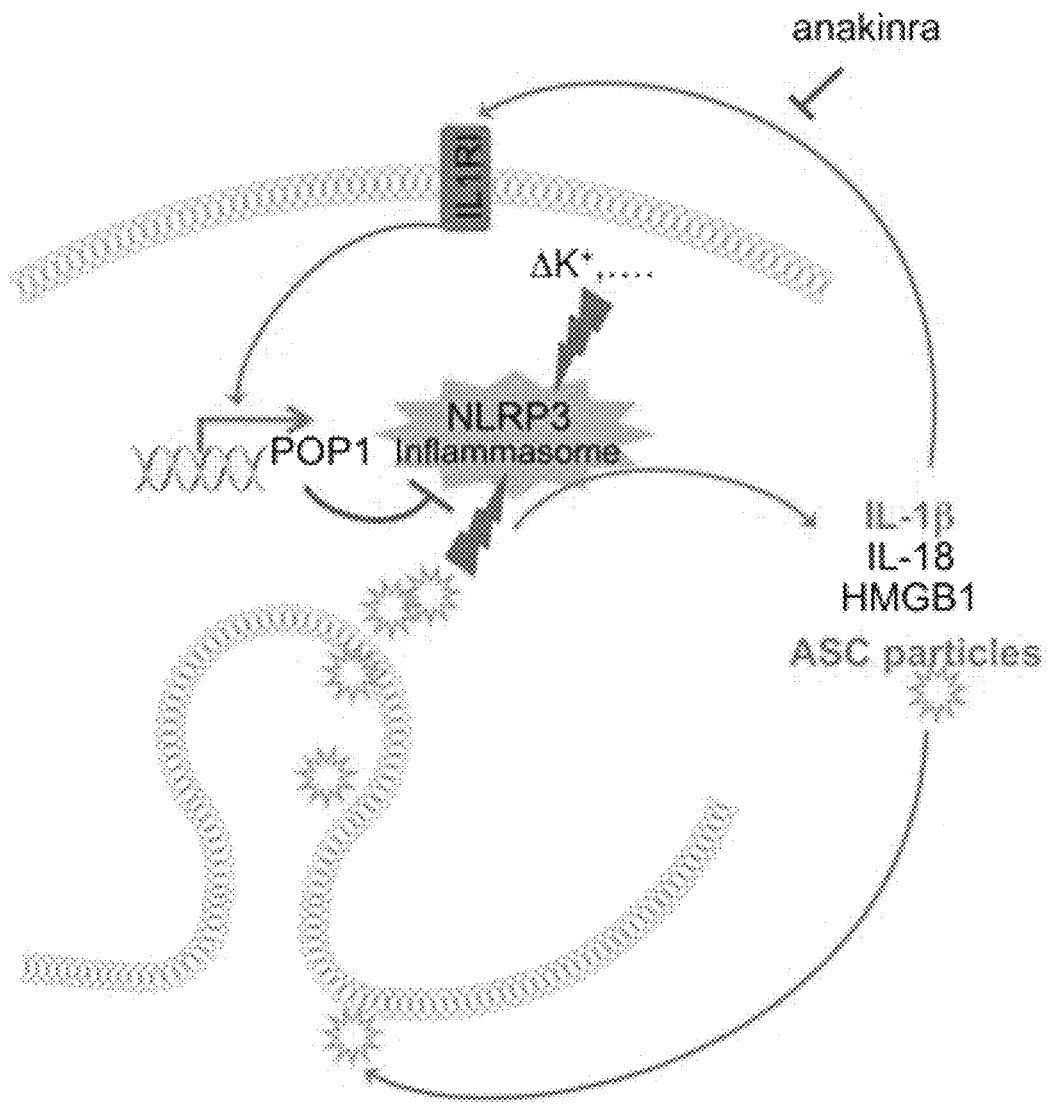
FIG. 29. Proposed function of POP1 as an IL-1β-regulated NLRP3 inflammasome regulator. NLRP3 activation causes inflammasome assembly and the release of pro-inflammatory mediators, including IL-1 (3, which in turn triggers autocrine and paracrine signals that promote POP1 expression as a late response gene. Subsequently, POP1 functions as an inhibitor for NLRP3 inflammasome assembly. Pyroptosis also releases oligomeric ASC particles, which act as danger signals upon phagocytosis and trigger NLRP3-independent nucleation of soluble ASC and inflammasome assembly. POP1 also prevents the release of ASC particles by preventing NLRP3 inflammasome nucleation.

Expression of POP1 Prevents ASC Particle Release and Ameliorates ASC Particle-Induced Inflammation in CD68-POP1 Transgenic Mice Polymerized ASC particles have been detected in the serum of active CAPS patients (Baroja-Mazo et al. Nat Immunol 15, 738-48 (2014); herein incorporated by reference in its entirety), which are released from macrophages through inflammasome-dependent pyroptosis and act as danger signals on neighbouring cells (Franklin et al. Nat Immunol 15, 727-37 (2014); Baroja-Mazo et al. Nat Immunol 15, 738-48 (2014); herein incorporated by reference in their entireties). POP1 prevented ASC nucleation (FIG. 17k, l), the subsequent ASC polymerization (FIG. 22d), caspase-1 activation (FIG. 17d, 22e, 22f) and pyroptosis (FIG. 17e, 25e). Consistently, culture supernatants from LPS primed and nigericin or ATP-treated control THP-1GFP cells and BMDM$^{WT}$ contained ASC, but supernatants from THP-1$^{GFP-POP1}$ cells (FIG. 28a) or BMDM$^{POP1}$ (FIG. 28b) did not contain any ASC. Particularly, the release of polymeric ASC was inhibited by POP1 (FIG. 28c). Extracellular ASC particles are phagocytized by macrophages and directly nucleate soluble ASC to activate caspase-1 in an ASC-dependent, but NLRP3-independent process (Franklin et al. Nat Immunol 15, 727-37 (2014); herein incorporated by reference in its entirety). FACS-purified ASC-GFP particles (FIG. 28d, FIG. 27b) induced IL-1β release in LPS primed THP-1$^{GFP}$ cells, but not in THP-1$^{GFP-POP1}$ cells (FIG. 28d), suggesting that POP1 incorporates into newly polymerized ASC$^{PYD}$ filaments, as suggested above (FIG. 18d, e). Subsequently, the ASCCARD density is reduced to a level that is insufficient to nucleate caspase-1 and caspase-1 activation is prevented[6]. To directly proof that POP1 incorporation into ASC particles renders them inactive, mixed ASC-GFP/RFP-POP1 particles were generated (FIG. 28e, FIG. 27b), which, contrary to ASC-GFP particles, failed to cause IL-1β release in THP-1 cells (FIG. 28e). Injection (i.p.) of ASC-GFP particles into WT mice resulted in neutrophil recruitment (FIG. 28f, FIG. 27c) and IL-1β release (FIG. 28g), which was substantially reduced in CD68-POP1 TG mice. Cell penetrating peptides are frequently employed for the delivery of molecules targeting intracellular signalling pathways (Schwarze et al. Science 285, 1569-72 (1999); herein incorporated by reference in its entirety); therefore, recombinant POP1 and GFP were produced as a control fused to the cell penetrating HIV TAT sequence (TAT-POP1 and TAT-GFP) (FIG. 27d). TAT-GFP was efficiently taken-up by peritoneal macrophages after i.p. injection in vivo (FIG. 27e), and injection of TAT-POP1, but not TAT-GFP, ameliorated LPS-induced peritonitis (FIG. 28h, FIG. 27f), reminiscent to transgenic POP1 expression. Thus, POP1 also blocks the release of ASC danger particles and consequently, propagation of secondary inflammasome responses in neighbouring cells.

Example 3

Figure 30A:
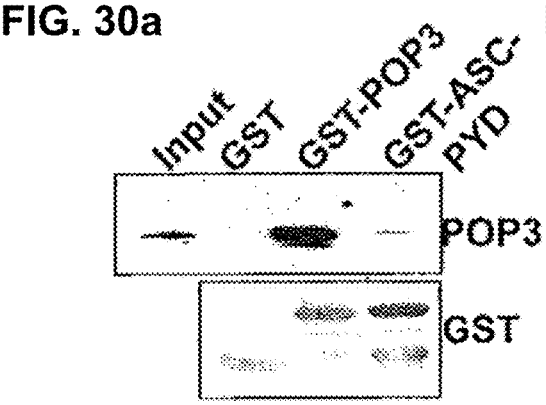
FIGS. 30a-b. POP3 interacts with ASC. (A) POP3-ASC-PYD interaction by GST pull down and (B) co-immunoprecipitation in HEK293 cells.
Figure 30B:
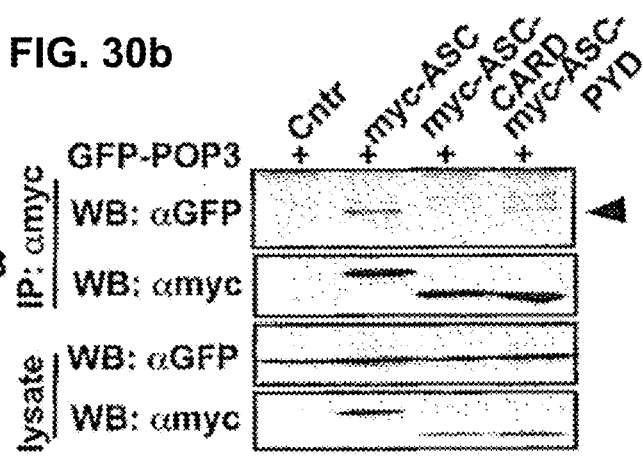

FIG. 30 shows that POP3 can interact with itself and ASC (with the PYRIN domain[PYD] of ASC) in vitro (left) and in vivo (right).

Figure 31A:
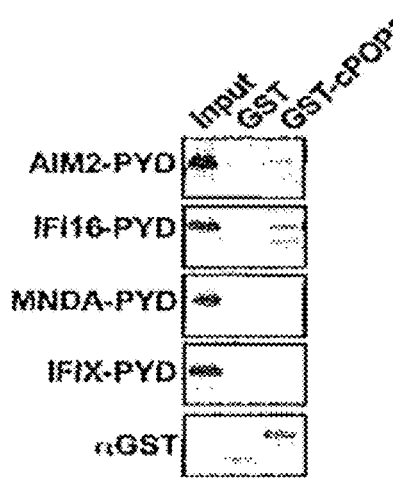
FIGS. 31a-b. POP3 interacts with ALRs. (A) GST-pull down of POP3 and the PYDs of ALRs (B) co-immunoprecipitation in HEK293 cells between POP3 and myc-tagged ALRs (IFI16 andAIM2), and self-inter-action of POP3 as control.
Figure 31B:
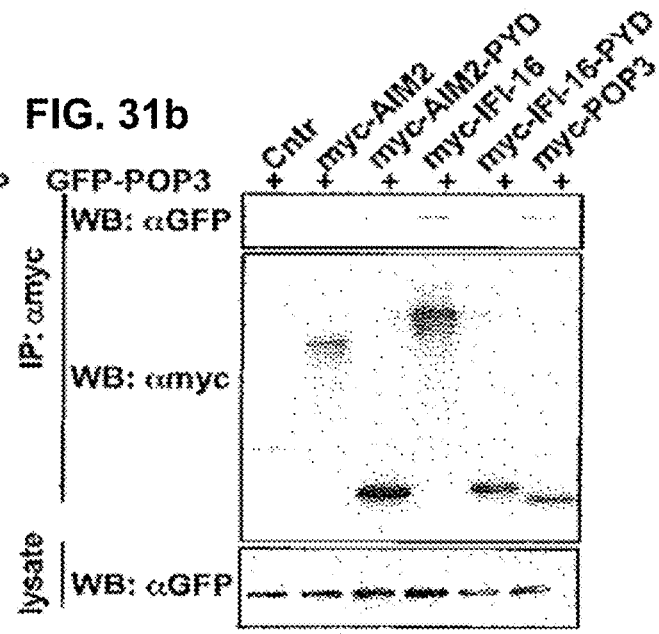

FIG. 31 shows that POP3 can interact with the PYDs of the ALRs AIM2 and IFI16 in vitro (left) and in vivo (right).

Figure 32:
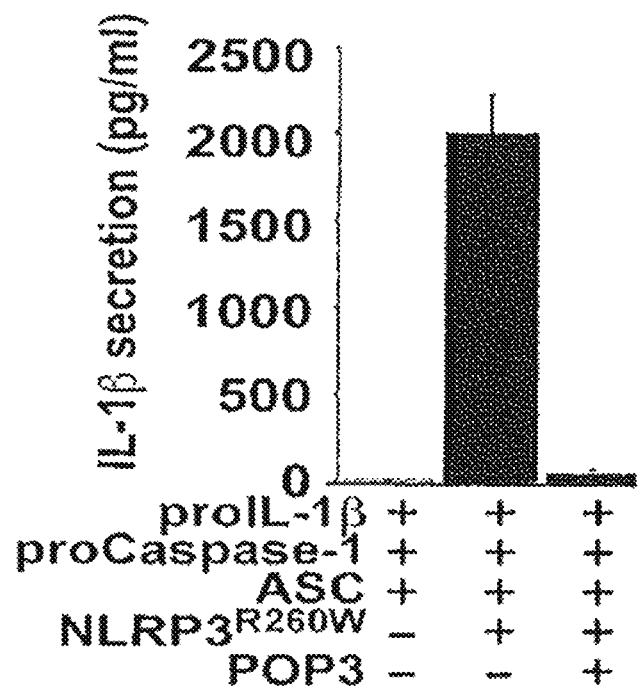
FIG. 32. NLRP3 inflammasome inhibition by POP3 in the inflammasome reconstitution system (pg/ml, mean SD; n=3).

FIG. 32 shows that POP3 can inhibit mutant NLRP3-mediated inflammasome activation in the inflammasome reconstitution system.

Figure 33:
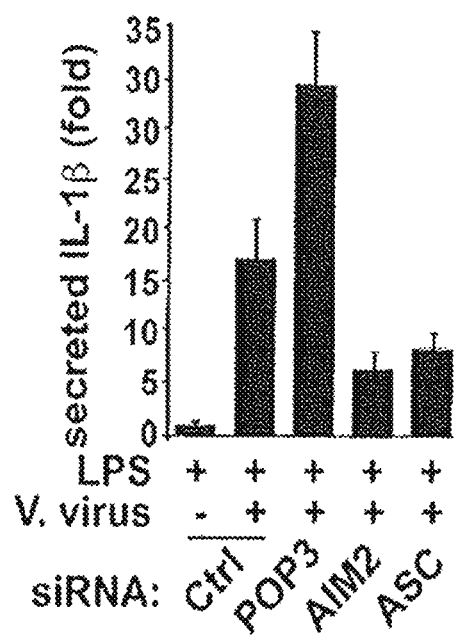
FIG. 33. Knock-down of POP3 enhances IL-1β in hMΦ. hMΦ were transfected with siRNAs primed with ultrapure LPS (10 ng/ml) and infected with vaccinia virus. IL-1β in culture SN was analyzed 12 hrs post infection.

FIG. 33 shows that knock-down of POP3 in primary human macrophages enhances vaccinia virus-mediated inflammasome activation and subsequent IL-1β release, which is inhibited by knock-down of AIM2 and ASC, which are both involved in sensing vaccinia virus infection.

FIG. 34 shows that POP3 is regulated through protein stability and is degraded by the proteasome, which is blocked by MG132, a proteasome inhibitor. Also interferon causes stability of POP3 through its posttranslational modification.

FIG. 35 shows that POP3 expression recruits IFI16 from the nucleus to the cytosol, where both proteins co-localize, which supports that both proteins can interact.

Figure 36:
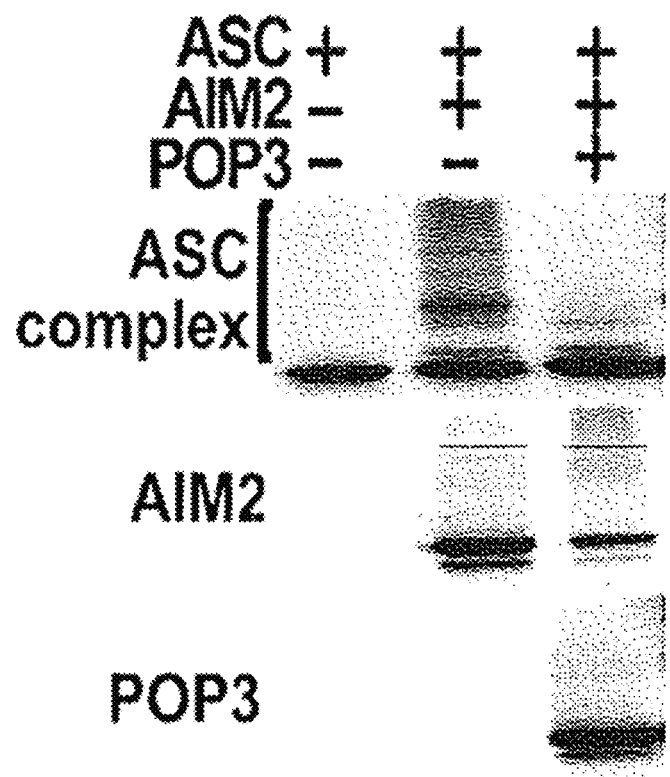
FIG. 36. HEK293 cells were transfected, non-reversibly crosslinked and analyzed by immunoblot.

FIG. 36 shows that POP3 expression prevents the interaction between AIM2 and the inflammasome adaptor ASC. AIM2 and ASC form oligomeric complexes in the absence of POP3.

Figure 37:
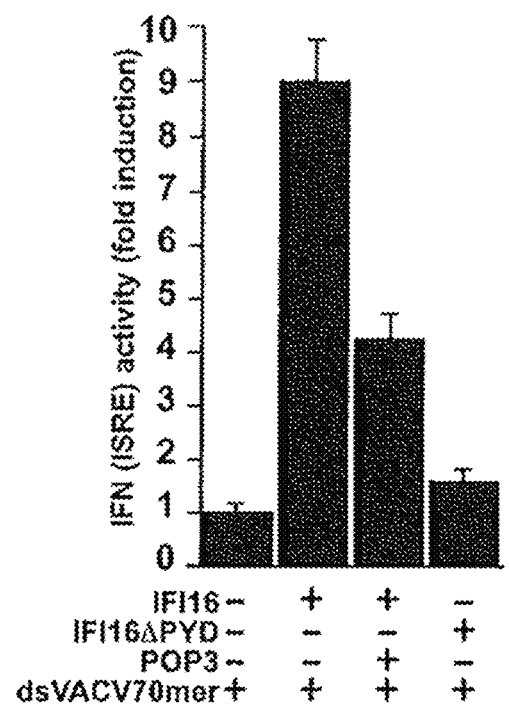
FIG. 37. HEK293 cells, which are deficient in IFI16, were transfected in the presence pRL-TK and pISRE-Luc and transfected 24 hrs later with dsVACV70mer to induce IFI16, and was analyzed by dual luciferase assay (n-=3).

FIG. 37 shows that POP3 expression blocks DNA (dsVACV70mer)-induced and IFI16 mediated activation of interferon response elements.

Figure 38A:
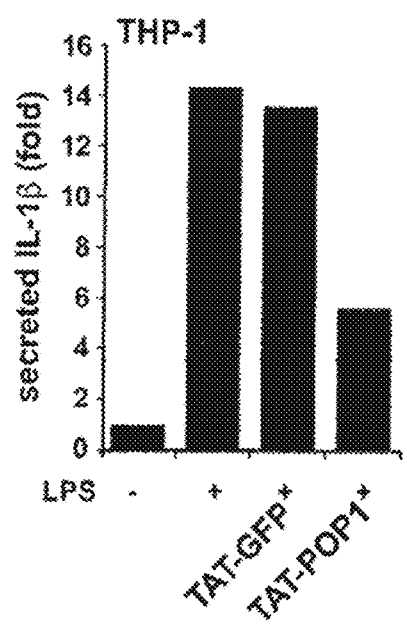
FIGS. 38a-b. Purification and delivery of recombinant TAT-POPs into human and mouse macrophages to impair inflammasome activity. Purified recombinant TAT-POP1, TAT-POP2, TAT-POP3, and TAT-GFP was delivered into human THP-1 and mouse-J774A1 macrophages, followed by activation with LPS. Released mature IL-1β was determined by ELISA. (A) Human THP-1 macrophages were incubated with TAT-GFP control or TAT-POP1 for 20 minutes, followed by treatment with LPS (300 ng/ml) for 16 hours to activate inflammasomes. (B) J774A1 cells were incubated with TATGFP control, TAT-POP1, TAT-POP2, or TAT-POP3 (black and grey bars represent a low and a higher TAT-peptide concentration, respectively) for 20 minutes, followed by treatment with LPS (300 ng/ml) for 16 hours to activate inflammasomes, followed by incubation with ATP (5 mM) for 30 minutes to induce release of mature IL-1β and incubation in fresh medium for 3 hours (ATP is required for mouse macrophages to release processed IL-1β). Release of IL-1β was assessed in culture supernatants by ELISA (BD Siosciences) and represented as fold induction compared to uninduced control cells. One representative experiment is shown. The relatively modest inhibition (~35-50%) is likely due to the preliminary experimental setting, where buffer conditions, peptide concentration, time of delivery and timing of the inflammasome activation following peptide delivery were not optimized, but clearly demonstrates the potential of a POP peptide-based approach to inhibit inflammasome activity.
Figure 38B:
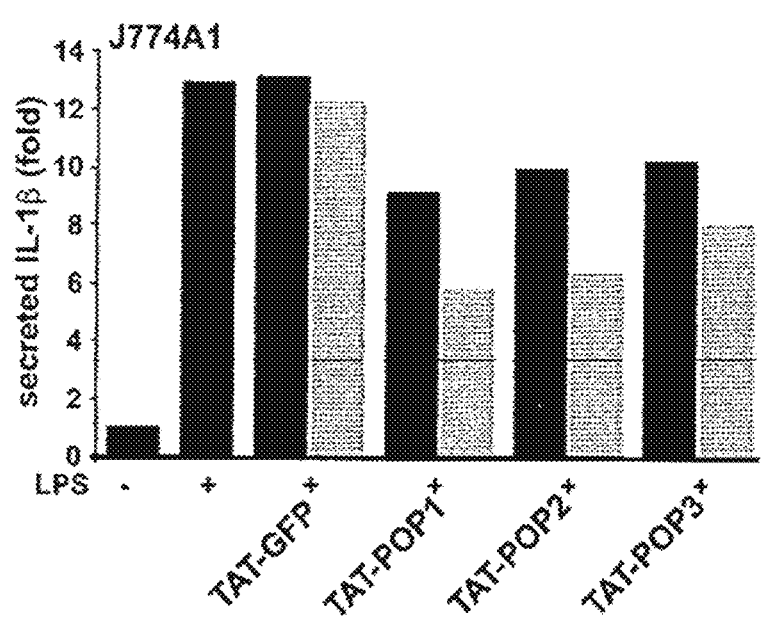

FIG. 38 shows that delivery of recombinant POPs fused to the cell permeable TAT peptide into macrophages can block inflammasome activity.

All publications and patents provided herein incorporated by reference in their entireties. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

The invention claimed is:

1. A method of treating an AIM2 and 1F116 inflammasome associated inflammatory disease comprising administering a composition comprising a polypeptide having 70% or greater sequence identity with PYRIN domain-only protein 3 (POP3) (SEQ ID NO: 62).

2. The method of claim 1, wherein the polypeptide comprises 100% sequence identity with POP3 (SEQ ID NO: 62).

3. The method of claim 1, wherein the composition is co-administered with one or more additional treatments.

* * * * *